(12) United States Patent
Fleck et al.

(10) Patent No.: US 9,169,205 B2
(45) Date of Patent: Oct. 27, 2015

(54) PYRROLIDINE DERIVATIVES, PHARMACEUTICAL COMPOSITIONS AND USES THEREOF

(71) Applicants: Martin Fleck, Warthausen (DE); Niklas Heine, Biberach an der Riss (DE); Bernd Nosse, Biberach an der Riss (DE); Gerald Juergen Roth, Biberach an der Riss (DE); Annekatrin Heimann, Biberach an der Riss (DE)

(72) Inventors: Martin Fleck, Warthausen (DE); Niklas Heine, Biberach an der Riss (DE); Bernd Nosse, Biberach an der Riss (DE); Gerald Juergen Roth, Biberach an der Riss (DE); Annekatrin Heimann, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 157 days.

(21) Appl. No.: 14/043,128

(22) Filed: Oct. 1, 2013

(65) Prior Publication Data
US 2014/0100211 A1    Apr. 10, 2014

(30) Foreign Application Priority Data
Oct. 8, 2012 (EP) .................... 12187591

(51) Int. Cl.
| | | |
|---|---|---|
| A61K 31/00 | (2006.01) | |
| A61K 31/407 | (2006.01) | |
| A61K 31/4965 | (2006.01) | |
| A61K 31/505 | (2006.01) | |
| A61K 31/44 | (2006.01) | |
| A61K 31/42 | (2006.01) | |
| A61K 31/445 | (2006.01) | |
| C07D 207/12 | (2006.01) | |
| C07D 405/04 | (2006.01) | |
| C07D 405/12 | (2006.01) | |
| C07D 401/12 | (2006.01) | |
| C07D 417/12 | (2006.01) | |
| C07D 403/12 | (2006.01) | |
| C07D 413/12 | (2006.01) | |
| C07D 487/04 | (2006.01) | |
| C07D 471/04 | (2006.01) | |
| C07D 207/28 | (2006.01) | |

(52) U.S. Cl.
CPC ............ *C07D 207/12* (2013.01); *C07D 207/28* (2013.01); *C07D 401/12* (2013.01); *C07D 403/12* (2013.01); *C07D 405/04* (2013.01); *C07D 405/12* (2013.01); *C07D 413/12* (2013.01); *C07D 417/12* (2013.01); *C07D 471/04* (2013.01); *C07D 487/04* (2013.01)

(58) Field of Classification Search
CPC .. C07D 207/12; C07D 405/04; C07D 405/12; C07D 401/12; C07D 417/12; C07D 413/12; C07D 403/12
USPC ................ 514/201.01, 210.21, 210.1, 275, 514/255.05, 352, 374, 330, 210.18, 406, 514/424
See application file for complete search history.

(56) References Cited

U.S. PATENT DOCUMENTS

2012/0157425 A1    6/2012   Roth et al.

FOREIGN PATENT DOCUMENTS

| WO | 2007075629 A2 | 7/2007 |
| WO | 2009105715 A1 | 8/2009 |
| WO | 2012001107 A1 | 1/2012 |
| WO | 2012090219 A2 | 7/2012 |

OTHER PUBLICATIONS

International Search Repot, form PCT/ISA/210, and Written Opinion, form PCT/ISA/237, for corresponding application PCT/EP2013/070507, date of mailing Dec. 18, 2013.

*Primary Examiner* — San-Ming Hui
(74) *Attorney, Agent, or Firm* — Michael P. Morris; Alan R. Stempel

(57) ABSTRACT

Pyrrolidine derivatives of the formula

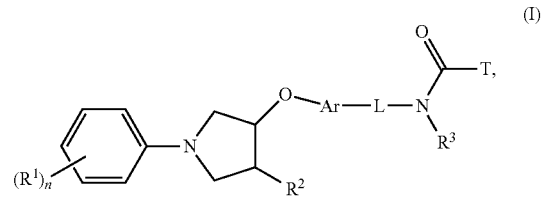

and their use as medicaments for the treatment of obesity and type 2 diabetes.

14 Claims, No Drawings

PYRROLIDINE DERIVATIVES, PHARMACEUTICAL COMPOSITIONS AND USES THEREOF

FIELD OF THE INVENTION

This invention relates to new compounds, in particular pyrrolidine derivatives, to processes for preparing such compounds, to their use as inhibitors of acetyl-CoA carboxylase(s), to methods for their therapeutic use, in particular in diseases and conditions mediated by the inhibition of acetyl-CoA carboxylase(s), and to pharmaceutical compositions comprising them.

BACKGROUND OF THE INVENTION

Obesity is a major public health issue not only for the EU, USA, Japan but also for the world in general. It is associated with a number of serious diseases including diabetes, dyslipidemia, hypertension, cardiovascular and cerebrovascular diseases. Although the underlying mechanisms are not yet fully understood, the impairement of insulin action in target tissues by accumulation of excess lipids is generally regarded as a key mechanism linking obesity to secondary pathologies (G. Wolf, Nutrition Reviews Vol. 66(10):597-600; D B Savage, K F Petersen, G I Shulman, Physiol Rev. 2007; 87:507-520). Therefore, understanding of cellular lipid metabolism in insulin target tissues is crucial in order to elucidate the development of diseases associated with obesity.

A central event in lipid metabolism is the generation of malonyl-CoA via carboxylation of acetyl-CoA by the two mammalian ACC isoforms ACC1 (ACC-alpha, also termed ACCA) and ACC2 (ACC-beta, also designated ACCB) (Saggerson D. Annu Rev Nutr. 2008; 28:253-72). The malonyl-CoA generated is used for de novo fatty acid synthesis and acts as inhibitor of CPT-1, thereby regulating mitochondrial fatty acid oxidation. Furthermore, malonyl-CoA is also described to act centrally to control food intake, and may play an important role in controlling insulin secretion from the pancreas (G D Lopaschuk, J R Ussher, J S Jaswal. Pharmacol Rev. 2010; 62(2):237-64; D Saggerson Annu Rev Nutr. 2008; 28:253-72), further coordinating the regulation of intermediary metabolism.

Therefore ACC1 and ACC2 have been shown to be major regulators of fatty acid metabolism and are presently considered as an attractive target to regulate the human diseases of obesity, diabetes and cardiovascular complications (S J Wakil and L A Abu-Elheiga, J. Lipid Res. 2009. 50: S138-S143; L. Tong, H J Harwood Jr. Journal of Cellular Biochemistry 99:1476-1488, 2006).

As a result of its unique position in intermediary metabolism, inhibition of ACC offers the ability to inhibit de novo fatty acid production in lipogenic tissues (liver and adipose) while at the same time stimulating fatty acid oxidation in oxidative tissues (liver, heart, and skeletal muscle) and therefore offers an attractive modality for favorably affecting, in a concerted manner, a multitude of cardiovascular risk factors associated with obesity, diabetes, insulin resistance, nonalcoholic steatohepatitis (NASH) and the metabolic syndrome (L. Tong, H J Harwood Jr. Journal of Cellular Biochemistry 99:1476-1488, 2006; Corbett J W, Harwood J H Jr., Recent Pat Cardiovasc Drug Discov. 2007 November; 2(3):162-80).

Furthermore recent data show that cellular toxicity mediated by lipids (lipotoxicity) is implicated in the susceptibitlity to diabetes associated nephropathy (for review see M Murea, B I Freedmann, J S Parks, P A Antinozzi, S C Elbein, L M Ma; Clin J Am Soc Nephrol. 2010; 5:2373-9). A large-scale genome-wide association study in japanese patients identified single nucleotide polymorphism in the ACC2 gene (ACACB) associated with diabetic nephropathy risk which was replicated in nine independent cohorts. In the kidney, dysregulation of fatty acid metabolism leading to increased fatty acid levels is believed to lead to glomerular and tubular dysfunction (M Murea, B I Freedmann, J S Parks, P A Antinozzi, S C Elbein, L M Ma; Clin J Am Soc Nephrol. 2010; 5:2373-9). Therefore inhibitors targeting ACC as key molecule involved in lipid oxidation have the potential to be beneficial for favorably affecting diabetic nephropathy.

Additionally, insulin resistance, deregulated lipid metabolism, lipotoxicity and increased intramuscular lipids have also been described to play a role in type 1 diabetes (I E Schauer, J K Snell-Bergeon, B C Bergman, D M Maahs, A Kretowski, R H Eckel, M Rewers Diabetes 2011; 60:306-14; P Ebeling, B Essén-Gustavsson, J A Tuominen and V A Koivisto Diabetologia 41: 111-115; K J Nadeau, J G Regensteiner, T A Bauer, M S Brown, J L Dorosz, A Hull, P Zeitler, B Draznin, J E B. Reusch J Clin Endocrinol Metab, 2010, 95:513-521). Therefore ACC inhibitors are also considered as interesting drugs for the treatment of type 1 diabetes.

In addition ACC inhibitors also have the potential to intervene in the progression of diseases that result from the rapid growth of malignant cells or invading organisms that are dependent on endogenous lipid synthesis to sustain their rapid proliferation. De novo lipogenesis is known to be required for growth of many tumor cells and ACC up-regulation has been recognized in multiple human cancers, promoting lipogenesis to meet the need of cancer cells for rapid growth and proliferation (C Wang, S Rajput, K Watabe, D F Liao, D Cao Front Biosci 2010; 2:515-26). This is further demonstrated in studies using ACC inhibitors which induced growth arrest and selective cytotoxicity in cancer cells and by RNA interference-mediated knock-down of ACC which inhibited growth and induced apoptosis in different types of cancer cells. Furthermore, ACC1 associates with and is regulated by the breast cancer susceptibility gene 1 (BRCA1). Commonly occurring BRCA1 mutations lead to ACC1 activation and breast cancer susceptibility (C Wang, S Rajput, K Watabe, D F Liao, D Cao Front Biosci 2010; 2:515-26).

Furthermore in central nervous system disorders including but not limited to Alzheimer's disease, Parkinson disease and epilepsy, impairements in neuronal energy metabolism have been described (Ogawa M, Fukuyama H, Ouchi Y, Yamauchi H, Kimura J, J Neurol Sci. 1996; 139(1):78-82). Interventions targeting this metabolic defect may prove beneficial to the patients. One promising intervention is therefore to provide the glucose-compromised neuronscerebral brain neurons with ketone bodies as an alternative substrate (S T Henderson Neurotherapeutics, 2008, 5:470-480; L C Costantini, L J Barr, J L Vogel, S T Henderson BMC Neurosci. 2008, 9 Suppl 2:S16; K W Barañano, A L Hartman. Curr Treat Options Neurol. 2008; 10:410-9). ACC inhibition leading to increased fatty acid oxidation may thereby result in increases in the blood levels of ketone bodies thereby providing an alternative energy substrate for the brain.

Preclinical and clinical evidence indicates that ketone bodies can provide neuroprotective effects in models of Parkinson's disease, AD, hypoxia, ischemia, amyotrophic lateral sclerosis and glioma (L C Costantini, L J Barr, J L Vogel, S T Henderson BMC Neurosci. 2008, 9 Suppl 2:S16) and improved cognitive scores in Alzheimers Diseases patients (M A Reger, S T Henderson, C Hale, B Cholerton, L D Baker, G S Watson, K Hydea, D Chapmana, S Craft Neurobiology of Aging 25 (2004) 311-314). The end result of increased ketone levels is an improvement in mitochondrial efficiency and reduction in the generation of reactive oxygen species (for reviews see L C Costantini, L J Barr, J L Vogel, S T Henderson BMC Neurosci. 2008, 9 Suppl 2:S16; K W Barañano, A L Hartman. Curr Treat Options Neurol. 2008; 10:410-9).

Furthermore, the potential of ACC inhibitors as antifungal agents and as antibacterial agents is well documented (L. Tong, H J Harwood Jr. Journal of Cellular Biochemistry 99:1476-1488, 2006). In addition, ACC inhibitors can be used to combat viral infections. It was discovered recently that viruses rely on the metabolic network of their cellular hosts to provide energy and building blocks for viral replication (Munger J, B D Bennett, A Parikh, X J Feng, J McArdle, H A Rabitz, T Shenk, J D Rabinowitz. *Nat. Biotechnol.* 2008; 26:1179-86). A flux measurement approach to quantify changes in metabolic activity induced by human cytomegalovirus (HCMV) elucidated that infection with HCMV markedly changed fluxes through much of the central carbon metabolism, including glycolysis, tricarboxylic acid cycle and fatty acid biosynthesis. Pharmacological inhibition of fatty acid biosynthesis suppressed the replication of two divergent enveloped viruses (HCMV and influenza A) indicating that fatty acid synthesis is essential for the replication. These examples show that acetyl-CoA fluxes and de novo fatty acid biosynthesis are critical to viral survival and propagation as the newly synthesized fatty acids and phospholipids are important for formation of viral envelopes. Changing the metabolic flux influences the absolute quantity of phospholipid available, the chemical composition and physical properties of the envelope negatively affect viral growth and replication. Hence, ACC inhibitors acting on key enzymes in the fatty acid metabolism, have the potential to be antiviral drugs.

AIM OF THE PRESENT INVENTION

The aim of the present invention is to provide new compounds, in particular new pyrrolidine derivatives, which are active with regard to acetyl-CoA carboxylase(s).

Another aim of the present invention is to provide new compounds, in particular new pyrrolidine derivatives, which are active with regard to ACC2.

A further aim of the present invention is to provide new compounds, in particular new pyrrolidine derivatives, which have an inhibitory effect on acetyl-CoA carboxylase(s) in vitro and/or in vivo and possess suitable pharmacological and pharmacokinetic properties to use them as medicaments.

A further aim of the present invention is to provide new compounds, in particular new pyrrolidine derivatives, which have an inhibitory effect on ACC2 in vitro and/or in vivo and possess suitable pharmacological and pharmacokinetic properties to use them as medicaments.

A further aim of the present invention is to provide effective ACC inhibitors, in particular for the treatment of metabolic disorders, for example of obesity and/or diabetes.

A further aim of the present invention is to provide methods for treating a disease or condition mediated by the inhibition of acetyl-CoA carboxylase(s) in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular pyrrolidine derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

Within the scope of the present invention it has now surprisingly been found that the new compounds of general formula (I) as described hereinafter exhibit an inhibiting activity with regard to acetyl-CoA carboxylase(s).

According to another aspect of the present invention it has been found that the new compounds of general formula (I) as described hereinafter exhibit an inhibiting activity with regard to ACC2.

In a first aspect the present invention provides a compound of general formula

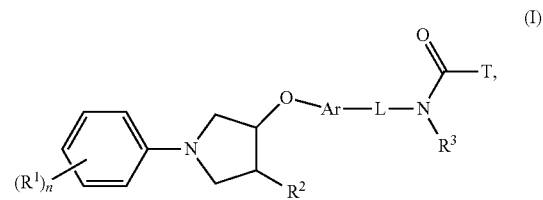

wherein

Ar is selected from the group Ar-G1 consisting of phenylene and pyridinylene, which are each optionally substituted with one or two substituents independently selected from F, Cl, —O—CH$_3$ and CH$_3$;

R$^1$ independently of one another are selected from the group R$^1$-G1 consisting of halogen, CN, C$_{1-4}$-alkyl, C$_{3-6}$-cycloalkyl, —O—(C$_{1-6}$-alkyl), —O—(C$_{3-6}$-cycloalkyl), —O—(CH$_2$)$_{1-2}$—(C$_{3-6}$-cycloalkyl), —O—CH$_2$—R$^4$, —O-tetrahydrofuranyl and —O-heteroaryl, wherein R$^4$ is tetrahydrofuranyl, aryl or heteroaryl, wherein heteroaryl is selected from the group consisting of pyridinyl, pyrimidinyl, pyridazinyl and pyrazinyl, wherein aryl is selected from the group consisting of phenyl and naphthyl, wherein each alkyl is optionally substituted with 1 to 6 F or with one —OH or —O—C$_{1-3}$-alkyl, wherein each cycloalkyl is optionally substituted with 1 to 4 F or with one CH$_3$, CF$_3$ or —CO$_2$(C$_{1-3}$-alkyl), and wherein each tetrahydrofuranyl, aryl or heteroaryl is optionally substituted with one or two substituents independently selected from F, Cl, C$_{1-3}$-alkyl or —O—CH$_3$;

or two R$^1$ groups attached to adjacent C-atoms together may form an C$_{3-5}$-alkylene bridging group in which one or two —CH$_2$— groups may be replaced by O and the alkylene bridge may optionally be substituted by one or two F or CH$_3$;

n is 1, 2 or 3;

R$^2$ is selected from the group R$^2$-G1 consisting of H, F, CN and —O—(C$_{1-3}$-alkyl), wherein the alkyl group is optionally substituted with —OCH$_3$;

R$^3$ is selected from the group R$^3$-G1 consisting of H and C$_{1-3}$-alkyl;

L is selected from the group L-G1 consisting of straight-chain C$_{1-3}$-alkylene, which is optionally substituted with one or two C$_{1-3}$-alkyl groups; and T is selected from the group T-G1 consisting of:
- $C_{1-4}$-alkyl which is optionally substituted with one to three F or with one CN, OH, —O—$CH_3$, —O—C(=O)—$CH_3$, or a heteroaryl group preferably selected from the group consisting of: pyrrolyl, isoxalyl, pyrimidinyl and pyrazinyl,
  wherein each of said heteroaryl groups is optionally substituted with $C_{1-3}$-alkyl;
- $C_{3-6}$-cycloalkyl which is optionally substituted with one or two F, CN, $CH_3$, OH, —O—($C_{1-3}$-alkyl), $NH_2$, —NH—(C=O)$CH_3$, —C(=O)—$NH_2$, —C(=O)—NH($C_{1-3}$-alkyl) or —C(=O)—N($C_{1-3}$-alkyl)$_2$;
- —O—($C_{1-2}$-alkyl);
- morpholinyl;
- —$NH_2$, wherein each H is optionally independently replaced with $C_{1-3}$-alkyl or wherein one H is optionally replaced with a 5-membered heteroaryl group containing 1 to 3 heteroatoms selected independently from O, S, N and NH, wherein said heteroaryl group is optionally substituted with $C_{1-3}$-alkyl, or with a —$CH_2$-pyrimidyl group;
- a 5-membered heteroaryl group containing one or two heteroatoms selected independently from O, S, N and NH, which is optionally substituted with one or two substituents selected independently from the group consisting of:
  Cl, CN, $NH_2$, —NH—C(=O)—$C_{1-3}$-alkyl, —NH—C(=O)—$CH_2$OH, —NH—C(=O)—$CH_2$O$CH_3$, —NH—C(=O)—$CH_2$O—C(=O)$CH_3$, —NH—C(=O)—$CH_2$O$CH_2$-Ph, $C_{1-3}$-alkyl and —O—($C_{1-2}$-alkyl), wherein each alkyl group is optionally substituted with one to three F or with one OH;
- a 6-membered heteroaryl group containing 1 or 2 N, which is optionally substituted with —$CH_3$ or —C(=O)—NH($CH_3$);
- phenyl optionally substituted with F, Cl, CN or —O$CH_3$; and
- a group selected from among:

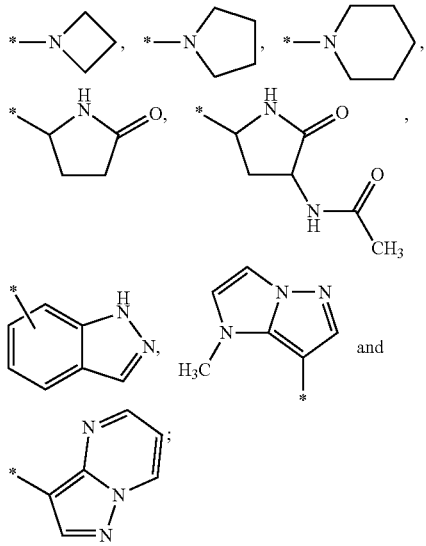

a tautomer or stereoisomers thereof,
or a salt thereof,
or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of acetyl-CoA carboxylase(s) in a patient in need thereof characterized in that a compound of general formula (I) or a pharmaceutically acceptable salt thereof is administered to the patient.

According to another aspect of the invention, there is provided a method for treating a metabolic disease or disorder in a patient in need thereof characterized in that a compound of general formula (I) or a pharmaceutically acceptable salt thereof is administered to the patient.

According to another aspect of the invention, there is provided a method for treating a cardiovascular disease or disorder in a patient in need thereof characterized in that a compound of general formula (I) or a pharmaceutically acceptable salt thereof is administered to the patient.

According to another aspect of the invention, there is provided a method for treating a neurodegenerative disease or disorder or for treating a disease or disorder of the central nervous system in a patient in need thereof characterized in that a compound of general formula (I) or a pharmaceutically acceptable salt thereof is administered to the patient.

According to another aspect of the invention, there is provided a method for treating a cancer, a malignant disorder or a neoplasia in a patient in need thereof characterized in that a compound of general formula (I) or a pharmaceutically acceptable salt thereof is administered to the patient.

According to another aspect of the invention, there is provided the use of a compound of the general formula (I) or a pharmaceutically acceptable salt thereof for the manufacture of a medicament for a therapeutic method as described hereinbefore and hereinafter.

According to another aspect of the invention, there is provided a compound of the general formula (I) or a pharmaceutically acceptable salt thereof for a therapeutic method as described hereinbefore and hereinafter.

In a further aspect this invention relates to a method for treating a disease or condition mediated by the inhibition of acetyl-CoA carboxylase(s) in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) or a pharmaceutically acceptable salt thereof in combination with one or more additional therapeutic agents for the treatment or prevention of diseases or conditions which are mediated by the inhibition of acetyl-CoA carboxylase(s).

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly Ar, $R^1$, $R^2$, $R^3$, $R^4$, L, T and n, are defined as above and hereinafter. If residues, substituents, or groups occur several times in a compound, as for example $R^1$, they may have the same or different meanings. Some preferred meanings of individual groups and substituents of the compounds according to the invention will be given hereinafter. Any and each of these definitions may be combined with each other.

Ar:

Ar-G1:

The group Ar is preferably selected from the group Ar-G1 as defined hereinbefore and hereinafter.

Ar-G2:

In another embodiment the group Ar is selected from the group Ar-G2 consisting of:

wherein each A is independently selected from a group consisting of CH, CF and N, with the proviso that 0 or 1 A may be N.

Ar-G2a:

In another embodiment the group Ar is selected from the group Ar-G2a consisting of:

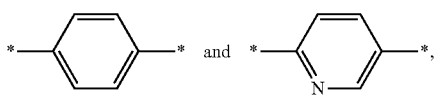

wherein the right-hand side of the above Ar groups is linked to L, and the left-hand side of the above moieties is linked to the oxygen figuring in formula (I), and wherein the before mentioned phenyl group is optionally monosubstituted with F.

Ar-G3:

In another embodiment the group Ar is selected from the group Ar-G3 consisting of: phenylene, which is optionally monosubstituted with F.

Ar-G3a:

In another embodiment the group Ar is selected from the group Ar-G3a consisting of: phenylene.

Ar-G3b:

In another embodiment the group Ar is selected from the group Ar-G3b consisting of: pyridinylene.

Ar-G4:

In another embodiment the group Ar is selected from the group Ar-G4 consisting of:

wherein the before mentioned group is optionally monosubstituted with F.

Ar-G4a:

In another embodiment the group Ar is selected from the group Ar-G4a consisting of:

Ar-G4b:

In another embodiment the group Ar is selected from the group Ar-G4b consisting of:

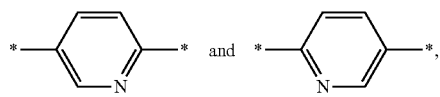

wherein the right-hand side of the above Ar groups is linked to L, and the left-hand side of the above moieties is linked to the oxygen figuring in formula (I).

Ar-G4b1:

In another embodiment the group Ar is selected from the group Ar-G4b1 consisting of:

wherein the right-hand side of the above Ar group is linked to L, and the left-hand side of the above moiety is linked to the oxygen figuring in formula (I).

Ar-G4b2:

In another embodiment the group Ar is selected from the group Ar-G4b2 consisting of:

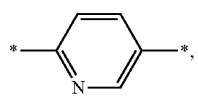

wherein the right-hand side of the above Ar group is linked to L, and the left-hand side of the above moiety is linked to the oxygen figuring in formula (I).

$R^1$:

$R^1$-G1:

The group $R^1$ is preferably selected from the group $R^1$-G1 as defined hereinbefore and hereinafter.

$R^1$-G2:

In another embodiment the group $R^1$ is selected from the group $R^1$-G2 consisting of: F, Cl, Br, CN, $C_{1-4}$-alkyl, $C_{3-5}$-cycloalkyl, —O—($C_{1-4}$-alkyl), —O—($C_{3-5}$-cycloalkyl), —O—$CH_2$—($C_{3-5}$-cycloalkyl), —O—$CH_2$-aryl, —O-tetrahydrofuranyl and —O-heteroaryl,
  wherein heteroaryl is selected from the group consisting of pyridinyl, pyrimidinyl, pyridazinyl and pyrazinyl,
  wherein aryl is phenyl and naphthyl,
  wherein each alkyl is optionally substituted with 1 to 3 F or with one —O—$CH_3$, and
  wherein each cycloalkyl is optionally substituted with 1 to 2 F or with one $CH_3$, $CF_3$ or —$CO_2CH_3$;
or two $R^1$ groups attached to adjacent C-atoms together may form a —$(CH_2)_2$—O—, —O—$CH_2$—O—, —O—$(CH_2)_2$—

O— or —O—(CH$_2$)$_3$—O— bridge that is optionally substituted with one or two F or CH$_3$.

R$^1$-G3:

In another embodiment the group R$^1$ is selected from the group R$^1$-G3 consisting of: F, Cl, CN, C$_{1-4}$-alkyl, —O—(C$_{1-4}$-alkyl), —O—(C$_{3-4}$-cycloalkyl), —O—CH$_2$-cyclopropyl and —O—CH$_2$-cyclobutyl, wherein each alkyl is optionally substituted with 1 to 3 F, and wherein each cyclopropyl and cyclobutyl are optionally substituted with 1 to 2 F or with one CF$_3$;

or two R$^1$ groups attached to adjacent C-atoms together may form a —(CH$_2$)$_2$—O—, —O—CH$_2$—O—, —O—(CH$_2$)$_2$—O— or —O—(CH$_2$)$_3$—O— bridge that is optionally substituted with one or two F.

R$^1$-G4:

In another embodiment the group R$^1$ is selected from the group R$^1$-G4 consisting of: F, Cl, CN, C$_{1-4}$-alkyl, —O—(C$_{1-4}$-alkyl), —O—(C$_{3-5}$-cycloalkyl),

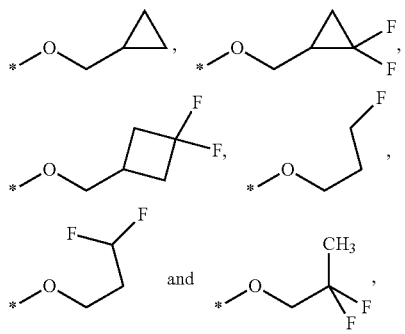

or two R$^1$ groups attached to adjacent C-atoms together may form a —O—(CH$_2$)$_2$—O— or —O—(CH$_2$)$_3$—O— bridge.

R$^1$-G4a:

In another embodiment the group R$^1$ is selected from the group R$^1$-G4a consisting of: —O—(C$_{1-3}$-alkyl), —O—(C$_{3-4}$-cycloalkyl),

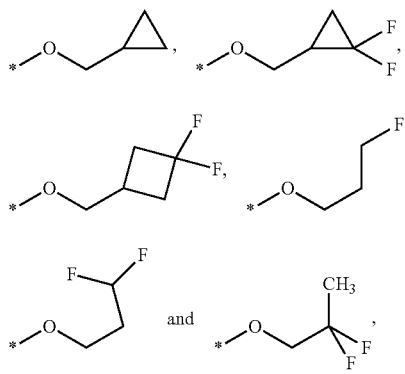

or, if n is 2 or 3, two R$^1$ groups attached to adjacent C-atoms together may form a —O—(CH$_2$)$_{2-3}$—O— bridge, and/or the second and/or third R$^1$ group is selected from the group consisting of F, Cl, CN and CH$_3$.

R$^1$-G5:

In another embodiment the group R$^1$ is selected from the group R$^1$-G5 consisting of:

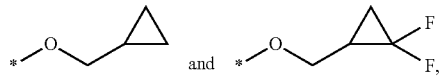

while, if n is 2, the second R$^1$ group is F.

n n is 1, 2 or 3.

Preferably, n is 1 or 2.

More preferably, n is 2.

Most preferably, n is 1.

R$^2$

R$^2$-G1:

The group R$^2$ is preferably selected from the group R$^2$-G1 as defined hereinbefore and hereinafter.

R$^2$-G2:

In another embodiment the group R$^2$ is selected from the group R$^2$-G2 consisting of: H, F, —O—CH$_3$, —O—CH$_2$CH$_3$ and —O—CH$_2$CH$_2$OCH$_3$.

R$^2$-G3:

In another embodiment the group R$^2$ is selected from the group R$^2$-G3 consisting of: H, F, —O—CH$_3$ and —O—CH$_2$CH$_2$OCH$_3$.

R$^2$-G4:

In another embodiment the group R$^2$ is selected from the group R$^2$-G4 consisting of: H, —O—CH$_3$ and —O—CH$_2$CH$_2$OCH$_3$.

R$^2$-G5:

In another embodiment the group R$^2$ is selected from the group R$^2$-G5 consisting of H and —OCH$_3$.

R$^2$-G6:

In another embodiment, the group R$^2$ is selected from the group R$^2$-G6 consisting of H.

R$^3$:

R$^3$-G1:

The group R$^3$ is preferably selected from the group R$^3$-G1 as defined hereinbefore and hereinafter.

R$^3$-G2:

In one embodiment the group R$^3$ is selected from the group R$^3$-G2 consisting of H and CH$_3$.

R$^3$-G3:

In another embodiment the group R$^3$ is selected from the group R$^3$-G3 consisting of H.

L:

L-G1:

The group L is preferably selected from the group L-G1 as defined hereinbefore and hereinafter.

L-G2:

In one embodiment the group L is selected from the group L-G2 consisting of: a straight-chain C$_{1-3}$-alkylene group which is optionally substituted with one or two CH$_3$ groups.

L-G3:

In another embodiment the group L is selected from the group L-G3 consisting of: a straight-chain C$_{1-2}$-alkylene group which is optionally substituted with one methyl group.

L-G4:

In another embodiment the group L is selected from the group L-G4 consisting of:

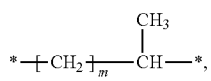

wherein m is 0 or 1, and
wherein the asterisk to the left-hand side is connected to Ar
and the asterisk to the right-hand side is connected to N atom
depicted in formula (I).

L-G5:
In another embodiment the group L is selected from the group L-G5 consisting of: —CH(CH₃)—.

L-G5a:
In another embodiment the group L is selected from the group L-G5a consisting of:

wherein the asterisk to the left-hand side is connected to Ar
and the asterisk to the rigth-hand side is connected to N atom
depicted in formula (I).

L-G5b:
In another embodiment the group L is selected from the group L-G5b consisting of:

wherein the asterisk to the left-hand side is connected to Ar
and the asterisk to the right-hand side is connected to N atom
depicted in formula (I).

T:
T-G1:
The group T is preferably selected from the group T-G1 as defined hereinbefore and hereinafter.

T-G2:
In one embodiment the group T is selected from the group T-G2 consisting of:
  $C_{1-3}$-alkyl which is optionally substituted with one to three F or with one CN, OH or —OCH₃;
  —OCH₃;
  —NH₂, wherein each H is optionally independently replaced with $C_{1-3}$-alkyl or wherein one H is optionally replaced with a 5-membered heteroaryl group containing one to three heteroatoms selected independently from O, S, N and NH, or with a —CH₂-pyrimidyl group;
  a 5-membered heteroaryl group containing 2 heteroatoms selected independently from O, S, N and NH, which is optionally substituted with one or two substituents selected independently from the group consisting of: Cl, CN, NH₂, —NH—C(=O)—$C_{1-3}$-alkyl, —NH—C(=O)—CH₂OCH₃, —NH—C(=O)—CH₂O—C(=O)CH₃, —NH—C(=O)—CH₂OCH₂-Ph, —O—CH₃ and $C_{1-2}$-alkyl,
    wherein each alkyl is optionally substituted with one to three F; and
  a group selected from among:

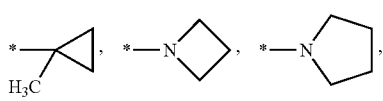

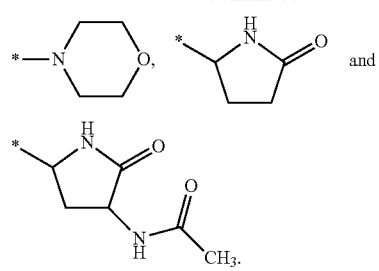

T-G3:
In one embodiment the group T is selected from the group T-G3 consisting of:
  $C_{1-3}$-alkyl which is optionally substituted with one to three F or with one CN, OH or —OCH₃;
  cyclopropyl which is optionally substituted with one or two F or with one CN, CH₃, OH, —OCH₃ or —(C=O)—N(CH₃)₂;
  —OCH₃;
  —NH₂, wherein each H is optionally independently replaced with $C_{1-3}$-alkyl or wherein one H is optionally replaced by isoxazolyl or by —CH₂-pyrimidyl; and
  a 5-membered heteroaryl group selected from imidazolyl, oxazolyl, pyrazolyl, isoxoazolyl, thioazolyl and isothiazolyl,
  wherein said 5-membered heteroaryl group is optionally substituted with one or two substituents selected independently from the group consisting of:
    Cl, CN, NH₂, —NH—C(=O)—$C_{1-3}$-alkyl, —NH—C(=O)—CH₂OCH₃, —NH—C(=O)—CH₂O—C(=O)CH₃, —NH—C(=O)—CH₂OCH₂-Ph, —O—CH₃ and $C_{1-2}$-alkyl,
    wherein each alkyl is optionally substituted with one to three F.

T-G4:
In one embodiment the group T is selected from the group T-G4 consisting of:
  $C_{1-3}$-alkyl which is optionally substituted with one to three F or with one CN;

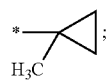

—OCH₃;
  —NH₂, wherein each H is optionally independently replaced with methyl or ethyl;

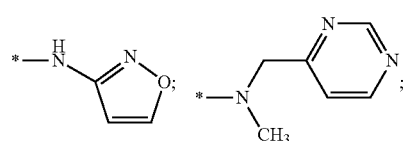

and
a 5-membered heteroaryl group selected from:

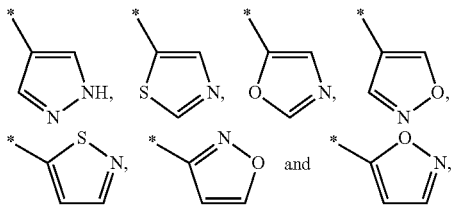

wherein said 5-membered heteroaryl group is optionally substituted with one or two substituents selected independently from the group consisting of: Cl, CN, $NH_2$, —NH—C(=O)—$C_{1-3}$-alkyl, —NH—C(=O)—$CH_2OCH_3$, —NH—C(=O)—$CH_2$—O—C(=O)$CH_3$, —NH—C(=O)—$CH_2OCH_2$-Ph and $CH_3$.

T-G5:

In one embodiment the group T is selected from the group T-G5 consisting of:

$C_{1-3}$-alkyl which is optionally substituted with one to three F or with one CN;

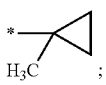

—$OCH_3$;

—$NH_2$, wherein each H is optionally independently replaced with methyl or ethyl;

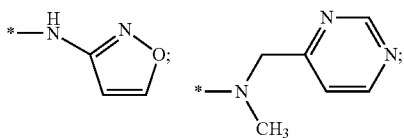

and
a 5-membered heteroaryl group selected from:

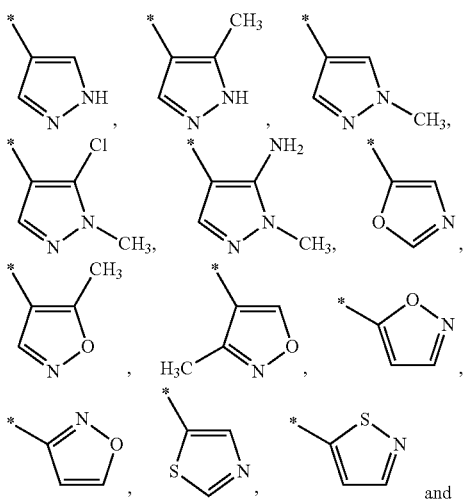

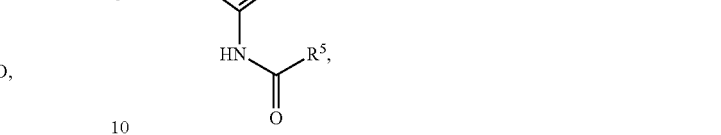

wherein $R^5$ is H, —(C=O)—($C_{1-2}$-alkyl), —(C=O)—$CH_2OCH_3$, —(C=O)—$CH_2$—O—C(=O)$CH_3$ or —(C=O)—$CH_2OCH_2$-Ph.

T-G5a:

In one embodiment the group T is selected from the group T-G5a consisting of: —$CH_3$, —$CHF_2$, —$CF_3$, —$CH_2CN$, —$CH_2CH_3$, —$CH(CN)CH_3$, —$OCH_3$, —$NH(CH_3)$, —$N(CH_3)_2$, —$NH(CH_2CH_3)$,

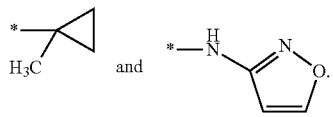

Preferably, T is $CH_3$.

T-G5b:

In one embodiment the group T is selected from the group T-G5b consisting of

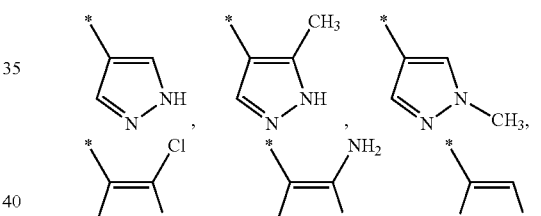

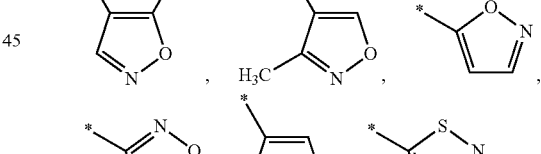

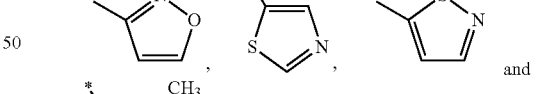

wherein $R^5$ is H, —(C=O)—($C_{1-2}$-alkyl), —(C=O)—$CH_2OCH_3$, —(C=O)—$CH_2$—O—C(=O)$CH_3$ or —(C=O)—$CH_2OCH_2$-Ph.

T-G6:

In another embodiment the group T is selected from the group T-G6 consisting of: —$CH_3$, —$CHF_2$, —$CF_3$, —CH$_2$CN, —CH$_2$OH, —CH$_2$CH$_3$, —OCH$_3$, —NH(CH$_3$), —N(CH$_3$)$_2$, —N(CH$_3$)(CH$_2$CH$_3$), —NH(CH$_2$CH$_3$),
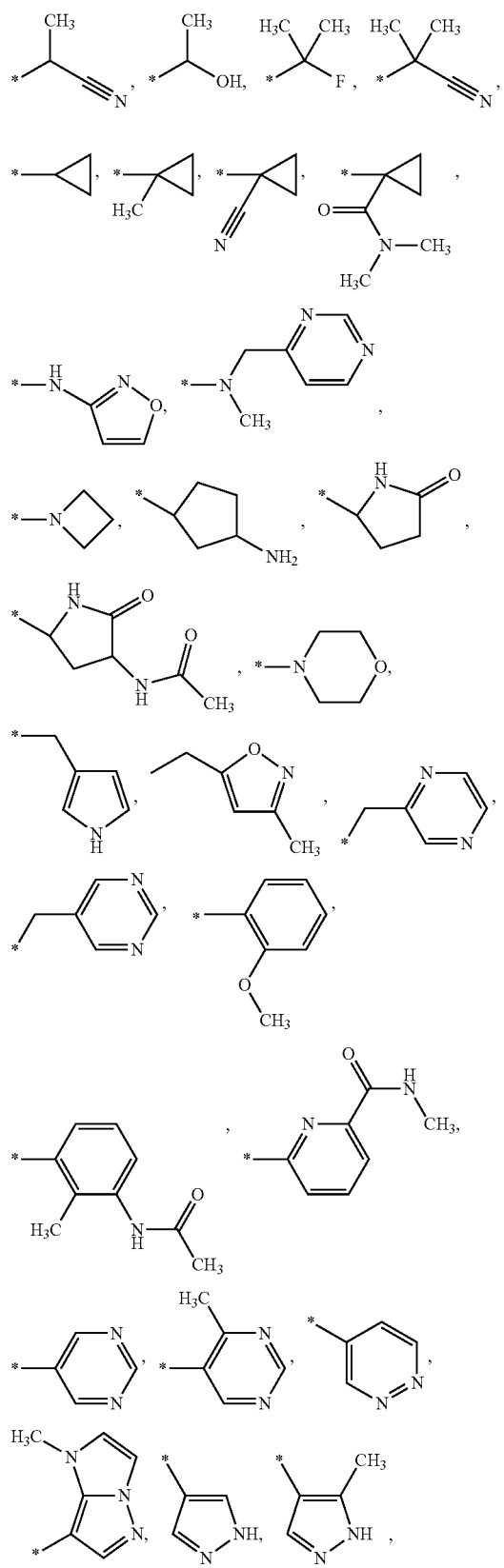
-continued
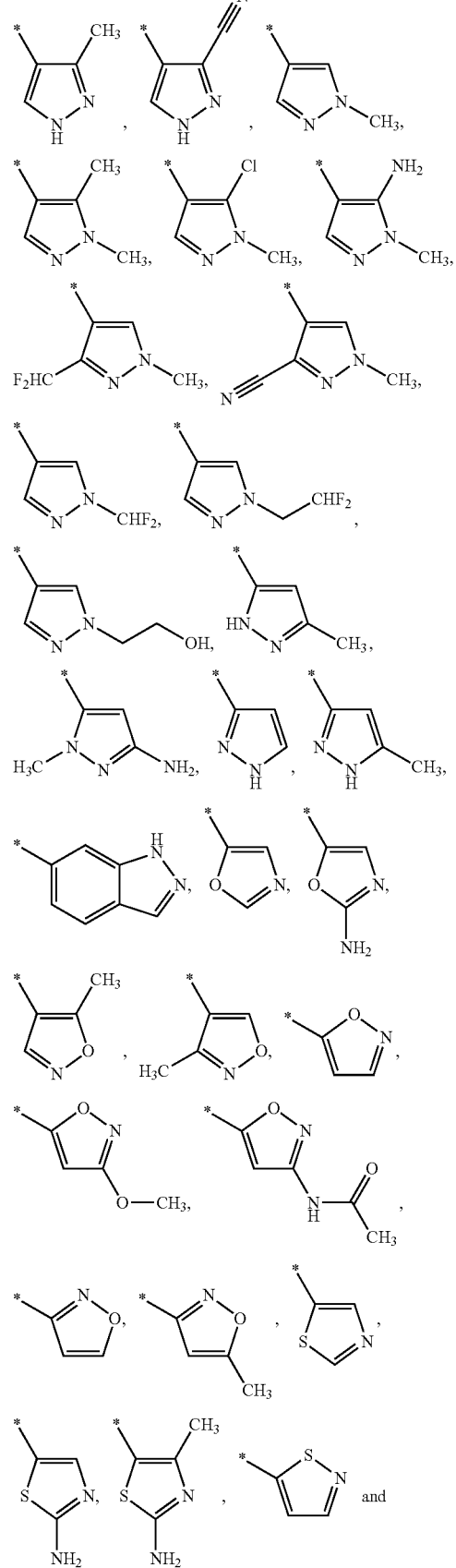
and

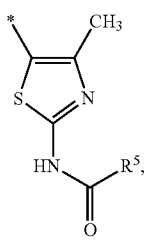

wherein $R^5$ is H, —(C=O)—($C_{1-2}$-alkyl), —(C=O)—$CH_2OCH_3$, —(C=O)—$CH_2O$—C(=O)$CH_3$ or —(C=O)—$CH_2OCH_2$-Ph.

Examples of preferred subgeneric embodiments according to the present invention are set forth in the following table, wherein each substituent group of each embodiment is defined according to the definitions set forth hereinbefore and wherein all other substituents of the formula (I) are defined according to the definitions set forth hereinbefore:

| Embodiment | $R^1$ | Ar | $R^2$ | L | $R^3$ | T | n |
|---|---|---|---|---|---|---|---|
| E-1 | $R^1$-G2 | Ar-G1 | $R^2$-G1 | L-G3 | $R^3$-G2 | T-G2 | 1 or 2 |
| E-2 | $R^1$-G2 | Ar-G3 | $R^2$-G3 | L-G3 | $R^3$-G3 | T-G5b + $CH_3$ | 1 or 2 |
| E-3 | $R^1$-G2 | Ar-G3 | $R^2$-G3 | L-G3 | $R^3$-G3 | T-G6 | 1 or 2 |
| E-4 | $R^1$-G4 | Ar-G4 | $R^2$-G3 | L-G5 | $R^3$-G3 | T-G3 | 1 or 2 |
| E-5 | $R^1$-G4 | Ar-G4a | $R^2$-G5 | L-G5 | $R^3$-G3 | T-G4 | 1 or 2 |
| E-6 | $R^1$-G4 | Ar-G4a | $R^2$-G5 | L-G5 | $R^3$-G3 | T-G5 | 1 or 2 |
| E-7 | $R^1$-G4 | Ar-G4a | $R^2$-G5 | L-G5 | $R^3$-G3 | T-G5b + $CH_3$ | 1 or 2 |
| E-8 | $R^1$-G5 | Ar-G3 | $R^2$-G3 | L-G5 | $R^3$-G3 | T-G3 | 1 or 2 |
| E-9 | $R^1$-G5 | Ar-G3 | $R^2$-G5 | L-G5 | $R^3$-G3 | T-G4 | 1 or 2 |
| E-10 | $R^1$-G5 | Ar-G4 | $R^2$-G5 | L-G5 | $R^3$-G5 | T-G5 | 1 or 2 |
| E-11 | $R^1$-G5 | Ar-G4a | $R^2$-G3 | L-G3 | $R^3$-G3 | T-G5b + $CH_3$ | 1 or 2 |
| E-12 | $R^1$-G5 | Ar-G4a | $R^2$-G5 | L-G5 | $R^3$-G3 | T-G5b + $CH_3$ | 1 or 2 |
| E-13 | $R^1$-G5 | Ar-G4a | $R^2$-G5 | L-G5 | $R^3$-G3 | T-G6 | 1 or 2 |
| E-14 | $R^1$-G5 | Ar-G4a | $R^2$-G5 | L-G5 | $R^3$-G3 | T-G5 | 1 or 2 |

The following preferred embodiments of compounds of the formula (I) are described using generic formulae (I.1) to (I.4b), wherein any tautomers and stereoisomers, solvates, hydrates and salts thereof, in particular the pharmaceutically acceptable salts thereof, are encompassed.

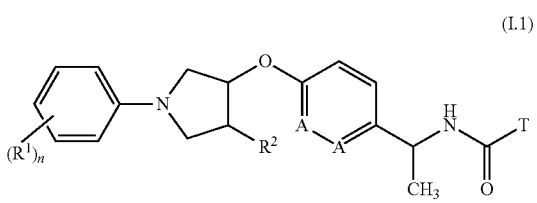
(I.1)

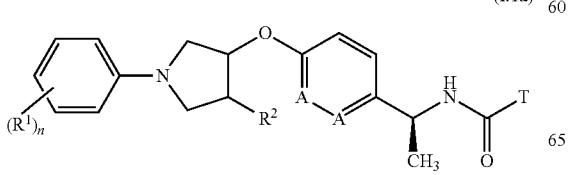
(I.1a)

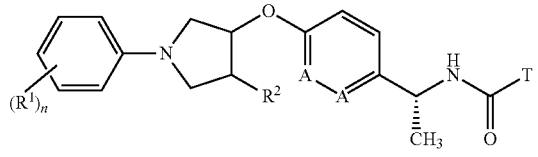
(I.1b)

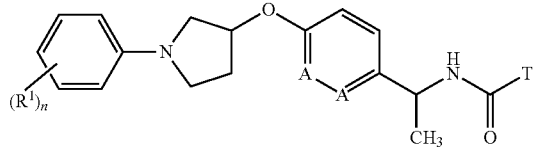
(I.2)

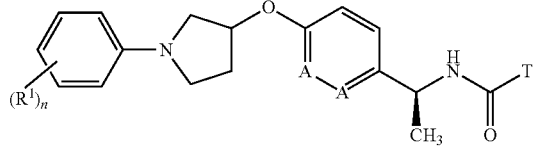
(I.2a)

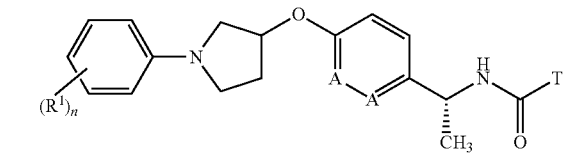
(I.2b)

(I.3)

(I.3a)

(I.3b)

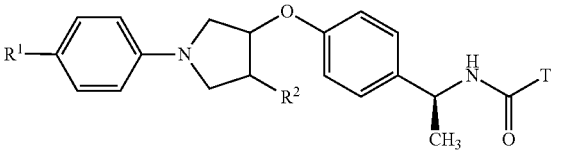
(I.4)

-continued

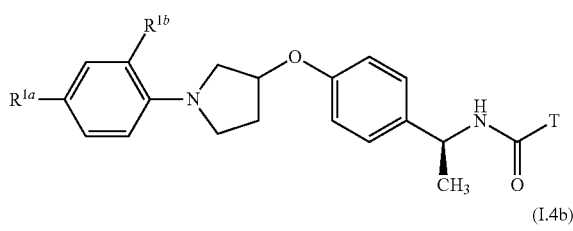
(I.4a)

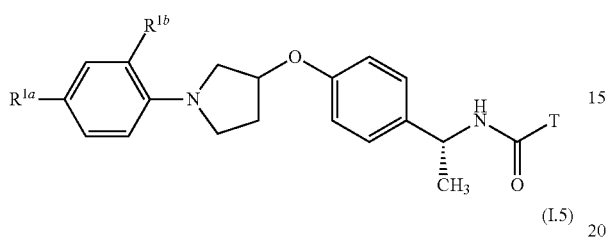
(I.4b)

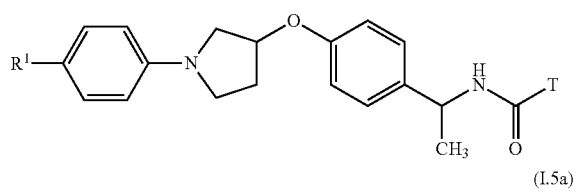
(I.5)

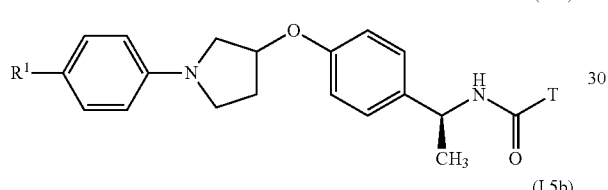
(I.5a)

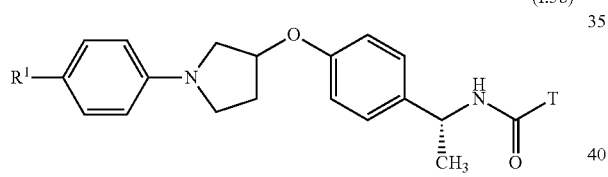
(I.5b)

wherein in each of the above formulae (I.1) to (I.5b), the groups A, $R^1$, $R^2$, T and n are defined as hereinbefore and hereinafter.

A preferred embodiment of the present invention concerns compounds of general formula

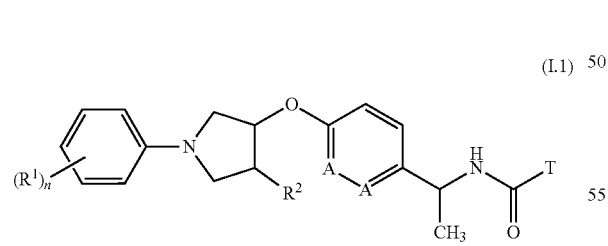
(I.1)

wherein
A are each independently from one another selected from the group consisting of CH, CF and N, with the proviso that 0 or 1 A may be N;
n is 1, 2 or 3;
$R^1$ is selected from a group consisting of F, Cl, Br, CN, $C_{1-3}$-alkyl, $C_{3-5}$-cycloalkyl, —O—($C_{1-4}$-alkyl), —O—($C_{3-5}$-cycloalkyl), —O—$CH_2$—($C_{3-5}$-cycloalkyl), —O—tetrahydrofuranyl and —O-heteroaryl, wherein heteroaryl is selected from the group consisting of pyridinyl, pyrimidinyl, pyridazinyl and pyrazinyl,
wherein each alkyl is optionally substituted with one to three F or with one —O—$CH_3$, and
wherein each cycloalkyl is optionally substituted with one to two F or with one $CF_3$ or one —$CO_2CH_3$;
or two $R^1$ groups attached to adjacent C-atoms together may form a —O—$CH_2$—O—, —O—$(CH_2)_2$—O— or —O—$(CH_2)_3$—O— bridge that is optionally substituted with one or two substituents selected form F and $CH_3$;
$R^2$ is H, F, —O—$CH_3$ or —O—$CH_2CH_2OCH_3$; and
T is selected from a group consisting of:
—$CH_3$, —$CHF_2$, —$CF_3$, —$CH_2CN$, —$CH_2OH$, —$CH_2CH_3$, —$OCH_3$, —$NH(CH_3)$, —$N(CH_3)_2$, —$N(CH_3)(CH_2CH_3)$, —$NH(CH_2CH_3)$,

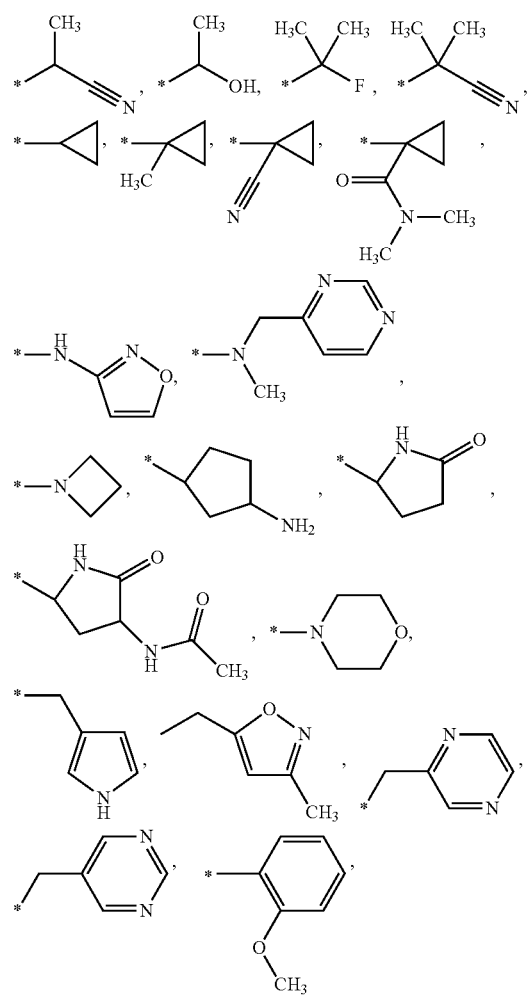

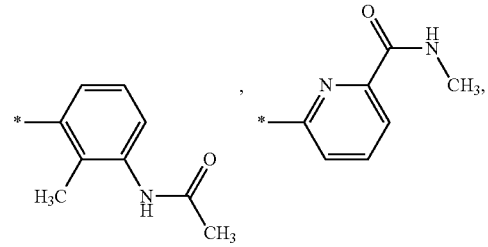

-continued

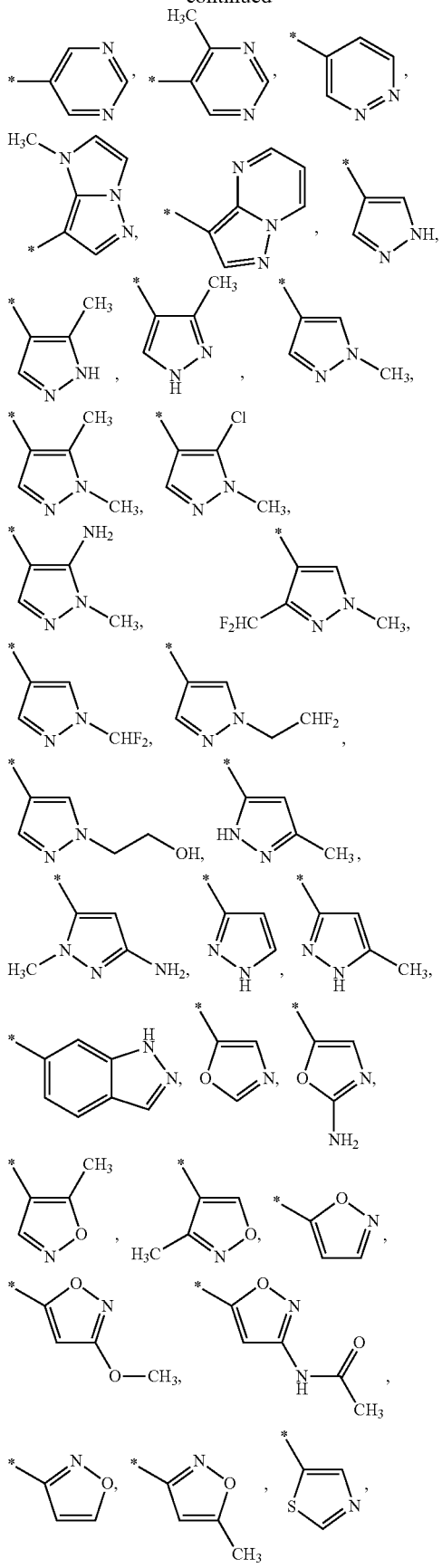

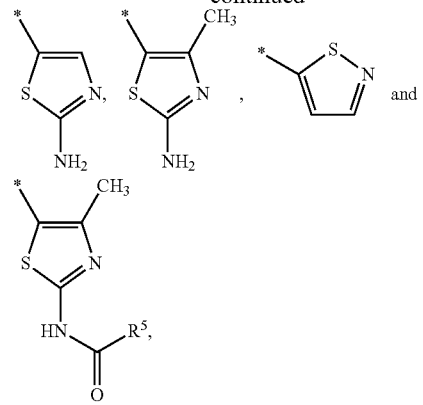

wherein $R^5$ is H, —(C=O)—($C_{1-2}$-alkyl), —(C=O)—$CH_2OCH_3$, —(C=O)—$CH_2O$—C(=O)$CH_3$ or —(C=O)—$CH_2OCH_2$-Ph;
a tautomer or stereoisomer thereof,
or a salt thereof
or a solvate or hydrate thereof.

A preferred embodiment of the present invention concerns compounds of general formula (I.4)

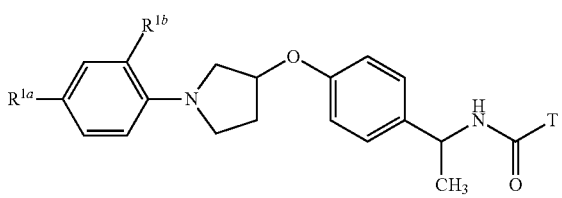

wherein
$R^{1a}$ is —O—($C_{1-3}$-alkyl), —O—($C_{3-4}$-cycloalkyl),

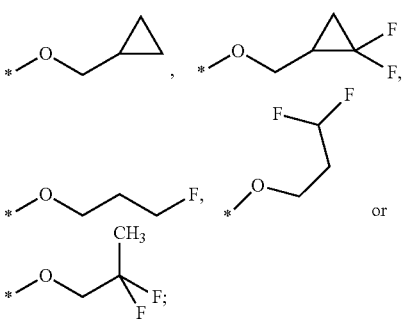

$R^{1b}$ is H, F, Cl, CN, $CH_3$ or $OCH_3$; and
T is $C_{1-3}$-alkyl which is optionally substituted with one to three F or with one CN;

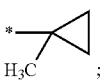

—$OCH_3$;
—$NH_2$, wherein each H is optionally independently replaced with methyl or ethyl;

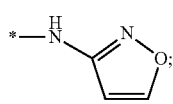 [SMILES: *Nc1ccon1]

or a 5-membered heteroaryl group selected from:

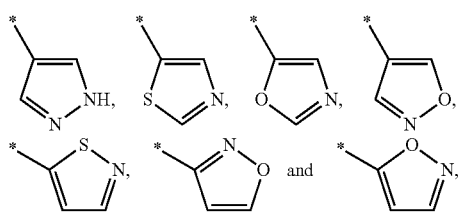

wherein said 5-membered heteroaryl group is optionally substituted with one or two substituents selected independently from the group consisting of: Cl, NH$_2$, —NH—C(=O)—C$_{1-3}$-alkyl, —NH—C(=O)—CH$_2$OCH$_3$, —NH—C(=O)—CH$_2$O—C(=O)CH$_3$, —NH—C(=O)—CH$_2$OCH$_2$-Ph and CH$_3$;

a tautomer or stereoisomer thereof, or a pharmaceutically acceptable salt thereof.

Preferred compounds of the invention include:

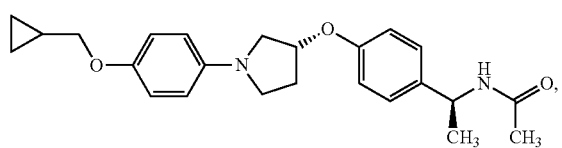

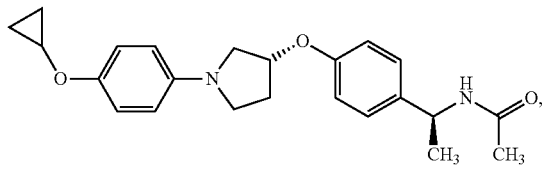

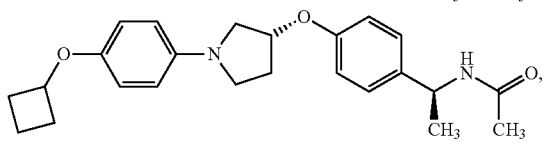

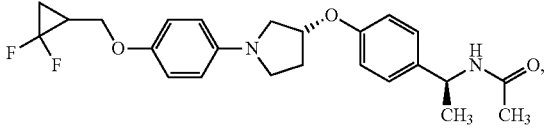

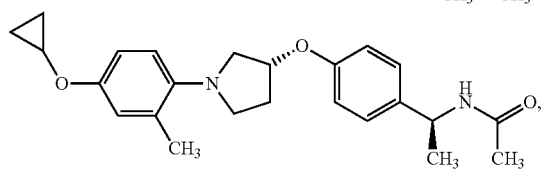

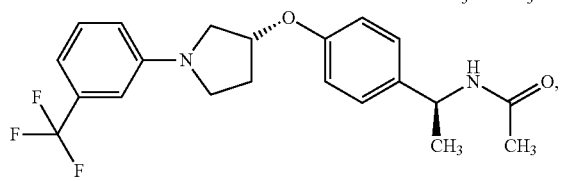

-continued

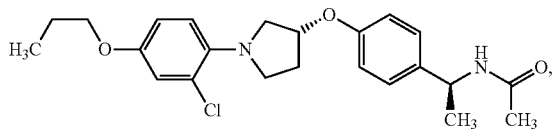

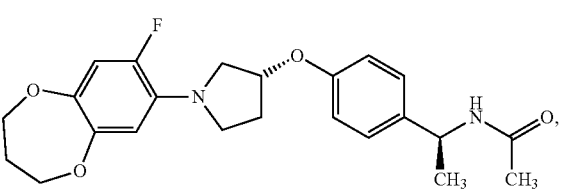

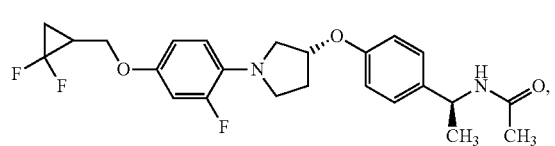

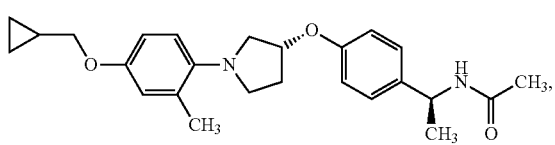

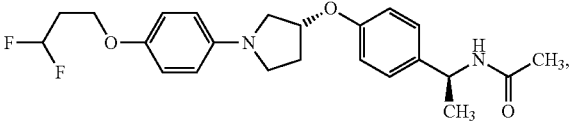

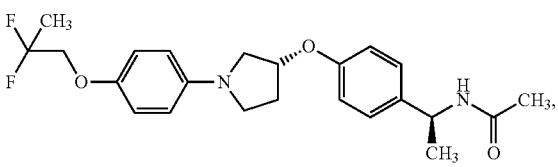

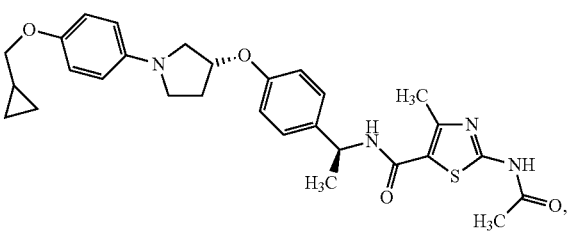

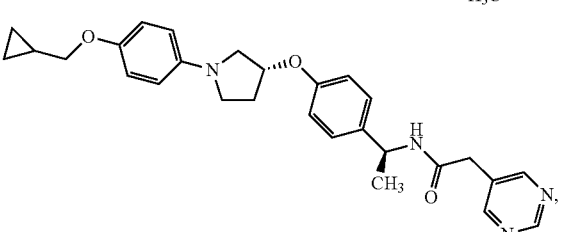

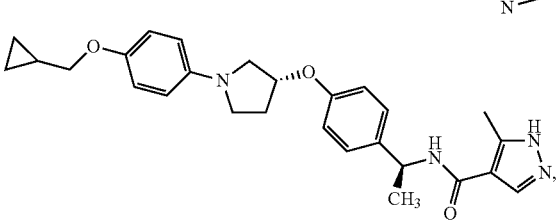

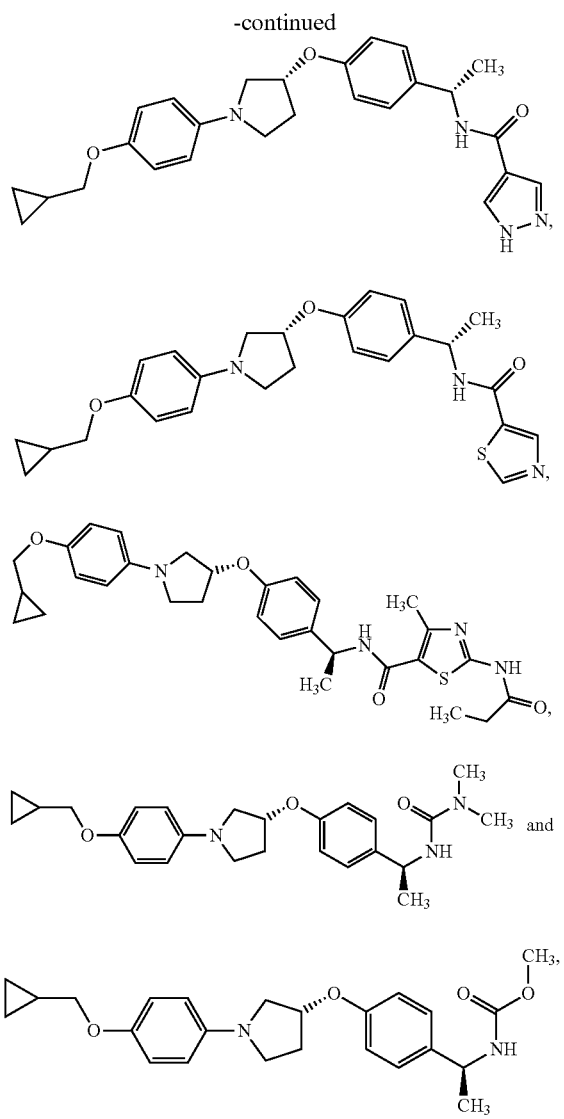

and the pharmaceutically acceptable salts thereof.

Particularly preferred compounds, including their tautomers and stereoisomers, the salts thereof, or any solvates or hydrates thereof, are described in the experimental section hereinafter.

The compounds according to the invention may be obtained using methods of synthesis which are known to the one skilled in the art and described in the literature of organic synthesis. Preferably, the compounds are obtained analogously to the methods of preparation explained more fully hereinafter, in particular as described in the experimental section.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of acetyl-CoA carboxylase(s) (ACC) with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

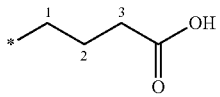

wherein the carboxy group is attached to the third carbon atom of the propyl group. The terms "1-methylpropyl-", "2,2-dimethylpropyl-" or "cyclopropylmethyl-" group represent the following groups:

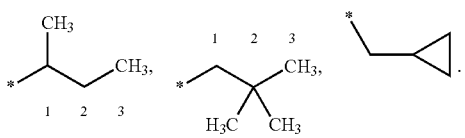

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_2CH_3))$—, —$(CHCH(CH_3)_2)$— and —$C(CH_3)(CH_2CH_3)$—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —$CH$=$CH_2$, —$CH$=$CH$—$CH_3$, —$CH_2$—$CH$=$CH_2$.

The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term $C_{2-3}$-alkenylene includes —$CH$=$CH$—, —$CH$=$CH$—$CH_2$—, —$CH_2$—$CH$=$CH$—.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —$C$≡$CH$, —$C$≡$C$—$CH_3$, —$CH_2$—$C$≡$CH$.

The term "$C_{2-n}$-alkynylene" is used for a group as defined in the definition for "$C_{1-n}$-alkylene" with at least two carbon atoms, if at least two of those carbon atoms of said group are bonded to each other by a triple bond. For example the term $C_{2-3}$-alkynylene includes —$C$≡$C$—, —$C$≡$C$—$CH_2$—, —$CH_2$—$C$≡$C$—.

The term "$C_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term $C_{3-10}$-carbocyclyl includes $C_{3-10}$-cylcoalkyl, $C_{3-10}$-cycloalkenyl, octahydro-pentalenyl, octahydroindenyl, decahydronaphthyl, indanyl, tetrahydronaphthyl. Most preferably, the term $C_{3-n}$-carbocyclyl denotes $C_{3-n}$-cycloalkyl, in particular $C_{3-7}$-cycloalkyl.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc.

The term "$C_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably, the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, preferably mono-, bi- or spirocyclic-ring system containing one or more heteroatoms selected from N, O or $S(O)_r$ with r=0, 1 or 2, which in addition may have a carbonyl group. More preferably, the term "heterocyclyl" as used herein, either alone or in combination with another radical, means a saturated or unsaturated, even more preferably, a saturated mono-, bi- or spirocyclic-ring system containing 1, 2, 3 or 4 heteroatoms selected from N, O or $S(O)_r$ with r=0, 1 or 2 which in addition may have a carbonyl group. The term "heterocyclyl is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

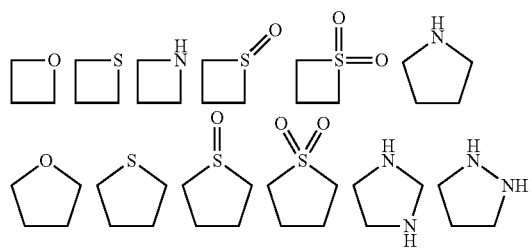

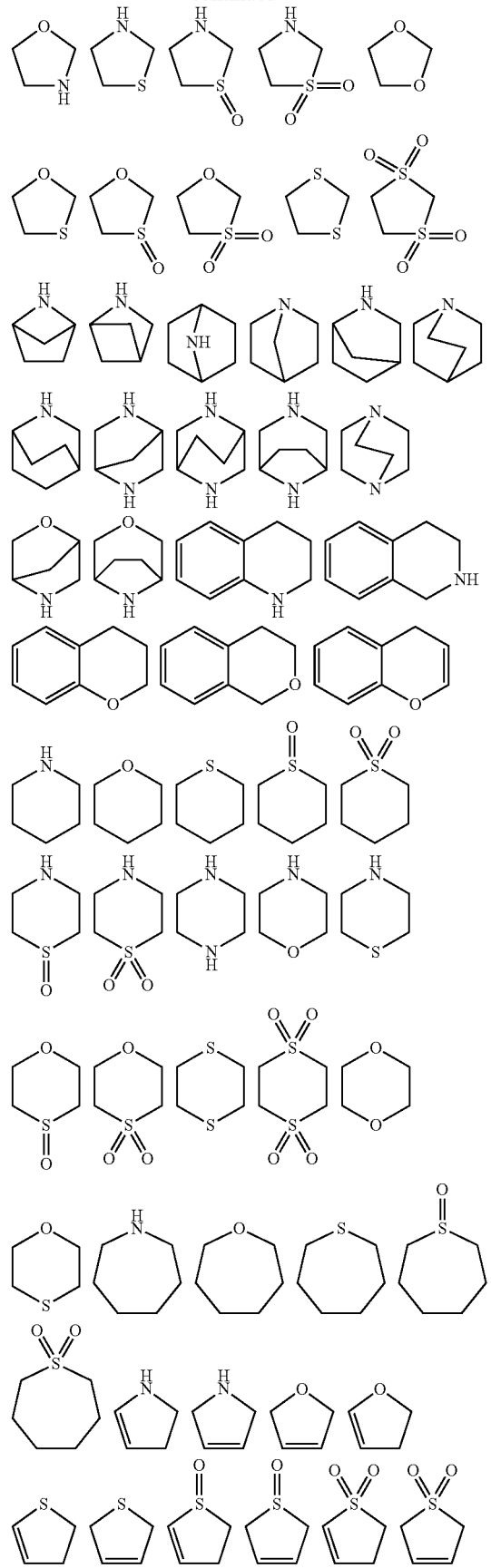

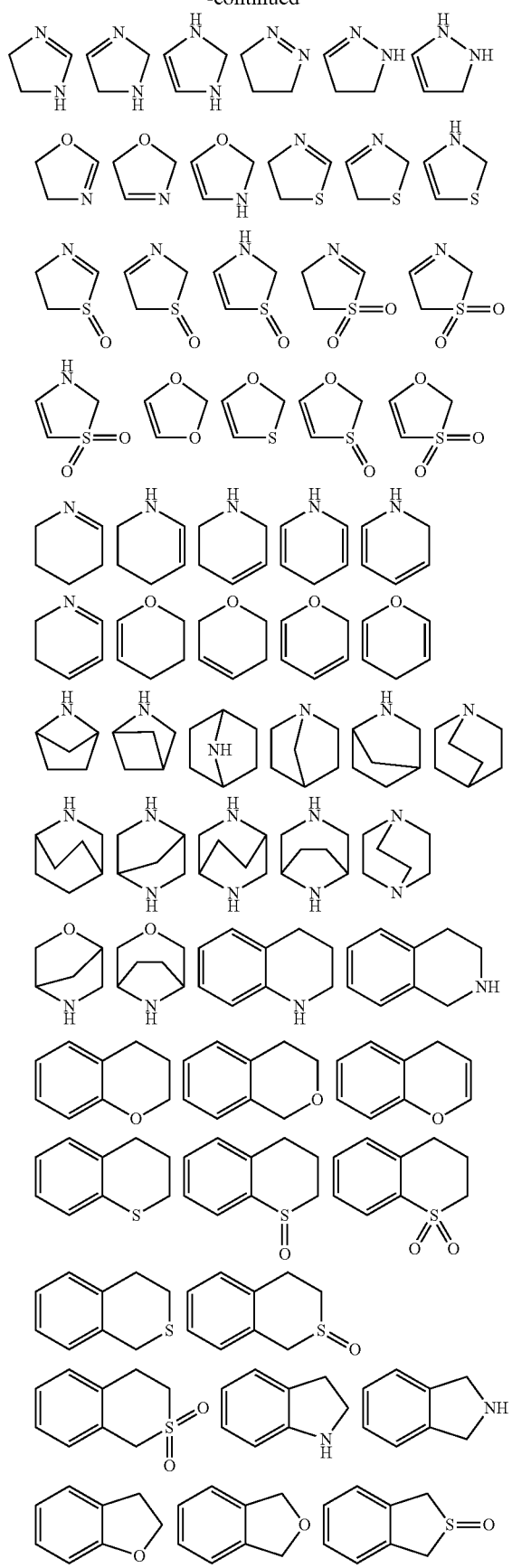
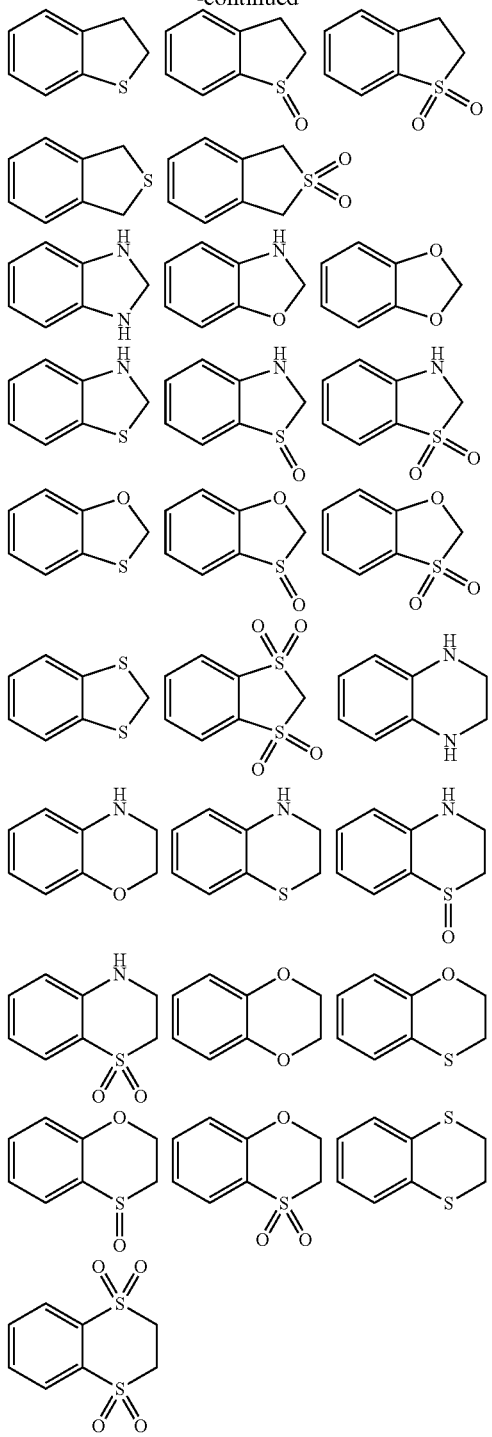

The term "heteroaryl" means a mono- or polycyclic, preferably mono- or bicyclic-ring system containing one or more heteroatoms selected from N, O or $S(O)_r$ with r=0, 1 or 2 wherein at least one of the heteroatoms is part of an aromatic ring, and wherein said ring system may have a carbonyl group. More preferably, the term "heteroaryl" as used herein, either alone or in combination with another radical, means a mono- or bicyclic-ring system containing 1, 2, 3 or 4 heteroatoms selected from N, O or $S(O)_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

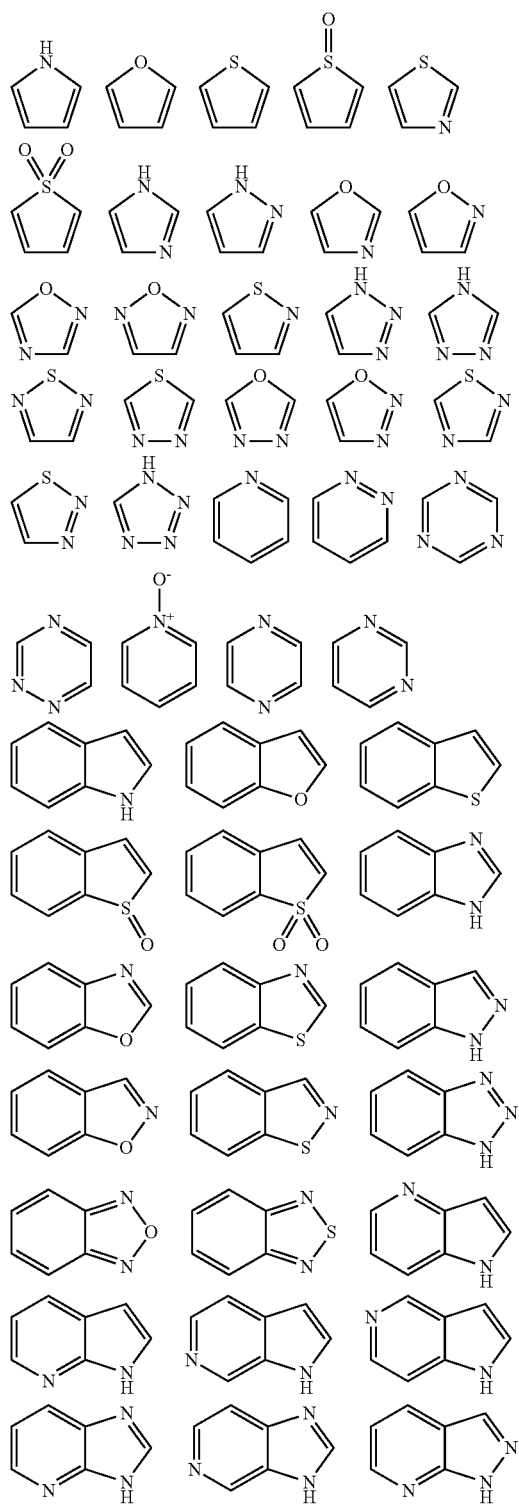

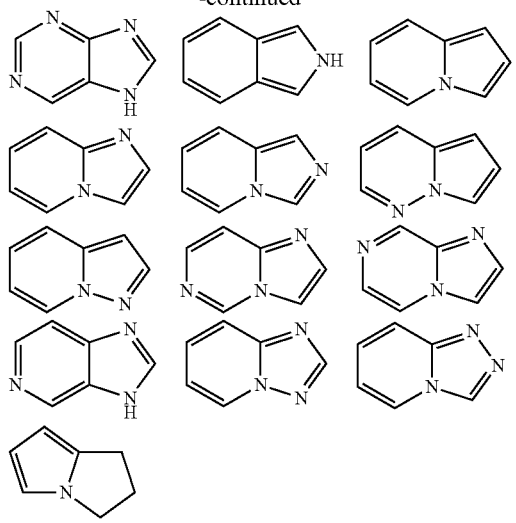

Many of the terms given above may be used repeatedly in the definition of a formula or group and in each case have one of the meanings given above, independently of one another.

Pharmacological Activity

The activity of the compounds of the invention may be demonstrated using the following ACC2 assay:

Spectrophotometric 384 Well Assay

Malonyl CoA formation by acetyl CoA carboxylases is stoichometrically linked to the consumption of ATP. ACC2 activity is measured in a NADH-linked kinetic method measuring ADP generated during the ACC reaction using a coupled lactate dehydrogenase/pyruvate kinase reaction.

For biological testing, a human ACC2 construct which lacks the 128 amino acids at the N-terminus for increased solubility (nt 385-6966 in Genbank entry AJ575592) is cloned. The protein is then expressed in insect cells using a baculoviral expression system. Protein purification is performed by anion exchange.

All compounds are dissolved in dimethyl sulfoxide (DMSO) to a concentration of 10 mM.

Assay reactions are then carried out in 384-well plates, with hACC2 in an appropriate dilution and at final assay concentrations (f.c.) of 100 mM Tris (pH 7.5), 10 mM trisodium citrate, 25 mM $KHCO_3$, 10 mM $MgCl_2$, 0.5 mg/ml BSA, 3.75 mM reduced L-glutathione, 15 U/ml lactate dehydrogenase, 0.5 mM phosphoenolpyruvate, 15 U/ml pyruvate kinase, compounds at different concentrations at final DMSO concentrations of 1%.

The enzymatic reaction is then started by addition of a mixture of NADH, acetyl Coenzyme A (both 200 µM f.c.) and ATP (500 uM f.c.). The decrease of the optical density (slope S) is then determined at 25° C. at a wavelength of 340 nm over 15 minutes in a spectrophotometric reader.

Each assay microtiter plate contains wells with vehicle instead of compound as controls for the non-inhibited enzyme (100% CTL; 'HIGH') and wells without acetyl-CoA as controls for non-specific NADH degradation (0% CTL; 'LOW').

The slope S is used for calculation of % CTL=(S(compound)−S('LOW'))/(S('HIGH')−S('LOW'))*100. Compounds will give values between 100% CTL (no inhibition) and 0% CTL (complete inhibition).

For $IC_{50}$ value determination, the sample slope in the presence of the test compound after subtraction of the low controls (S(compound)−S('LOW')) are used.

An IC$_{50}$ value is derived from the compound slopes at different dosages after subtraction of the low controls (S(compound)–S('LOW')) by non-linear regression curve fitting (equation y=(A+((B–A)/(1+((C/x)^D))))).

The compounds of general formula (I) according to the invention for example have IC$_{50}$ values below 10000 nM, particularly below 1000 nM, preferably below 300 nM.

In the following table the activity expressed as IC$_{50}$ (μM) of compounds according to the invention is presented wherein the IC$_{50}$ values are determined in the ACC2 assay as described hereinbefore. The term "Example" refers to the example numbers according to the following experimental section.

| Example | IC$_{50}$ [μM] |
|---|---|
| 1.1 | 0.054 |
| 1.2 | 0.198 |
| 1.3 | 0.263 |
| 1.4 | 0.514 |
| 1.5 | 0.204 |
| 1.6 | 0.108 |
| 1.7 | 0.229 |
| 1.8 | 0.140 |
| 1.9 | 1.149 |
| 1.10 | 0.230 |
| 1.11 | 0.226 |
| 1.12 | 0.899 |
| 1.13 | 0.155 |
| 1.14 | 0.036 |
| 1.15 | 0.214 |
| 1.16 | 0.025 |
| 1.17 | 0.894 |
| 1.18 | 0.214 |
| 1.19 | 0.240 |
| 1.20 | 2.962 |
| 1.21 | 0.573 |
| 1.22 | 0.559 |
| 1.23 | 0.084 |
| 1.24 | 0.589 |
| 1.25 | 0.086 |
| 1.26 | 0.397 |
| 1.27 | 0.110 |
| 1.28 | 0.672 |
| 1.29 | 0.060 |
| 1.30 | 0.174 |
| 1.31 | 0.913 |
| 1.32 | 0.538 |
| 1.33 | 0.125 |
| 1.34 | 0.224 |
| 1.35 | 0.899 |
| 1.36 | 0.097 |
| 1.37 | 0.484 |
| 1.38 | 0.685 |
| 1.39 | 0.791 |
| 1.40 | 0.147 |
| 1.41 | 0.045 |
| 1.42 | 0.589 |
| 1.43 | 0.274 |
| 1.44 | 0.435 |
| 1.45 | 0.108 |
| 1.46 | 0.226 |
| 1.47 | 0.339 |
| 1.48 | 0.180 |
| 1.49 | 0.775 |
| 1.50 | 0.385 |
| 1.51 | 0.175 |
| 1.52 | 0.599 |
| 1.53 | 0.204 |
| 1.54 | 0.300 |
| 1.55 | 0.214 |
| 1.56 | 0.298 |
| 1.57 | 0.443 |
| 1.58 | 0.354 |
| 1.59 | 0.118 |
| 1.60 | 0.415 |
| 1.61 | 0.845 |
| 1.62 | 0.335 |
| 1.63 | 0.389 |
| 1.64 | 0.108 |
| 1.65 | 0.875 |
| 1.66 | 0.791 |
| 1.67 | 0.323 |
| 1.68 | 0.566 |
| 1.69 | 0.440 |
| 1.70 | 0.053 |
| 1.71 | 0.272 |
| 1.72 | 0.558 |
| 1.73 | 0.230 |
| 1.74 | 1.675 |
| 1.75 | 0.709 |
| 1.76 | 1.210 |
| 1.77 | 0.749 |
| 1.78 | 0.546 |
| 1.79 | 0.496 |
| 1.80 | 0.574 |
| 1.81 | 0.804 |
| 1.82 | 1.481 |
| 1.83 | 0.350 |
| 1.84 | 0.069 |
| 1.85 | 0.226 |
| 1.86 | 0.065 |
| 1.87 | 0.108 |
| 1.88 | 0.102 |
| 1.89 | 0.224 |
| 1.90 | 0.040 |
| 1.91 | 0.085 |
| 1.92 | 0.384 |
| 1.93 | 0.601 |
| 1.94 | 0.221 |
| 1.95 | 0.166 |
| 1.96 | 0.061 |
| 1.97 | 0.244 |
| 1.98 | 0.064 |
| 1.99 | 0.383 |
| 1.100 | 0.087 |
| 1.101 | 0.269 |
| 1.102 | 0.212 |
| 1.103 | 0.231 |
| 1.104 | 0.363 |
| 2.1 | 0.040 |
| 2.2 | 0.671 |
| 2.3 | 0.399 |
| 2.4 | 0.517 |
| 2.5 | 0.800 |
| 2.6 | 0.705 |
| 2.7 | 0.121 |
| 2.8 | 0.330 |
| 2.9 | 0.138 |
| 2.10 | 0.079 |
| 2.11 | 0.132 |
| 2.12 | 0.397 |
| 2.13 | 0.359 |
| 2.14 | 0.705 |
| 2.15 | 0.315 |
| 2.16 | 0.864 |
| 2.17 | 0.346 |
| 2.18 | 0.551 |
| 2.19 | 0.124 |
| 2.20 | 0.774 |
| 2.21 | 0.045 |
| 2.22 | 0.030 |
| 2.23 | 0.056 |
| 2.24 | 0.040 |
| 2.24 | 0.038 |
| 2.26 | 0.047 |
| 2.27 | 0.107 |
| 2.28 | 0.105 |
| 2.29 | 0.400 |
| 2.30 | 0.793 |
| 2.31 | 0.071 |
| 2.32 | 0.016 |

-continued

| Example | IC$_{50}$ [μM] |
|---|---|
| 2.33 | 0.793 |
| 2.34 | 0.071 |
| 2.35 | 0.273 |
| 2.36 | 0.200 |
| 2.37 | 0.065 |
| 2.38 | 0.017 |
| 2.39 | 0.465 |
| 2.40 | 0.384 |
| 2.41 | 0.023 |
| 2.42 | 0.020 |
| 2.43 | 0.160 |
| 2.44 | 0.055 |
| 2.45 | 0.993 |
| 2.46 | 0.382 |
| 2.47 | 0.385 |
| 2.48 | 0.445 |
| 2.49 | 0.885 |
| 2.50 | 0.065 |
| 2.51 | 0.495 |
| 2.52 | 0.805 |
| 2.53 | 1.020 |
| 2.54 | 0.045 |
| 2.55 | 0.053 |
| 2.56 | 0.417 |
| 2.57 | 0.122 |
| 2.58 | 0.743 |
| 2.59 | 0.680 |
| 2.60 | 0.260 |
| 2.61 | 0.397 |
| 2.62 | 0.411 |
| 2.63 | 0.238 |
| 2.64 | 0.357 |
| 2.65 | 0.090 |
| 3.1 | 0.074 |
| 3.2 | 0.055 |
| 3.3 | 1.271 |
| 3.4 | 0.165 |
| 3.5 | 0.198 |
| 3.6 | 0.504 |
| 3.7 | 0.056 |
| 3.8 | 0.073 |
| 3.9 | 0.205 |
| 3.10 | 0.218 |
| 3.11 | 0.947 |
| 3.12 | 1.284 |
| 3.13 | 0.863 |
| 4.1 | 0.460 |
| 4.2 | 0.309 |
| 4.3 | 0.169 |
| 4.4 | 0.560 |
| 4.5 | 0.660 |
| 4.6 | 0.360 |
| 4.7 | 0.630 |
| 5.1 | 0.049 |
| 5.2 | 1.356 |
| 6 | 0.039 |
| 7.1 | 1.777 |
| 7.2 | 0.762 |
| 7.3 | 0.199 |
| 8.1 | 0.373 |
| 8.2 | 0.365 |
| 8.3 | 0.061 |
| 9 | 1.746 |
| 10 | 0.163 |

In view of their ability to inhibit acetyl-CoA carboxylase(s), the compounds of general formula (I) according to the invention and the corresponding salts thereof are theoretically suitable for the treatment, including preventative treatment of all those diseases or conditions which may be affected or which are mediated by the inhibition of acetyl-CoA carboxylase(s), in particular ACC2, activity.

Accordingly, the present invention relates to a compound of general formula (I) as a medicament.

Furthermore, the present invention relates to the use of a compound of general formula (I) for the treatment and/or prevention of diseases or conditions which are mediated by the inhibition of acetyl-CoA carboxylase(s), in particular ACC2, in a patient, preferably in a human.

In yet another aspect the present invention relates a method for treating, including preventing a disease or condition mediated by the inhibition of acetyl-CoA carboxylase(s) in a mammal that includes the step of administering to a patient, preferably a human, in need of such treatment a therapeutically effective amount of a compound of the present invention, or a pharmaceutical composition thereof.

Diseases and conditions mediated by inhibitors of acetyl-CoA carboxylases embrace metabolic and/or cardiovascular and/or neurodegenerative diseases or conditions.

According to one aspect the compounds of the present invention are particularly suitable for treating diabetes mellitus, in particular Type 2 diabetes, Type 1 diabetes, and diabetes-related diseases, such as is hyperglycemia, metabolic syndrome, impaired glucose tolerance, diabetic neuropathy, diabetic nephropathy, diabetic retinopathy, dyslipidemia, hypertension, hyperinsulinemia, and insulin resistance syndrome, hepatic insulin resistance, including complications such as macro- and microvascular disorders, including thromboses, hypercoagulable and prothrombotic states (arterial and venous), high blood pressure, coronary artery disease and heart failure, increased abdominal girth, hypercoagulability, hyperuricemia, micro-albuminemia.

According to another aspect the compounds of the present invention are particularly suitable for treating overweight, obesity, including visceral (abdominal) obesity, nonalcoholic fatty liver disease (NAFLD) and obesity related disorders, such as for example weight gain or weight maintenance Obesity and overweight are generally defined by body mass index (BMI), which is correlated with total body fat and estimates the relative risk of disease. BMI is calculated by weight in kilograms divided by height in meters squared (kg/m$^2$). Overweight is typically defined as a BMI of 25-29.9 kg/m$^2$, and obesity is typically defined as a BMI of 30 kg/m$^2$ or greater.

According to another aspect the compounds of the present invention are particularly suitable for treating, inclduing preventing, or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, pancreatic beta cell degeneration and diabetic complications (such as macro- and microvascular disorders, atherosclerosis, coronary heart disease, stroke, peripheral vascular disease, nephropathy, hypertension, neuropathy, and retinopathy).

In addition the compounds of the present invention are suitable for treating dyslipidemias in general and more specifically elevated lipid concentrations in the blood and in tissues, dysregulation of LDL, HDL and VLDL, in particular high plasma triglyceride concentrations, high postprandial plasma triglyceride concentrations, low HDL cholesterol concentration, low apoA lipoprotein concentrations, high LDL cholesterol concentrations, high apoB lipoprotein concentrations, including atherosclerosis, coronary heart disease, cerebrovascular disorders, diabetes mellitus, metabolic syndrome, obesity, insulin resistance and/or cardiovascular disorders.

ACC inhibition may lead to a centrally stimulating effect on food intake. Therefore compounds of the present invention may be suitable for treating eating disorders such as anorexia nervosa.

In addition the compounds of the present invention may provide neuroprotective effects in patients with Parkinson's disease, Alzheimer's disease, hypoxia, ischemia, amyotrophic lateral sclerosis or glioma and may improve cognitive scores in Alzheimer's diseases patients.

Further diseases and conditions mediated by inhibitors of acetyl-CoA carboxylases embrace but are not limited to:

A. disorders of fatty acid metabolism and glucose utilization disorders; disorders in which insulin resistance is involved;
B. hepatic disorders and conditions related thereto, including:
  fatty liver, hepatic steatosis, non-alcoholic hepatitis, non-alcoholic steatohepatitis (NASH), alcoholic hepatitis, acute fatty liver, fatty liver of pregnancy, drug-induced hepatitis, iron storage diseases, hepatic fibrosis, hepatic cirrhosis, hepatoma, viral hepatitis;
C. skin disorders and conditions and those associated with polyunsaturated fatty acids, such as
  eczema, acne, sebaceous gland diseases, psoriasis, keloid scar formation or prevention, other diseases releated to mucous membrane fatty acid composition;
D. primary hypertriglyceridemia or secondary hypertriglyceridemias following familial histiocytic reticulosis, lipoprotein lipase deficiency, hyperlipo-proteinemias, apolipoprotein deficiency (e.g. apoCII or apoE deficiency);
E. diseases or conditions related to neoplastic cellular proliferation, for example benign or malignant tumors, cancer, neoplasias, metastases, carcinogenesis;
F. diseases or conditions related to neurological, psychiatric or immune disorders or conditions;
G. other diseases or conditions in which inflammatory reactions, cell differentiation and/or other ACC-mediated aspects may for example be involved are:
  atherosclerosis such as, for example (but not restricted thereto), coronary sclerosis including angina pectoris or myocardial infarction, stroke, ischemic, stroke and transient ischemic attack (TIA),
  peripheral occlusive disease,
  vascular restenosis or reocclusion,
  chronic inflammatory bowel diseases such as, for example, Crohn's disease and ulcerative colitis,
  pancreatitis,
  sinusitis,
  retinopathy, ischemic retinopathy,
  adipose cell tumors,
  lipomatous carcinomas such as, for example, liposarcomas,
  solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas, breast cancer (in particular breast cancer with BRCA1 mutations), etc.,
  tumors in which ACC is up regulated,
  acute and chronic myeloproliferative disorders and lymphomas, angiogenesis
  neurodegenerative disorders including Alzheimer's disease, multiple sclerosis, Parkinson's disease, epilepsy,
  erythemato-squamous dermatoses such as, for example, psoriasis,
  acne vulgaris,
  other skin disorders and dermatological conditions which are modulated by PPAR,
  eczemas and neurodermatitis,
  dermatitis such as, for example, seborrheic dermatitis or photodermatitis,
  keratitis and keratoses such as, for example, seborrheic keratoses, senile keratoses, actinic keratoses, photo-induced keratoses or keratosis follicularis,
  keloids and keloid prophylaxis,
  bacterial infections,
  fungal infections,
  warts, including condylomata or condylomata acuminata
  viral infections such as, for example, human hepatitis B virus (HBV), hepatitis C virus (HCV), West Nile virus (WNV) or Dengue virus, human Immunodeficiency virus (HIV), poxvirus and Vaccinia virus (VV), HCMV, influenza A, human papilloma viral (HPV). venereal papillomata, viral warts such as, for example, molluscum contagiosum, leukoplakia,
  papular dermatoses such as, for example, lichen planus,
  skin cancer such as, for example, basal-cell carcinomas, melanomas or cutaneous T-cell lymphomas,
  localized benign epidermal tumors such as, for example, keratoderma, epidermal naevi,
  chilblains;
  high blood pressure,
  polycystic ovary syndrome (PCOS),
  asthma,
  cystic fibrosis,
  osteoarthritis,
  lupus erythematosus (LE) or inflammatory rheumatic disorders such as, for example rheumatoid arthritis,
  vasculitis,
  wasting (cachexia),
  gout,
  ischemia/reperfusion syndrome,
  acute respiratory distress syndrome (ARDS)
  viral diseases and infections
  lipodystrophy and lipodystrophic conditions, also for treating adverse drug effect;
  myopathies and lipid myopathis (such as carnitine palmitoyltransferase I or II deficiency);
H. formation of muscles and a lean body or muscle mass formation.

The dose range of the compounds of general formula (I) applicable per day is usually from 0.001 to 10 mg per kg body weight of the patient, preferably from 0.01 to 8 mg per kg body weight of the patient. Each dosage unit may conveniently contain 0.1 to 1000 mg of the active substance, preferably it contains between 0.5 to 500 mg of the active substance.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent. According to one embodiment the additional therapeutic agent is selected from the group of therapeutic agents useful in the treatment of diseases or conditions associated with metabolic diseases or conditions such as for example diabetes mellitus, obesity, diabetic complications, hypertension, hyperlipidemia.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, agents for the treatment of malignant tumors, antithrombotic agents, agents for the treatment of heart failure and agents for the treatment of complications caused by diabetes or associated with diabetes.

Suitable anti-obesity agents include 11beta-hydroxy steroid dehydrogenase-1 (11beta-HSD type 1) inhibitors, stearoyl-CoA desaturase-1 (SCD-1) inhibitors, MCR-4 agonists, cholecystokinin-A (CCK-A) agonists, monoamine reuptake inhibitors, sympathomimetic agents, beta3 adrenergic agonists, dopamine agonists, melanocyte-stimulating hormone analogs, 5HT2c agonists, melanin concentrating hormone antagonists, leptin (the OB protein), leptin analogs, leptin agonists, galanin antagonists, lipase inhibitors, anorectic agents, neuropeptide-γ antagonists (e.g., NPY Y5 antagonists), $PY_Y3$-(including analogs thereof), thyromimetic agents, dehydroepiandrosterone or an analog thereof, glucocorticoid agonists or antagonists, orexin antagonists, glucagon-like peptide-1 agonists, ciliary neurotrophic factors, human agouti-related protein (AGRP) inhibitors, ghrelin antagonists, GOAT (Ghrelin O-Acyltransferase) inhibitors, histamine 3 antagonists or inverse agonists, neuromedin U agonists, MTP/ApoB inhibitors (e.g., gut-selective MTP inhibitors), opioid antagonists, orexin antagonists, and the like.

Preferred anti-obesity agents for use in the combination aspects of the present invention include gut-selective MTP inhibitors CCKa agonists, 5HT2c agonists, MCR4 agonists, lipase inhibitors, opioid antagonists, oleoyl-estrone, obinepitide, pramlintide (Symlin®), tesofensine (NS2330), leptin, liraglutide, bromocriptine, orlistat, exenatide (Byetta®), AOD-9604 (CAS No. 221231-10-3) and sibutramine.

Suitable anti-diabetic agents include sodium-glucose co-transporter (SGLT) inhibitors, 11beta-hydroxy steroid dehydrogenase-1 (11beta-HSD type 1) inhibitors, phosphodiesterase (PDE) 10 inhibitors, diacylglycerol acyltransferase (DGAT) 1 or 2 inhibitors, sulfonylureas (e.g., acetohexamide, chlorpropamide, diabinese, glibenclamide, glipizide, glyburide, glimepiride, gliclazide, glipentide, gliquidone, glisolamide, tolazamide, and tolbutamide), meglitinides, an alpha-amylase inhibitors (e.g., tendamistat, trestatin and AL-3688), alpha-glucoside hydrolase inhibitors (e.g., acarbose), alpha-glucosidase inhibitors (e.g., adiposine, camiglibose, emiglitate, miglitol, voglibose, pradimicin-Q, and salbostatin), PPAR gamma agonists (e.g., balaglitazone, ciglitazone, darglitazone, englitazone, isaglitazone, pioglitazone, rosiglitazone and troglitazone), PPAR alpha/gamma agonists (e.g., CLX-0940, GW-1536, GW-20 1929, GW-2433, KRP-297, L-796449, LR-90, MK-0767 and SB-219994), biguanides (e.g., metformin), GLP-1 derivatives, glucagon-like peptide 1 (GLP-1) agonists (e.g., Byetta™, exendin-3 and exendin-4), GLP-1 receptor and glucagon receptor co-agonists, glucagon receptor antagonists, GIP receptor antagonists, protein tyrosine phosphatase-1 B (PTP-1 B) inhibitors (e.g., trodusquemine, hyrtiosal extract), SIRT-1 activators (e.g. reservatrol), dipeptidyl peptidease IV (DPP-IV) inhibitors (e.g., sitagliptin, vildagliptin, alogliptin, linagliptin and saxagliptin), insulin secretagogues, GPR119 agonists, GPR40 agonists, TGR5 agonists, MNK2 inhibitors, GOAT (Ghrelin O-Acyltransferase) inhibitors, fatty acid oxidation inhibitors, A2 antagonists, c-jun amino-terminal kinase (JNK) inhibitors, insulins, insulin derivatives, fast acting insulins, inhalable insulins, oral insulins, insulin mimetics, glycogen phosphorylase inhibitors, VPAC2 receptor agonists and glucokinase activators.

Preferred anti-diabetic agents are metformin, glucagon-like peptide 1 (GLP-1) agonists (e.g., Byetta™), GLP-1 receptor and glucagon receptor co-agonists, sodium-glucose co-transporter (SGLT) inhibitors, 11beta-hydroxy steroid dehydrogenase-1 (11beta-HSD type 1) inhibitors and DPP-IV inhibitors (e.g. sitagliptin, vildagliptin, alogliptin, linagliptin and saxagliptin).

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of the acetyl-CoA carboxylase(s), in particular ACC2, in particular diseases or conditions as described hereinbefore and hereinafter.

In yet another aspect the present invention relates a method for treating, including preventing a disease or condition mediated by the inhibition of acetyl-CoA carboxylase(s) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Further aspects of the invention include the use of a compound according to the invention or a salt thereof as a crop protection agent to combat and/or prevent fungal infestations, or to control other pests such as weeds, insects, or acarids that are harmful to crops. Another aspect of the invention relates to the use of a compound according to the invention or a salt thereof for controlling and/or preventing plant pathogenic microorganisms, for example plant pathogenic fungi. Therefore one aspect of the invention is a compound according to the formula (I) or a salt thereof for use as a fungicide, insecticide, acaricide and/or herbicide. Another aspect of the invention relates to an agricultural composition comprising a compound of the present invention together with one or more suitable carriers. Another aspect of the invention relates to an agricultural composition comprising a compound of the present invention in combination with at least one additional fungicide and/or systemically acquired resistance inducer together with one or more suitable carriers.

Synthesis Schemes

Compounds of general formula (I) may be prepared by palladium-mediated Buchwald reactions or copper-mediated Ullmann reactions of aryl halogenides or aryl triflates (II) with pyrrolidines (III) wherein Z is a leaving group and denotes for example Cl, Br, I or OTf (triflate).

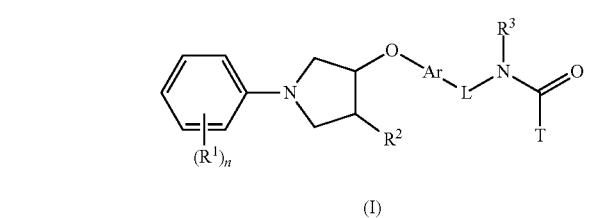

Compounds of general formula (I) may be prepared by amide coupling reactions of amines (IV) with carboxylic acids (V-I) mediated by coupling reagents such as eg 2-(1H-benzotriazol-1-yl)-1,1,3,3-tetramethyluronium tetrafluoroborat (TBTU), N-hydroxybenzotriazole (HOBt), 2-(1H-7-azabenzotriazol-1-yl)-1,1,3,3-tetramethyluronium hexafluorophosphate (HATU), (benzotriazol-1-yloxy)tripyrrolidino-phosphonium hexafluorophosphate (Pybop), benzotriazole-1-yl-oxy-tris-(dimethylamino)-phosphonium hexafluorophosphate (BOP) or 2-chloro-1,3-dimethyl-2-imidazolinium hexafluorophosphate (CIP).

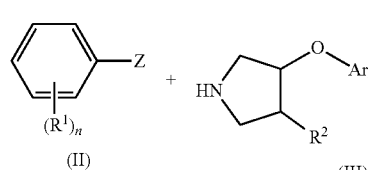

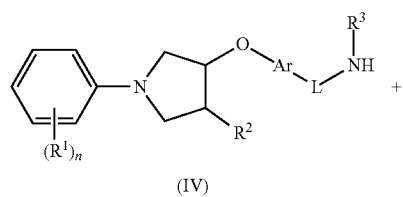

Alternatively, compounds of general formula (I) may be prepared by amide coupling reactions of amines (IV) with carboxylic acids chlorides (V-II) or carboxylic acid anhydrides (V-III).

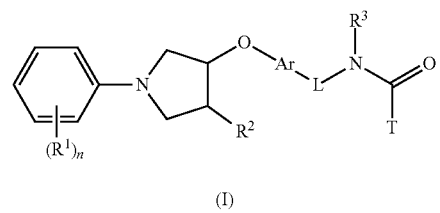

Compounds of general formula (VIII) may be prepared by alkylation reactions of aromatic alcohols (IX) with electrophiles (X) wherein Z is a leaving group which for example denotes Cl, Br, I, mesylate, tosylate or triflate and $R^6$ is $C_{1-6}$-alkyl, $C_{3-6}$-cycloalkyl, $C_{3-6}$cycloalkyl-$C_{1-2}$-alkyl, —$CH_2$— $R^4$ or heteroaryl, wherein $R^4$ and heteroaryl are as defined hereinbefore and hereinafter and the alkyl, cycloalkyl, aryl and heteroaryl groups may be optionally substituted as defined hereinbefore and hereinafter.

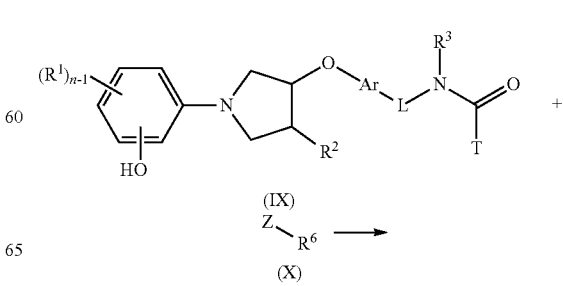

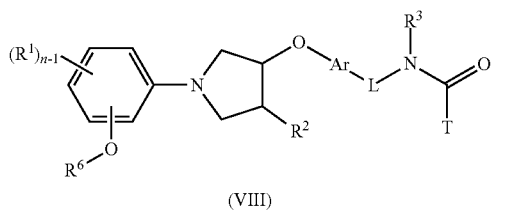

(VIII)

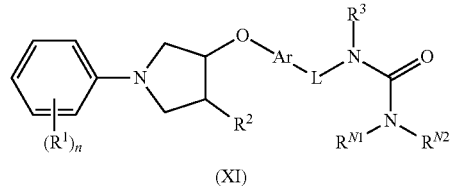

(XI)

Compounds of general formula (XI) may be prepared by urea forming reactions such as reaction of amines (IV) with amines (XII) after reaction with reagents such as N,N-carbonylditriazole (CDT) or N,N-carbonyldiimidazole (CDI). $R^{N1}$ is selected from the group consisting of H and $C_{1-3}$-alkyl, and $R^{N2}$ is selected from the group consisting of H, $C_{1-3}$-alkyl, 5-membered heteroaryl group containing 1 to 3 heteroatoms selected independently from O, S, N and NH, wherein said heteroaryl group is optionally substituted with $C_{1-3}$-alkyl.

Compounds of general formula (XV), wherein $R^8$ is $C_{1-2}$-alkyl, may be prepared by urethane forming reactions such as reaction of amines (IV) with alcohols (XVI) after reaction with reagents such as CDT or CDI. Alcohols may be used in their deprotonated form.

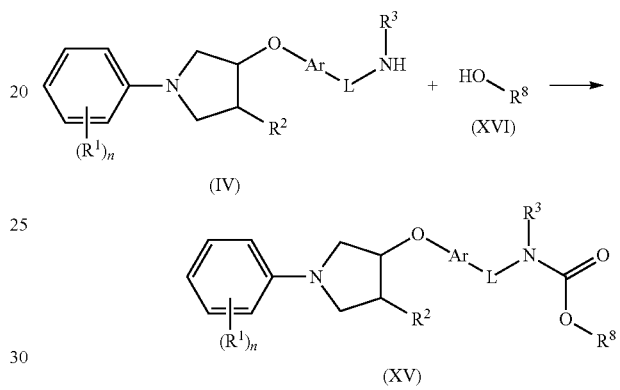

Alternatively, compounds of general formula (XV) may be prepared by urethane forming reactions such as reaction of amines (IV) with chloro formates (XXI).

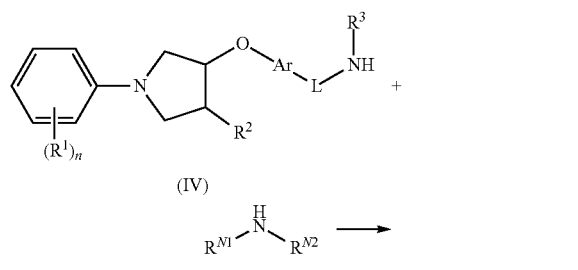

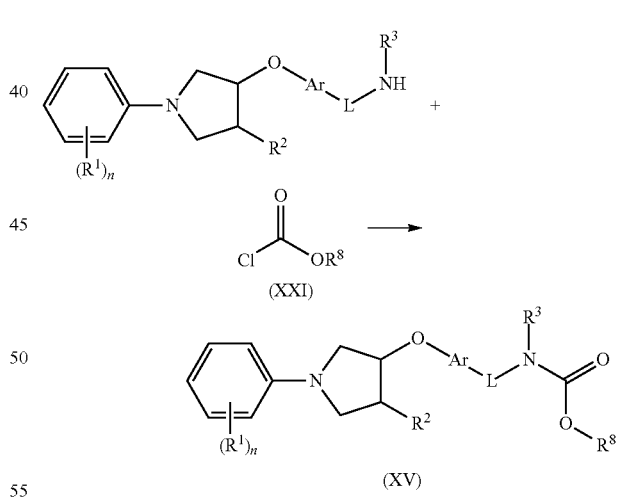

Alternatively, compounds of general formula (XI) may be prepared by urea forming reactions such as reaction of amines (IV) with carbamoyl chlorides (XIII) or isocyanates (XIV).

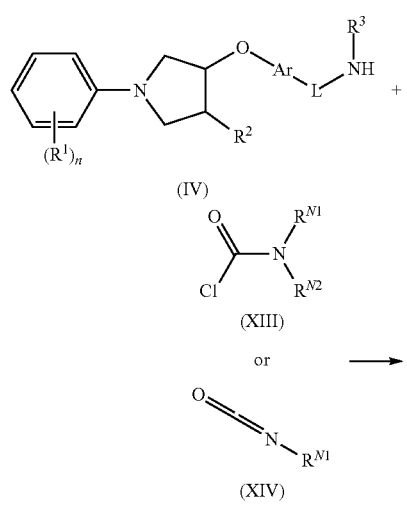

EXAMPLES

The Examples that follow are intended to illustrate the present invention without restricting it. The terms "ambient temperature" and "room temperature" are used interchangeably and designate a temperature of about 20° C.

Preliminary Remarks:

As a rule, 1H-NMR and/or mass spectra have been obtained for the compounds prepared. The $R_f$ values are determined using silica gel plates and UV light at 254 nm.

To describe the relative configuration of stereogenic centers straight bars are used. To describe the relative and absolute configuration, the bars have a wedged shape. reality configuration:

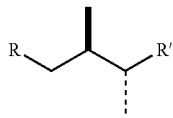

relative and absolute configuration:

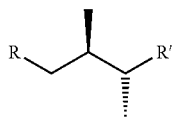

ABREVIATIONS

| | |
|---|---|
| aq. | aqueous |
| ACN | acetonitrile |
| AcOH | acetic acid |
| BOC | tert-butoxy-carbonyl- |
| BOP | benzotriazole-1-yl-oxy-tris-(dimethylamino)-phosphonium hexafluorophosphate |
| CDI | N,N-carbonyldiimidazole |
| CDT | N,N-carbonylditriazole |
| CIP | 2-chloro-1,3-dimethyl-2-imidazolinium hexafluorophosphate |
| CyH | cyclohexane |
| DAST | diethylaminosulfur trifluoride |
| DBAD | di-tert-butyl azodicarboxylate |
| DCM | dichloro methane |
| DIAD | diisopropyl azodicarboxylate |
| DIPE | diisopropyl ether |
| DIPEA | N,N-diisopropylethylamine |
| DMA | dimethylacetamide |
| DMAP | 4-dimethylaminopyridine |
| DMF | N,N-dimethylformamide |
| DMSO | dimethyl sulfoxide |
| dppf | diphenylphosphino ferrocene |
| EtOAc | ethyl acetate |
| EtOH | ethanol |
| Ex | example |
| FA | formic acid |
| HATU | 2-(1H-7-azabenzotriazol-1-yl)-1,1,3,3-tetramethyl-uronium hexafluorophosphate |
| MeOH | methanol |
| Ms | methanesulfonyl |
| n.d. | not determined |
| NMP | N-methyl-2-pyrrolidone |
| Pd/C | palladium on activated carbon |
| PE | petroleum ether |
| PG | protecting group |
| Pybop | (benzotriazol-1-yloxy)tripyrrolidinophosphonium hexafluorophosphate |
| r.t. | room temperature (about 20° C.) |
| sat. | saturated |
| TBME | tert-butyl methyl ether |
| TEA | triethylamine |
| TF/TFA | trifluoroacetic acid |
| THF | tetrahydrofuran |
| TBTU | 2-(1H-benzotriazol-1-yl)-1,1,3,3-tetramethyluronium tetrafluoroborate |
| TMS | trimethylsilyl |
| TPP | triphenylphosphine |
| Ts | 4-toluenesulfonyl |
| X-Phos | 2-dicyclohexylphosphino-2',4',6'-tri-isopropyl-1,1'-biphenyl |

Preparation of Starting Compounds

Example I (S)—N-(1-(4-Bromophenyl)ethyl)acetamide

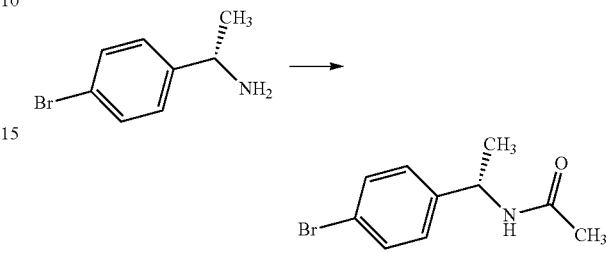

To 200 g (1.00 mol) (S)-1-(4-bromophenyl)ethylamine in 800 ml DCM are slowly added 94.5 mL (1.00 mol) acetic anhydride while cooling the mixture to 20-30° C. After that the cooling is removed and the reaction mixture is stirred at r.t. over night. Afterwards the mixture is consecutivly washed with water, sat. aq. NaHCO$_3$ solution, water, diluted aq. citric acid solution and water once again. The org. layer is dried over MgSO$_4$ and the solvent is removed in vacuo. The crude product is used without further purification.

$C_{10}H_{12}BrNO$ (M=242.1 g/mol)

ESI-MS: 242/244 [M+H]$^+$

R$_t$ (HPLC): 1.67 min (method A)

Example II (S)-tert-Butyl 1-(4-bromophenyl)ethylcarbamate

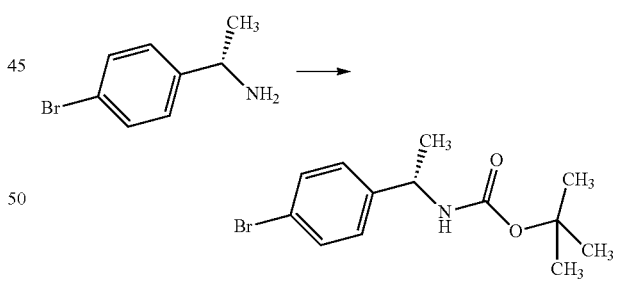

To 150 g (735 mmol) (S)-1-(4-bromophenyl)ethylamine in 2 L DCM are added 459 mL (918 mmol) of an aq. Na$_2$CO$_3$ solution (c=2 mol/L). To this mixture a solution of 164 g (749 mmol) BOC$_2$O in 350 mL THF is added dropwise at r.t. and stirring is continued for 1 h. After that the mixture is poured onto water and stirred for additional 20 min. The layers are separated, the org. layer is washed with water (2×), dried over Na$_2$SO$_4$ and the solvent is removed in vacuo.

$C_{13}H_{18}BrNO_2$ (M=300.2 g/mol)

ESI-MS: 300/302 [M+H]$^+$

R$_f$ (TLC): 0.90 (silica gel, DCM/MeOH 9/1)

Example III

Example III.1

General Route

N-[1-(4-Bromo-3-fluoro-phenyl)-ethyl]-acetamide

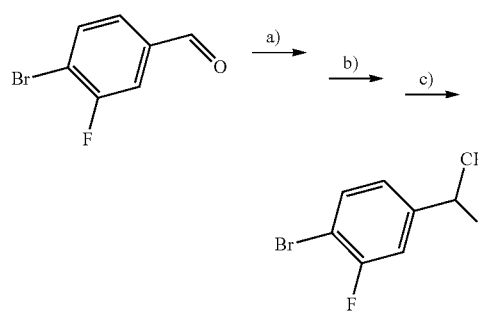

a) 11.1 g (91.0 mmol) 2-Methyl-2-propanesulfinamide are added to 16.5 g (76.0 mmol) 4-bromo-3-fluoro-benzaldehyde and 34.6 g (152 mmol) titanium(IV) ethoxide in 100 mL THF. Stirring is continued for 1.5 h at 50° C. After that time, the mixture is poured into brine. The mixture is filtered over celite and the filtrate is transferred to a separation funnel. The organic layer is separated, dried over magnesium sulphate and the solvent is removed by evaporation. The residue is purified by column chromatography (silica gel; gradient hexane/EtOAc 1:0→3:2) to yield the desired product.

$C_{11}H_{13}BrFNOS$ (M=306.2 g/mol),
ESI-MS: 306/308 [M+H]$^+$
$R_f$ (TLC): 0.30 (silica gel, hexane/EtOAc 4:1)

b) Under inert gas atmosphere 37.2 mL (112 mmol) of a 3N solution of methyl magnesium bromide in THF are added dropwise to 17.1 g (55.8 mmol) 2-methyl-propane-2-sulfonic acid 4-bromo-3-fluoro-benzylideneamide (IX.1) in 170 mL THF at −78° C. The cooling bath is removed and stirring is continued for 2 h. After that time, the mixture is poured into sat. NH$_4$Cl-solution (300 mL) and extracted with EtOAc. The organic layer is separated, washed with brine and dried over sodium sulphate. The solvent is removed by evaporation to yield the desired product.

$C_{12}H_{17}BrFNOS$ (M=322.2 g/mol)
ESI-MS: 322/324 [M+H]$^+$ c) 20.0 mL 4N HCl in dioxane are added to 17.2 g (53.4 mmol) 2-methyl-propane-2-sulfonic acid [1-(4-bromo-3-fluoro-phenyl)-ethyl]-amide (X.1) in 150 mL MeOH. Stirring is continued for 1 h. After that time, the mixture is concentrated and the residue is triturated from diethylether (150 mL). The precipitate is filtered off, washed with diethylether and suspended in 250 mL DCM. 8.64 mL (107 mmol) pyridine and 5.29 mL (56.1 mmol) acetic anhydride are added and the mixture is stirred for 12 h at rt. After that time, the mixture is transferred to a separation funnel, washed with 1N HCl (200 mL) and sat. aq. NaHCO$_3$-solution (200 mL) and dried over sodium sulphate. The solvent is removed by evaporation to yield the desired product.

$C_{10}H_{11}BrFNO$ (M=260.1 g/mol)
ESI-MS: 260/262 [M+H]$^+$
$R_t$ (HPLC): 2.60 min (method F)

The following compounds are prepared analogously to example III.1

| Ex. | Starting material | Product structure | Mass spec result | HPLC retention time (method) |
|---|---|---|---|---|
| III.1 | 4-bromo-3-fluoro-benzaldehyde | N-[1-(4-bromo-3-fluoro-phenyl)-ethyl]-acetamide | 260/262 [M + H]$^+$ | 2.60 (F) |
| III.2 | 4-bromo-2-fluoro-benzaldehyde | N-[1-(4-bromo-2-fluoro-phenyl)-ethyl]-acetamide | 260/262 [M + H]$^+$ | 2.60 (F) |
| III.3 | 6-bromo-pyridine-3-carbaldehyde | N-[1-(6-bromo-pyridin-3-yl)-ethyl]-acetamide | 243/245 [M + H]$^+$ | 1.28 (G) |

Example IV

Example IV.1

General Route (S)—N-(1-(4-Hydroxyphenyl)ethyl)acetamide

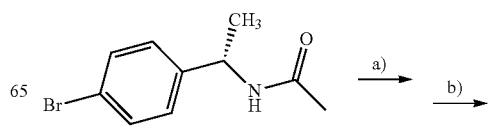

-continued

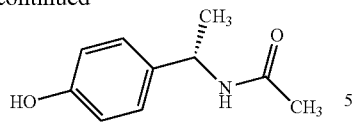

a) To a mixture of 60.0 g (248 mmol) of example 1, 73.0 g (743 mmol) KOAc, 94.4 g (372 mmol) bis(pinakolato)diboron and 3.62 g (4.96 mmol) PdCl$_2$(dppf) in an atmosphere of argon is added 450 mL DMSO and the resulting mixture is degassed twice and stirred at 80° C. for 3 h. After that the reaction mixture is chilled to r.t. diluted with water and EtOAc and the layers are separated. The aq. layer is extracted with EtOAc (2×). The org. layers are combined, washed with water (3×), dried over MgSO$_4$, filtered through a plug of Celite® and the solvent is removed in vacuo. The crude product is used without further purification.

C$_{16}$H$_{24}$BNO$_3$ (M=289.2 g/mol)
ESI-MS: 290 [M+H]$^+$
R$_t$ (HPLC): 1.19 min (method B)

b) 80.0 g (0.18 mol) of the above mentioned product is added to 500 ml THF and chilled to 0° C. 31.8 ml (0.36 mmol) H$_2$O$_2$ (35% in water) and subsequently 51.7 ml (0.16 mmol) 4N aq. NaOH solution are added and the resulting mixture is stirred for 2 h. EtOAc is added and the mixture is extracted with 1N aq. NaOH solution (2×). The org. layer is washed with EtOAc, acidified with citric acid and extracted with EtOAc (3×). The org. layers are combined, washed with a Na$_2$S$_2$O$_3$ solution (10% in water), dried over Na$_2$SO$_4$, filtered and the solvent is removed in vacuo. The resulting product is triturated with TBME.

C$_{10}$H$_{13}$NO$_2$ (M=179.2 g/mol)
ESI-MS: 180 [M+H]$^+$
R$_t$ (HPLC): 0.30 min (method C)

The following compounds are prepared analogously to example IV.1

Example V

N-[1-(4-Hydroxy-3-fluoro-phenyl)-ethyl]-acetamide

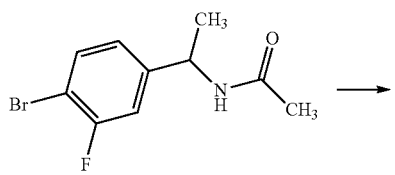

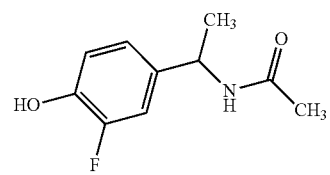

Under inert gas atmosphere 200 mg (0.77 mmol) of example III are added to a 1/1 mixture of dioxane and water. Then 240 mg (4.20 mmol) powdered KOH and 58.7 mg (0.12 mmol) 2-di-tert-butylphosphino-3,4,5,6-tetramethyl-2',4',6'-triisopropyl-1,1'-biphenyl are added and the mixture is degassed before 36.6 mg (0.04 mmol) Pd$_2$(dba)$_3$ are added and the mixture is stirred at 140° C. for 10 min in a microwave oven. After cooling down, the reaction mixture is diluted with EtOAc, washed with an aq. HCl solution (c=4 mol/L) and a sat. aq. NaCl solution, dried over MgSO$_4$, filtered and the solvent is removed in vacuo. The resulting crude product is purified by HPLC (ACN/H$_2$O/TFA).

C$_{10}$H$_{12}$FNO$_2$ (M=197.2 g/mol)
ESI-MS: 198 [M+H]$^+$
R$_t$ (HPLC): 0.55 min (method D)

| Ex. | Starting material | Product structure | Mass spec result | HPLC retention time (method) |
|---|---|---|---|---|
| IV.1 | 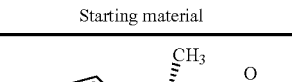 | 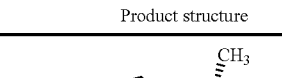 | 180 [M + H]$^+$ | 0.30 (C) |
| IV.2 | 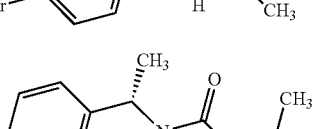 | 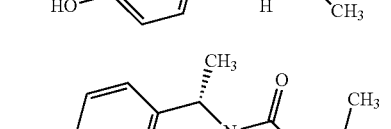 | 238 [M + H]$^+$ | 1.58 (A) |
| IV.3 | 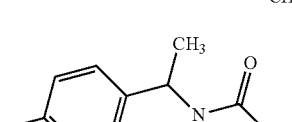 | 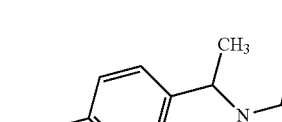 | 198 [M + H]$^+$ | 0.62 (E) |

Example VI (S)—N-(1-(5-Hydroxypyridin-2-yl)ethyl)acetamide

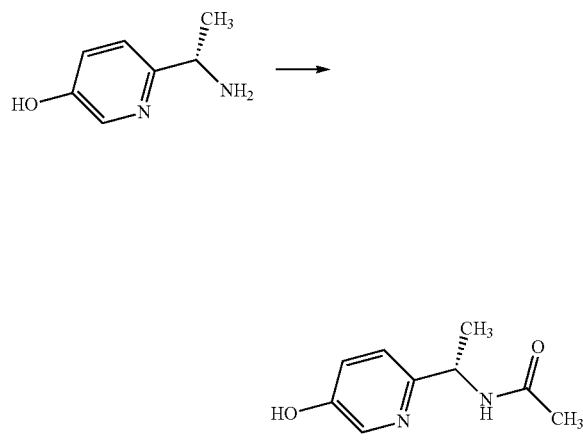

To 1.00 g (5.73 mmol) (S)-6-(1-aminoethyl)pyridin-3-ol in 10 ml THF and 3.99 mL TEA (28.6 mmol) are slowly added 494 mg (6.30 mmol) acetyl chloride and stirring is continued for 2 h. The reaction is quenched by the addition of water and extracted several times with DCM. The org. layers are combined, dried over MgSO$_4$, filtered and the solvent is removed in vacuo. The crude product is purified by column chromatography (silica gel, DCM/MeOH/NH$_3$ 90/9/1).

$C_9H_{12}N_2O_2$ (M=180.2 g/mol)
ESI-MS: 181 [M+H]$^+$
R$_t$ (HPLC): 0.15 min (method E)

Example VII

Example VII.1

General Route (R)-tert-Butyl 3-(4-((S)-1-acetamidoethyl)phenoxy)pyrrolidine-1-carboxylate

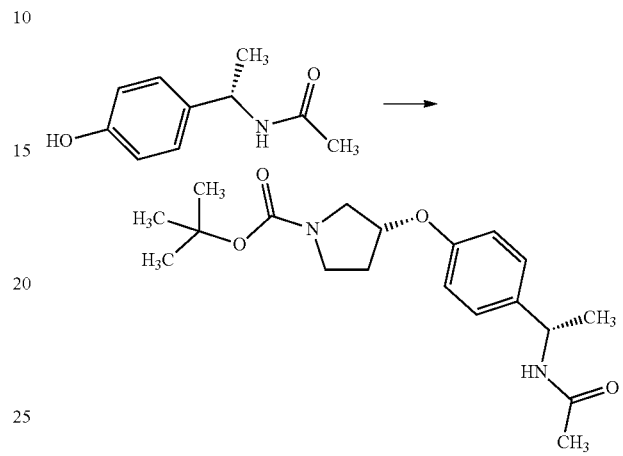

20.0 g (75.4 mmol) (S)-tert-Butyl 3-(methylsulfonyloxy)-pyrrolidine-1-carboxylate, 13.5 g (75.4 mmol) of example IV.1 and 49.1 g (151 mmol) Cs$_2$CO$_3$ are added to 150 mL DMF and stirred at 80° C. Then the reaction mixture is chilled to r.t., diluted with water and extracted with EtOAc (2×). The org. layers are combined, washed with aq. NaHCO$_3$ solution (3×) and dried over MgSO$_4$. After filtration the solvent is removed in vacuo and the crude product is purified by flash chromatography (silica gel, DCM/MeOH 93/7).

$C_{19}H_{28}N_2O_4$ (M=348.4 g/mol)
ESI-MS: 349 [M+H]$^+$
R$_t$ (HPLC): 1.02 min (method C)

The following compounds are prepared analogously to example VII.1

| Ex. | Starting material(s) | Product structure | Mass spec result | HPLC retention time (method) |
|---|---|---|---|---|
| VII.1 | IV.1 + [tert-butyl 3-(methylsulfonyloxy)pyrrolidine-1-carboxylate, (S)] | [(R)-tert-butyl 3-(4-((S)-1-acetamidoethyl)phenoxy)pyrrolidine-1-carboxylate] | 349 [M+H]$^+$ | 1.02 (C) |
| VII.2 | IV.1 + [tert-butyl 3-(methylsulfonyloxy)pyrrolidine-1-carboxylate, (R)] | [(S)-tert-butyl 3-(4-((S)-1-acetamidoethyl)phenoxy)pyrrolidine-1-carboxylate] | 349 [M+H]$^+$ | 2.15 (A) |

| Ex. | Starting material (s) | Product structure | Mass spec result | HPLC retention time (method) |
|---|---|---|---|---|
| VII.3 | IV.2 + [structure: N-Boc-pyrrolidinyl methanesulfonate] | [structure: Cbz-pyrrolidinyl-O-phenyl-ethyl-NHBoc] | 441 [M + H]+ | 1.22 (C) |

*A representative procedure for the preparation of N-protected 3-methylsulfonyloxy-pyrrolidines can be found in Zersh et al., Synthesis 2011, 22, 3669-3674.

Example VIII

Example VIII.1

General Route

N—((S)-1-(4-((R)-Pyrrolidin-3-yloxy)phenyl)ethyl) acetamide hydrochloride

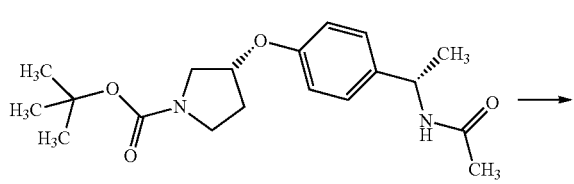

To 20.5 g (58.8 mmol) of example VII.1 in 200 mL dioxane are added 29.4 mL (118 mmol) HCl in dioxane (c=4 mol/L) and the resulting mixture is stirred ar r.t. over night. Additional 15 mL (60 mmol) HCl in dioxane (c=4 mol/L) are added and stirring is continued for 1 d. Then the reaction mixture is treated with TBME and the precipitate is filtered, washed with TBME and dried at 40° C. in vacuo.

$C_{14}H_{20}N_2O_2$*HCl (M=284.8 g/mol)

ESI-MS: 249 [M+H]+

$R_t$ (HPLC): 0.63 min (method C)

The following compounds are prepared analogously to example VIII.1

For example VIII.3 the resulting product VIII.1 is treated with aq. NaOH solution and extracted with DCM (2×), the org. layers are combined, dried over MgSO₄, filtered and the solvent is removed in vacuo.

| Ex. | Starting material | Product structure | Mass spec result | HPLC retention time (method) |
|---|---|---|---|---|
| VIII.1 | VII.1 | [structure with HCl salt] | 249 [M + H]+ | 0.63 (C) |
| VIII.2 | VII.2 | [structure with HCl salt] | 249 [M + H]+ | 1.30 (A) |
| VIII.3 | VII.1 | [free base structure] | 249 [M + H]+ | 0.63 (C) |

Example IX (R)-Benzyl 3-(4-((S)-1-aminoethyl)phenoxy)pyrrolidine-1-carboxylate hydrochloride

Example X

Example X.1

General Route (R)-Benzyl 3-(4-((S)-1-(thiazole-5-carboxamido)ethyl)phenoxy)pyrrolidine-1-carboxylate

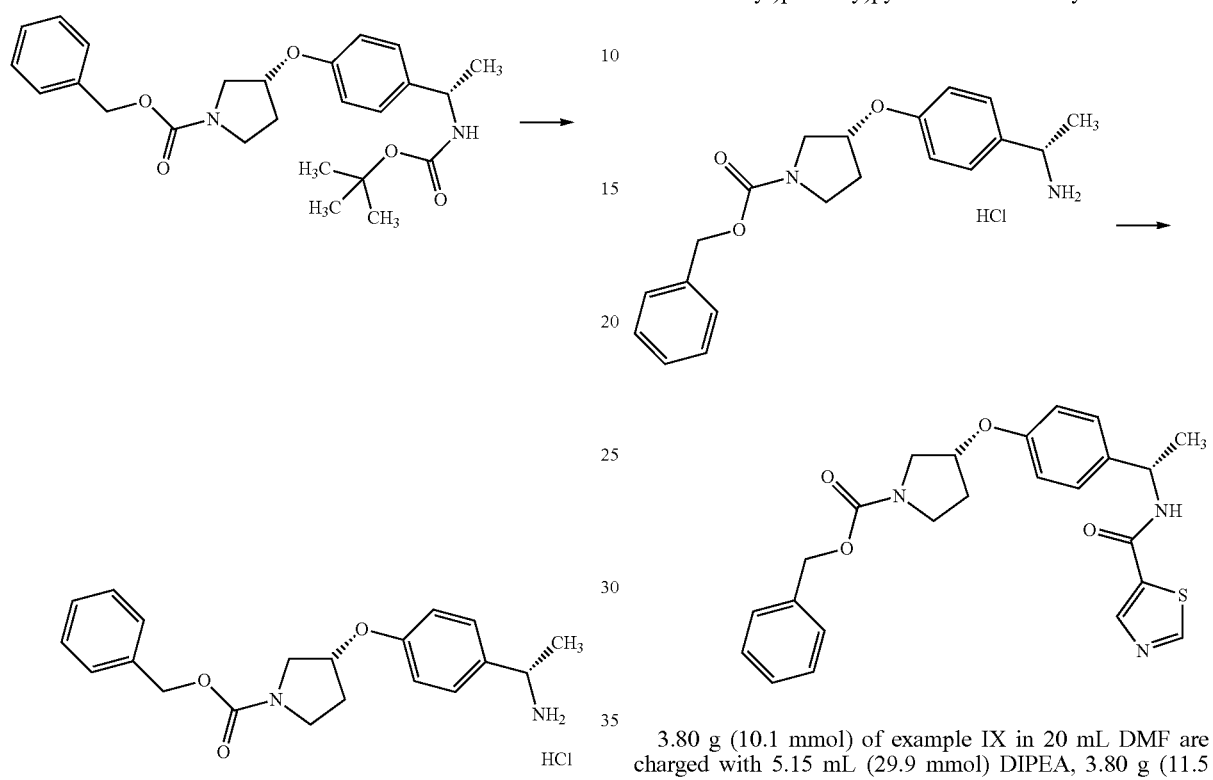

4.70 g (10.7 mmol) of example VII.3 in 25 mL dioxane are charged with 5.33 mL (21.3 mmol) of a HCl solution in dioxane (c=4 mol/L) and stirred at r.t. over night. The solvent is removed in vacuo and the residue is taken up in ethanol and the solvent is removed again. The resulting product is triturated with DIPE and dried at 50° C.

$C_{20}H_{24}N_2O_3$*HCl (M=376.9 g/mol)
ESI-MS: 324 [M+H—$NH_3$]$^+$
$R_t$ (HPLC): 1.07 min (method C)

3.80 g (10.1 mmol) of example IX in 20 mL DMF are charged with 5.15 mL (29.9 mmol) DIPEA, 3.80 g (11.5 mmol) TBTU and finally after 10 min with 1.29 g (9.99 mmol) thiazole-5-carboxylic acid. The reaction mixture is stirred at r.t. over night. The next day water is added and the mixture is extracted with EtOAc (3×). The organic layers are combined, dried over $MgSO_4$, filtered and the solvent is removed in vacuo. The crude product is purified by flash chromatography (silica gel, EtOAc). Then the product is added to EtOAc and washed with a saturated aq. $NaHCO_3$ solution (3×), dried over $MgSO_4$, filtered and the solvent is removed in vacuo.

$C_{24}H_{25}N_3O_4S$ (M=451.5 g/mol)
ESI-MS: 452 [M+H]$^+$
$R_t$ (HPLC): 0.92 min (method D)

The following compounds are prepared analogously to example X.1

| Ex. | Starting material | Product structure | Mass spec result | HPLC retention time (method) |
|---|---|---|---|---|
| X.1 | IX | | 452 [M + H]$^+$ | 0.92 (D) |

-continued

| Ex. | Starting material | Product structure | Mass spec result | HPLC retention time (method) |
|---|---|---|---|---|
| X.2 | IX | 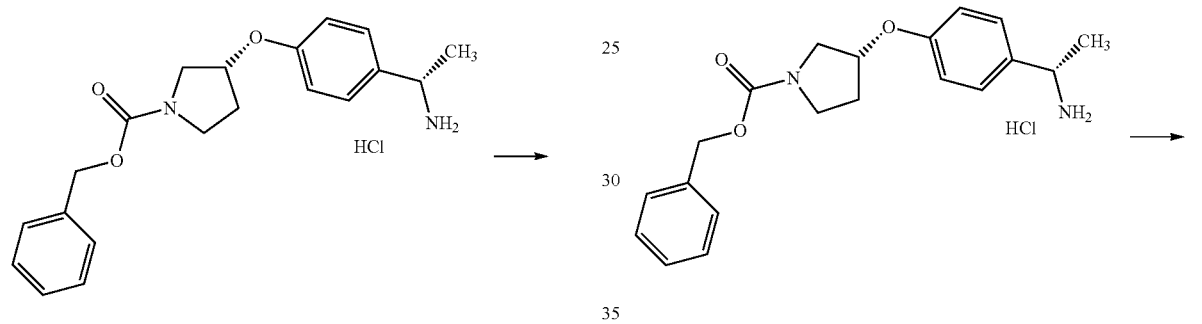 | 523 [M + H]⁺ | 1.08 (C) |

Example XI (R)-Benzyl 3-(4-((S)-1-(cyclopropanecarboxamido)ethyl)phenoxy)pyrrolidine-1-carboxylate Example XII (R)-Benzyl 3-(4-((S)-1-(3,3-dimethylureido)ethyl)phenoxy)pyrrolidine-1-carboxylate

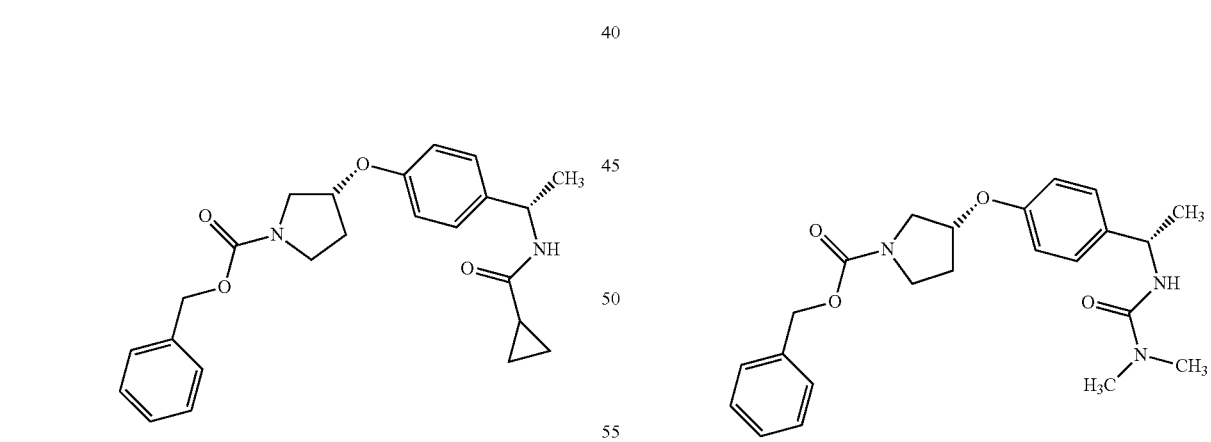

To 3.79 g (10.1 mmol) of example IX in 50 mL DCM together with 5.00 mL (35.9 mmol) TEA are slowly added 1.10 mL (11.9 mmol) cyclopropanecarbonyl chloride dissolved in 10 mL DCM. After stirring the mixture for 3 h at r.t., the mixture is washed with water, dried over MgSO$_4$, filtered and the solvent is removed in vacuo. The resulting product is triturated with DIPE and dried at 50° C.

$C_{24}H_{28}N_2O_4$ (M=408.5 g/mol)

ESI-MS: 409 [M+H]⁺

$R_t$ (HPLC): 1.25 min (method E)

To 2.00 g (5.31 mmol) of example IX and 1.86 mL (13.3 mmol) TEA in 40 mL DCM are added 914 mg (5.57 mmol) CDT and the resulting mixture is stirred at r.t. for 15 min. After that 716 mg (15.9 mmol) dimethylamine are added and stirring is continued over night. Finally the solvent is removed in vacuo and the crude product is purified by HPLC (MeOH/H$_2$O/NH$_3$).

$C_{23}H_{29}N_3O_4$ (M=411.5 g/mol)

ESI-MS: 412 [M+H]⁺

$R_t$ (HPLC): 1.05 min (method C)

Example XIII

Example XIII.1

General Route tert-Butyl (S-1-(4-((R)-pyrrolidin-3-yloxy)phenyl)ethyl)carbamate

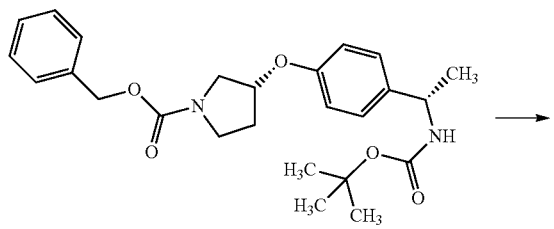

15.0 g (34.1 mmol) of example VII.3 in 200 mL methanol are hydrogenated at r.t. using 1.50 g Pd/C (10%) and a hydrogen pressure of 3 bar. After completion the reaction mixture is filtered and the solvent is removed in vacuo.

$C_{17}H_{26}N_2O_3$ (M=306.4 g/mol)

ESI-MS: 307 [M+H]$^+$ $R_t$ (HPLC): 1.01 min (method C)

The following compounds are prepared analogously to example XIII.1

For example X.2 the resulting product is transferred into the hydrochloride salt using a methanolic HCl solution (c=1.25 mol/L).

| Ex. | Starting material | Product structure | Mass spec result | HPLC retention time (method) |
|---|---|---|---|---|
| XIII.1 | IV.3 | | 307 [M + H]$^+$ | 1.01 (C) |
| XIII.2 | XI | | 275 [M + H]$^+$ | 0.68 (E) |
| XIII.3 | XII | | 278 [M + H]$^+$ | 0.68 (C) |

Example XIV

Example XIV.1

General Route

2-Acetamido-4-methyl-N—((S)-1-(4-((R)-pyrrolidin-3-yloxy)phenyl)ethyl)thiazole-5-carboxamide

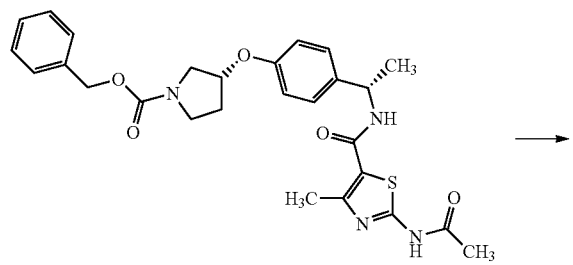

→

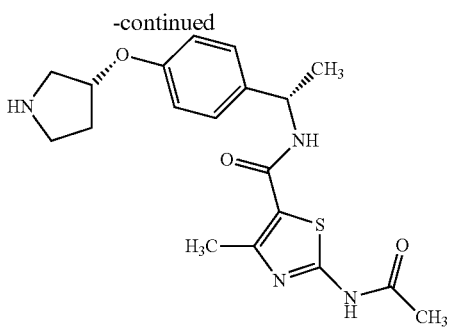

2.00 g (3.83 mmol) of example X.2 in 50 mL ACN are chilled by using an ice bath and charged with 2.60 mL (19.1 mmol) TMSI. The cooling bath is removed and the mixture is stirred at r.t. for 1 h. The reaction is quenched by addition of some water. Solvent is removed and the crude product is purified by HPLC (MeOH/H$_2$O/NH$_3$). $C_{19}H_{24}N_4O_3S$ (M=388.5 g/mol)

ESI-MS: 389 [M+H]$^+$

R$_t$ (HPLC): 0.77 min (method C)

The following compounds are prepared analogously to example XIV.1

| Ex. | Starting material | Product structure | Mass spec result | HPLC retention time (method) |
|---|---|---|---|---|
| XIV.1 | X.2 | | 389 [M + H]$^+$ | 0.77 (C) |
| XIV.2 | X.1 | | 318 [M + H]$^+$ | 0.55 (D) |

Example XV (3R)-tert-Butyl 3-(5-(1-acetamidoethyl)pyridin-2-yloxy)pyrrolidine-1-carboxylate

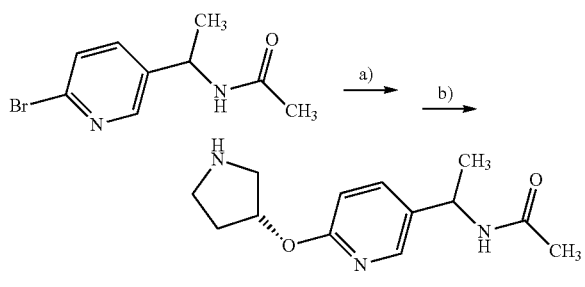

a) To a mixture of 150 mg (0.62 mmol) of example III.3 and 150 mg (0.80 mmol) of (R)-3-hydroxy-pyrrolidine-1-carboxylic acid tert-butyl ester in 6 mL dioxane are added 37.0 mg (0.93 mmol) NaH and the resulting mixture is stirred at 80° C. for 4 d. After cooling down to r.t. water is added and the mixture is extracted with EtOAc (2×). The org. layers are combined, dried over MgSO$_4$, filtered and the solvent is removed in vacuo. The crude product is purified by HPLC (MeOH/H$_2$O/NH$_3$).

$C_{18}H_{27}N_3O_4$ (M=349.4 g/mol)
ESI-MS: 350 [M+H]$^+$
R$_t$ (HPLC): 1.45 min (method C)

b) 140 mg (0.40 mmol) of the above mentioned product is added to 5 ml MeOH and charged with 0.80 mL (1.00 mmol) of an methanolic HCl solution (c=1.3 mol/L). After stirring over night at r.t. additional 0.60 mL (0.78 mmol) of the methanolic HCl solution are added and stirring is continued for 24 h. Then the solvent is removed in vacuo and the residue is purified by HPLC (MeOH/H$_2$O/NH$_3$).

$C_{13}H_{19}N_3O_2$ (M=249.3 g/mol)
ESI-MS: 250 [M+H]$^+$
R$_t$ (HPLC): 0.56 min (method C)

Example XVI

Example XVI.1

General Route

1-Bromo-4-cyclopropylmethoxybenzene

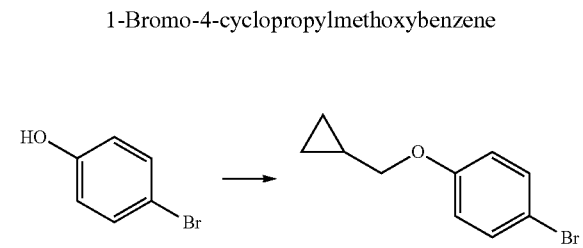

5.0 g (28.9 mmol) 4-bromophenol, 3.93 g (43.4 mmol) (chloromethyl)cyclopropane and 7.99 g (57.8 mmol) K$_2$CO$_3$ are added to 10 mL DMF and stirred at 80° C. over night. Afterwards the reaction mixture is diluted with water and extracted with DCM. The organic layer is dried over MgSO$_4$ and the solvent is removed in vacuo.

$C_{10}H_{11}BrO$ (M=227.1 g/mol)
EI-MS: 226/228 [M]$^+$
R$_t$ (HPLC): 1.20 min (method C)

The following compounds are prepared analogously to example XVI.1

For example XVI.2 and XVI.24 the reaction temperature is 120° C.

For the examples XVI.17-23 and XVI.3132 ACN is used as solvent.

The example XVI.30 can be prepared also by using Mitsunobu conditions (2,2-difluorocyclopropylmethanol, appropriate phenol, DIAD, TPP; THF, r.t. over night)

| Ex. | Starting material | Starting material | Product structure | Mass spec result | HPLC retention time (method) |
|---|---|---|---|---|---|
| XVI.1 | ![HO-C6H4-Br] | ![cyclopropyl-CH2-Cl] | ![cyclopropyl-CH2-O-C6H4-Br] | 226/228 [M]$^+$ | 1.20 (C) |
| XVI.2 | ![HO-C6H4-Br] | ![cyclobutyl-Br] | ![cyclobutyl-O-C6H4-Br] | 226/228 [M]$^+$ | 1.39 (H) |
| XVI.3 | ![HO-C6H3(F)-Br] | ![cyclopropyl-CH2-Cl] | ![cyclopropyl-CH2-O-C6H3(F)-Br] | 244/246 [M]$^+$ | 2.08 (A) |
| XVI.4 | ![HO-C6H3(F)-Br] | ![H3C-CH2-Br] | ![H3C-CH2-O-C6H3(F)-Br] | 218/220 [M]$^{+-}$ | 2.17 (A) |

| Ex. | Starting material | Starting material | Product structure | Mass spec result | HPLC retention time (method) |
|---|---|---|---|---|---|
| XVI.5 | | | | 231/233 [M + H]⁺ | 2.00 (A) |
| XVI.6 | | | | 244/246 [M]⁺ | 2.12 (A) |
| XVI.7 | | | | 257/259 [M + NH₄]⁺ | 2.27 (A) |
| XVI.8 | | | | n.d. | TLC: $R_f$ = 0.9 PE/EtOAc 8/2 |
| XVI.9 | | | | 262/264 [M]⁺ | 1.15 (C) |
| XVI.10 | | | | n.d. | 1.03 (C) |
| XVI.11 | | | | n.d. | TLC: $R_f$ = 0.49 CyH/EtOAc 9/1 |
| XVI.12 | | | | 248/250 [M]⁺ | 1.04 (C) |
| XVI.13 | | | | 280/282 [M]⁺ | 1.32 (H) |
| XVI.14 | | | | n.d. | 1.20 (H) |
| XVI.15 | | | | 293/295 [M + H]⁺ | 1.27 (H) |

-continued

| Ex. | Starting material | Starting material | Product structure | Mass spec result | HPLC retention time (method) |
|---|---|---|---|---|---|
| XVI.16 | 5-hydroxy-2-bromobenzonitrile | H₃C-CH₂-Br | 5-ethoxy-2-bromobenzonitrile | 226/228 [M + H]⁺ | 1.82 (A) |
| XVI.17 | 4-bromophenol | 1-fluoro-3-iodopropane | 1-(3-fluoropropoxy)-4-bromobenzene | n.d. | 1.18 (C) |
| XVI.18 | 4-bromophenol | (S)-3-iodotetrahydrofuran | (S)-3-(4-bromophenoxy)tetrahydrofuran | n.d. | 1.08 (C) |
| XVI.19 | 4-bromophenol | [1-(trifluoromethyl)cyclopropyl]methyl methanesulfonate | 1-{[1-(trifluoromethyl)cyclopropyl]methoxy}-4-bromobenzene | 294/296 [M + H]⁺ | 1.24 (C) |
| XVI.20 | 4-bromo-3-methylphenol | 2-bromopropane | 4-bromo-3-methyl-1-isopropoxybenzene | 228/230 [M + H]⁺ | 1.34 (C) |
| XVI.21 | 4-bromo-3-methylphenol | H₃C-CH₂-Br | 4-bromo-3-methyl-1-ethoxybenzene | 214/216 [M + H]⁺ | 1.33 (C) |
| XVI.22 | 4-bromo-3-methylphenol | 1-fluoro-3-iodopropane | 4-bromo-3-methyl-1-(3-fluoropropoxy)benzene | 246/248 [M + H]⁺ | 1.29 (C) |
| XVI.23 | 4-bromo-3-methylphenol | (bromomethyl)cyclopropane | 4-bromo-3-methyl-1-(cyclopropylmethoxy)benzene | 240/242 [M + H]⁺ | 1.36 (C) |
| XVI.24 | 4-bromo-3-methylphenol | 1-bromopropane | 4-bromo-3-methyl-1-propoxybenzene | n.d. | 2.31 (A) |
| XVI.25 | 4-bromophenol | 2,2-difluoropropyl tosylate | 1-(2,2-difluoropropoxy)-4-bromobenzene | 250/252 [M + H]⁺ | 0.97 (K) |
| XVI.26 | 4-iodophenol | (chloromethyl)cyclopropane | 1-(cyclopropylmethoxy)-4-iodobenzene | 274 [M]⁺ | 1.23 (C) |

-continued

| Ex. | Starting material | Starting material | Product structure | Mass spec result | HPLC retention time (method) |
|---|---|---|---|---|---|
| XVI.27 | HO-C6H4-Br | (CH3)2C(F)CH2Br | (CH3)2C(F)CH2-O-C6H4-Br | n.d. | 1.15 (C) |
| XVI.28 | HO-C6H4-I | 3,3-difluorocyclobutyl-CH2-OTs | cyclopropyl-CH2-O-C6H4-I | 299 [M + Na]+ | 0.92 (K) |
| XVI.29 | HO-C6H4-Br | (3R)-tetrahydrofuran-3-yl OTs | tetrahydrofuran-3-yl-O-C6H4-Br | 242/244 [M*]+ | 3.79 (V) |
| XVI.30 | HO-C6H3(F)-Br | 2,2-difluorocyclopropyl-CH2Br | 2,2-difluorocyclopropyl-CH2-O-C6H3(F)-Br | n.d. | 1.15 (D) |
| XVI.31 | HO-C6H3(F)-Br | 2,2-difluorocyclopropyl-CH2Br | H3C-CH2-O-C6H3(F)-Br | n.d. | 1.14 (D) |
| XVI.32 | HO-C6H3(F)-Br | cyclopropyl-CH2Cl | cyclopropyl-CH2-O-C6H3(F)-Br | n.d. | 1.20 (D) |

*the mesylate can be prepard as described in WO2011008663

Example XVII

Example XVII.1

General Route

1-Bromo-4-(2-bromoethoxy)benzene

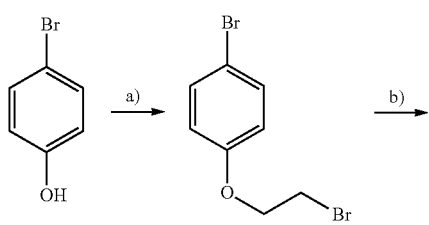

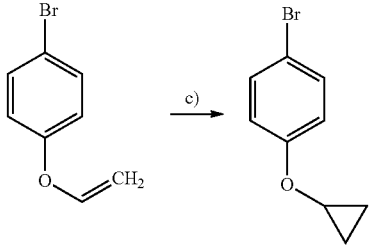

a) 55.0 g (318 mmol) 4-bromophenol and 14.1 g (352 mmol) NaOH are added to 110 ml water. 41.1 ml (477 mmol) dibromoethane are added slowly and the reaction mixture is stirred for 16 h under reflux. Afterwards the reaction mixture is extracted with DCM and the solvent is removed in vacuo. The crude product is purified by column chromatography (silica gel, CyH/EtOAc 4/1).

b) 52.0 g (186 mmol) of 1-bromo-4-(2-bromoethoxy)benzene is added to 300 ml THF and chilled to 0° C. Within 30 min 25.0 g (223 mmol) KOtBu are added to this mixture in several portions. The cooling bath is removed and the reaction mixture is stirred at r.t. over night. The reaction is queched by the addition of water. The resulting mixture is extracted with EtOAc (2×). The org. phases are combined, washed with sat. aq. NaCl solution, dried with MgSO₄ and the solvent is removed in vacuo. The resulting product is used without further purification.

c) 39.0 g (176 mmol) of 1-bromo-4-vinyloxybenzene and 32.4 ml (441 mmol) chloroiodomethane are added to 500 ml dichloroethane and chilled to 0° C. During 1 h 200 ml (200 mmol) diethylzinc solution (c=1 mol/l in hexane) are added and stirring is continued for 2 h at 0° C. The reaction is quenched by the addition of 200 ml of a sat. aq. NH₄Cl solution and extracted with TBME (2×). The org. phases are combined, washed with sat. aq. NaCl solution, dried with MgSO₄ and the solvent is removed in vacuo. The crude product is purified by column chromatography (silica gel, PE)

C₉H₉BrO (M=213.1 g/mol)
EI-MS: 212/214 [M]⁺
R_f(TLC): 0.4 (silica gel, PE)

The following compounds are prepared analogously to example XVII.1 For the examples XVII.2-XVII.4 the phenolate in step a) is preformed by reacting the appropriate phenol with NaOH in a MeOH/water (1/1) mixture at r.t. for 1 h. Then the solvent is removed in vacuo and the resulting sodium salt is reacted with dibromoethane (5 eq.) at 100° C. for 24 h. The reaction mixture is quenched by the addition of water and extracted with DCM.

For the example XVII.5 the reaction is done in THF by using NaH as base.

Example XVIII

2-Bromo-5-cyclopropoxy-benzonitrile

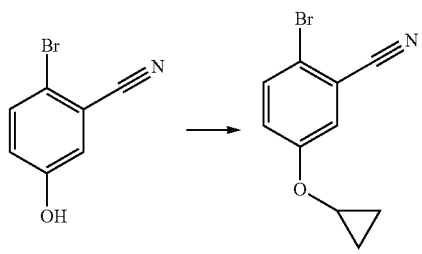 [SMILES: N#Cc1cc(O)ccc1Br ; N#Cc1cc(OC2CC2)ccc1Br]

To a stirred mixture of 2.50 g (13 mmol) 2-bromo-5-hydroxy-benzonitrile in 100 mL DMF are added 5.23 g (38 mmol) K₂CO₃ and 3.05 g (25 mmol) cyclopropylbromide. The reaction mixture is stirred for 16 h at 120° C. Afterwards the reaction is quenched by the addition of ice water and extracted with EtOAc. The org. layers are combined, washed with sat. aq. NaCl solution, dried over Na₂SO₄, filtered and the solvent is removed in vacuo. The crude product is purified by column chromatography (silica gel, PE/EtOAc).

C₁₀H₈BrNO (M=238.1 g/mol)
R_f(TLC): 0.8 (silica gel, PE/EtOAc 9/1))

| Ex. | Starting material | Product structure | Mass spec result | HPLC retention time (method) |
|---|---|---|---|---|
| XVII.1 | HO–C₆H₄–Br | cyclopropyl-O–C₆H₄–Br | 212/214 [M]⁺ | TLC: R_f= 0.4 (silica gel, PE) |
| XVII.2 | HO–C₆H₃(CH₃)–Br | cyclopropyl-O–C₆H₃(CH₃)–Br | n.d. | 5.89 (I) |
| XVII.3 | HO–C₆H₃(OCH₃)–Br | cyclopropyl-O–C₆H₃(OCH₃)–Br | n.d. | 5.30 (J) |
| XVII.4 | HO–C₆H₃(F)–Br | cyclopropyl-O–C₆H₃(F)–Br | 230/232 [M]⁺ | TLC: R_f= 0.55 (silica gel, hexane/EtOAc 9/1) |

Example XIX

Example XIX.1

General Route

7-Bromo-8-fluoro-3,4-dihydro-2H-benzo-[1,4]-dioxepine

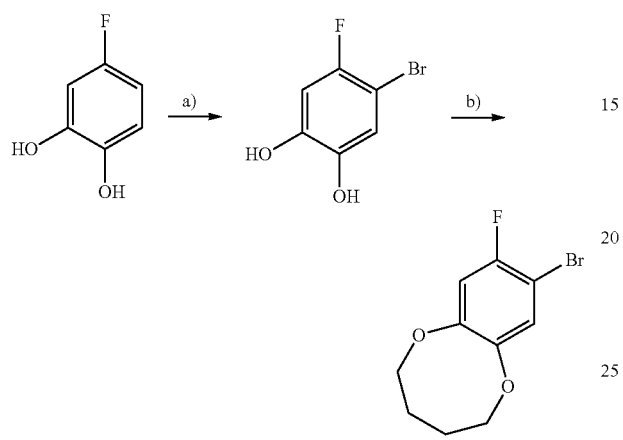

a) To 1.00 g (7.57 mmol) 4-fluorocatechol in 50 ml DCM are added 0.58 ml (11.4 mmol) bromine in 10 ml DCM. The reaction mixture is stirred at r.t. for 3 h. Then the solvent is removed in vacuo and the crude product is purified by column chromatography (silica gel, DCM/MeOH 9/1).

b) To 1.50 g (7.25 mmol) of 4-bromo-5-fluorobenzene-1,2-diol in 25 ml DMF are added 5.90 g (18.1 mmol) $Cs_2CO_3$ and 0.89 ml (8.70 mmol) 1,3-dibromopropane. The reaction mixture is stirred at 120° C. over night. The solvent is removed in vacuo and to the residue is added water. After extracting with EtOAc the org. phases are combined, washed with sat. aq. NaCl solution and dried over $MgSO_4$. The solvent is removed in vacuo and the resulting residue is purified by column chromatography (silica gel, PE/EtOAc 9/1→7/3).

$C_9H_8BrFO_2$ (M=247.1 g/mol)

EI-MS: 246/248 $[M]^+$ $R_f$(TLC): 0.50 (silica gel, PE/EtOAc 4/1)

The following compounds are prepared analogously to example XIX.1

| Ex. | Starting material | Product structure | Mass spec result | $R_f$ (TLC, silica gel) |
|---|---|---|---|---|
| XIX.1 | | | 246/248 $[M]^+$ | 0.40 (PE) |
| XIX.2 | | | 232/234 $[M]^+$ | 0.59 (PE/EtOAc 4/1) |
| XIX.3 | | | 232/234 $[M]^+$ | HPLC: $R_t$ = 1.07 (method B) |

Example XX

7-Bromo-2,3-dihydrobenzo[1,4]-dioxine-6-carbonitrile

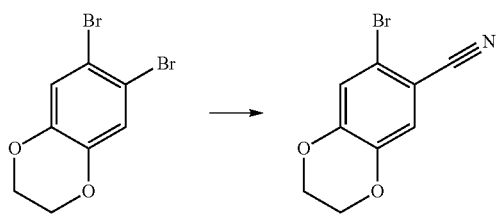 [SMILES: Brc1cc2c(cc1Br)OCCO2 ; N#Cc1cc2c(cc1Br)OCCO2]

A mixture of 20.0 g (62.6 mmol) of 6,7-dibromo-2,3-dihydrobenzo[1,4]dioxine, 8.50 g (93.9 mmol) CuCN and 13.0 (93.9 mmol) $K_2CO_3$ in 300 mL DMF is stirred at 150° C. for 6 d. The reaction is quenched by the addition of water and extracted with EtOAc. The org. layers are combined and washed with water (3×) and sat. aq. NaCl solution. After drying over $Na_2SO_4$, the mixture is filtered and the solvent is removed in vacuo. The resulting residue is purified by column chromatography (silica gel, PE/EtOAc 20/1→10/1).

$C_9H_6BrNO_2$ (M=247.1 g/mol)
$R_f$ (TLC): 0.20 (silica gel, PE/EtOAc 10/1)

Example XXI

1-Bromo-4-(3,3-difluoro-propoxy)benzene

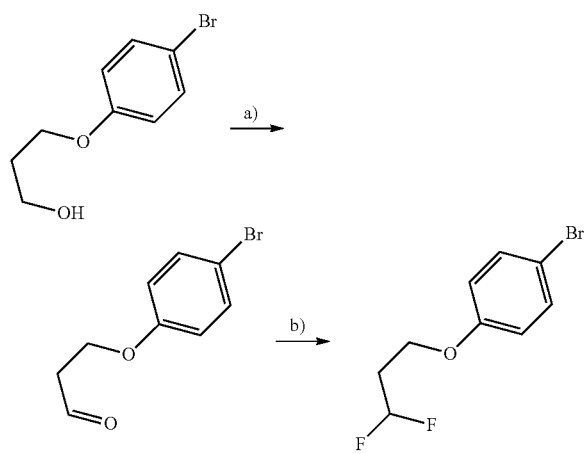

a) To 0.69 g (2.96 mmol) 1-bromo-4-(3-hydroxypropoxy) benzene in 8.5 ml DCM are added 1.30 g (2.96 mmol) Dess-Martin-periodinane (1,1,1-triacetoxy-1,1-dihydro-1,2-benzoiodoxol-3(1H)-one) and the reaction mixture is stirred at r.t. over night. The mixture is diluted with DCM, washed with water, dried over $MgSO_4$, filtered and the solvent is removed in vacuo. The residue is dissolved in DIPE/TBME, filtered and the solvent is removed in vacuo again.

$C_9H_9BrO_2$ (M=229.1 g/mol)
$R_f$ (TLC): 0.30 (silica gel, PE/EtOAc 8/2)

b) To 0.50 g (2.18 mmol) of the above mentioned product in 4 mL DCM are added 0.57 mL (4.37 mmol) DAST and the resulting mixture is stirred at r.t. over night. The mixture is diluted with DCM, washed with an aq. $NaHCO_3$ solution (2×), dried over $MgSO_4$, filtered and the solvent is removed in vacuo.

$C_9H_8BrF_2O$ (M=251.1 g/mol)
EI-MS: 250/252 $[M]^+$
$R_t$ (HPLC): 1.17 min (method C)

Example XXII

Example XXII.1

General Route

(S)-1-(4-((R)-1-(4-Cyclopropylmethoxyphenyl)-pyrrolidin-3-yloxy)-phenyl)ethanamine hydrochloride

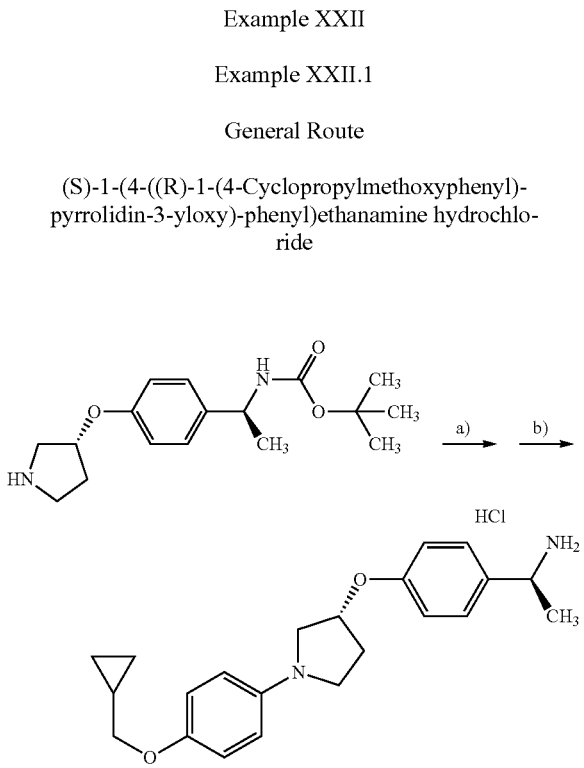

a) 2.00 g (6.53 mmol) of example XIII.1, 1.80 g (6.3 mmol) of example XVI.26, 2.60 g (26.2 mmol) NaOtBu and 490 mg (0.66 mmol) chloro(2-dicyclohexylphosphino-2',4',6'-triisopropyl-1,1'-biphenyl)(2-(2-aminoethyl)-phenyl)-palladium (II) are added to 80 mL dioxane and stirred at r.t. for 15 h under inert gas atmosphere. Water is added and stirring is continued for 30 min. After that the resulting precipitate is filtered off and triturated with DIPE.

$C_{27}H_{36}N_2O_4$ (M=452.6 g/mol)
ESI-MS: 453 $[M+H]^+$
$R_t$ (HPLC): 1.32 min (method C)

b) To 2.10 g (4.64 mmol) of the above mentioned product are added 6 mL (6.96 mmol) of an ethanolic HCl solution (c=1.3 mol/l) and the mixture is stirred at r.t. over night. The solvent is removed in vacuo and the product is dried in vacuo.

$C_{22}H_{28}N_2O_2$*HCl (M=388.9 g/mol)
ESI-MS: 353 $[M+H]^+$
$R_t$ (HPLC): 1.00 min (method K)

The following compounds are prepared analogously to example XXII.1

For the example XXVI.2 the Buchwald coupling in a) is done at 60° C. and the precipitate is dissolved in EtOAc, dried over $MgSO_4$, filtered and the solvent is removed in vacuo. After the deprotection in b), the crude product is treated with a basic aq. solution and extracted with DCM. The org. layers are combined, dried over MgSO4, filtered and the solvent is removed in vacuo. The residue is triturated with DIPE.

For example XXII.3 product XXII.1 is purified by HPLC using aq. ammonia as modifier.

For example XXII.4 Cs2CO3 is used as base and the reaction is done at 80° C. For step b) a solution of HCl in dioxane is used for the deprotection.

| Ex. | Starting material(s) | Product structure | Mass spec result | HPLC retention time (method) |
|---|---|---|---|---|
| XXII.1 | XIII.1 + XVI.1 | | 353 [M + H]⁺ | 1.00 (K) |
| XXII.2 | XXV | | 327 [M + H]⁺ | 0.81 (M) |
| XXII.3 | XIII.1 + XVI.1 | | 353 [M + H]⁺ | 1.00 (K) |
| XXII.4 | XIII.1 + XVII.2 | | 353 [M + H]⁺ | 1.02 (K) |

Example XXIII (S)-1-(4-((R)-1-(4-Isopropoxyphenyl-pyrrolidin-3-yloxy)-phenyl)ethanamine hydrochloride

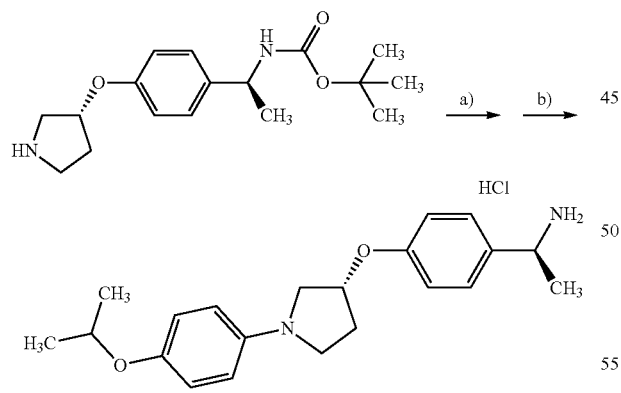

a) 3.00 g (8.81 mmol) of example XIII.1 (90%), 2.53 g (11.0 mmol) of 4-isopropoxy-1-bromo benzene, 3.60 g (35.0 mmol) NaOtBu and 420 mg (0.88 mmol) X-Phos and 410 mg (0.44 mmol) Pd(dba)2 are added to 40 mL dioxane and stirred at 45° C. over night under inert gas atmosphere. Then the solvent is removed in vacuo and the residue is purified by column chromatography (silica gel, DCM/MeOH 50/1).

To the resulting product (2.50 g, 6.76 mmol) in 30 mL DCM and 1.03 g (10.1 mmol) TEA are added 1.50 g (6.76 mmol) BOC₂O and the resulting mixture is stirred at r.t. over night. The solvent is removed and the residue is purified by crystallization.

$C_{26}H_{36}N_2O_4$ (M=440.6 g/mol)

$R_f$(TLC): 0.70 min (silica gel, PE/EtOAc 3/1)

b) To 1.76 g (4.00 mmol) of the above mentioned product in 20 mL dioxane are added 2 mL (8.00 mmol) of an HCl solution in dioxane (c=4.0 mol/l) and the mixture is stirred at r.t. over night. Further 2 mL (8 mmol) of the HCl solution in dioxane are added and stirring is continued for an additional day. Then the solvent is removed in vacuo and the product is triturated with diethylether.

$C_{21}H_{28}N_2O_2$*HCl (M=376.9 g/mol)

ESI-MS: 341 [M+H]⁺

$R_t$ (HPLC): 0.98 min (method K)

Example XXIV (S)-1-(4-((R)-1-(4-Hydroxyohenyl)-pyrrolidin-3-yloxy)-phenyl)ethyl) acetamide

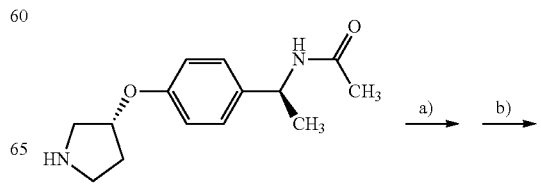

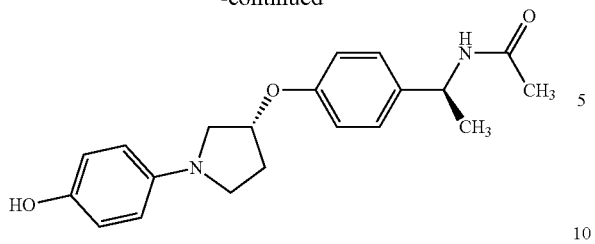

a) 1.50 g (5.27 mmol) of example VIII.1, 1.39 g (5.27 mmol) 4-benzyloxybromo-benzene, 4.29 g (13.2 mmol) $Cs_2CO_3$, 59.1 mg (0.26 mmol) $Pd(OAc)_2$ and 126 mg (0.26 mmol) X-Phos are added to 7.5 mL toluene and 3 mL tert-butanol. The reaction mixture is stirred at 120° C. over night under inert gas atmosphere. Then water is added and the mixture is extracted with EtOAc (2×). The org. layers are combined, dried over $MgSO_4$, filtered and the solvent is removed in vacuo. The crude product is purified by HPLC ($MeOH/H_2O/NH_3$).

$C_{27}H_{30}N_2O_3$ (M=430.5 g/mol)
ESI-MS: 431 [M+H]$^+$
$R_t$ (HPLC): 1.66 min (method L)

b) 0.80 g (1.86 mmol) of the above mentioned product in 50 mL ethanol are hydrogenated at r.t. using 100 mg Pd/C (10%) and a hydrogen pressure of 2 bar. After completion the reaction mixture is filtered, the solvent is removed in vacuo and the crude product is purified by HPLC ($MeOH/H_2O/NH_3$).

$C_{20}H_{24}N_2O_3$ (M=340.4 g/mol)
ESI-MS: 341 [M+H]$^+$
$R_t$ (HPLC): 0.86 min (method C)

Example XXV (trans)-tert-Butyl-3-(4-((1S)-1-acetamidoethyl)phenoxy-4-hydroxypyrrolidine-1-carboxylate

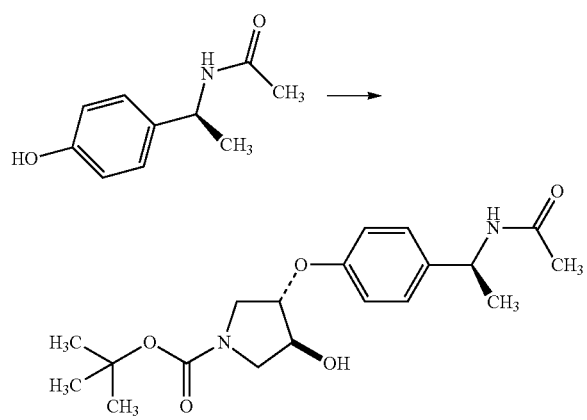

To 1.35 g (7.56 mmol) of example IV.1 and 1.40 g (7.56 mmol) tert-butyl 6-oxy-3-azabicyclo[3.1.0]hexane-3-carboxylate in 17 mL DMF are added 3.69 g (11.3 mmol) $Cs_2CO_3$ and the reaction mixture is stirred at 80° C. over night. Then water is added and the mixture is extracted with EtOAc. The org. layer is washed with aq. NaOH solution (c=1 mol/L), dried over $Na_2SO_4$, filtered and the solvent is removed in vacuo.

The product is a mixture of the two trans diastereoisomers regarding the 3 and 4 position of the pyrrolidine.

$C_{19}H_{28}N_2O_5$ (M=364.4 g/mol)
ESI-MS: 365 [M+H]$^+$
$R_t$ (HPLC): 1.01 min (method C)

Example XXVI

Example XXVI.1

General Route (1S)—N-1-(4-((trans)-4-Methoxypyrrolidin-3-yloxy)-phenyl)acetamide hydrochloride

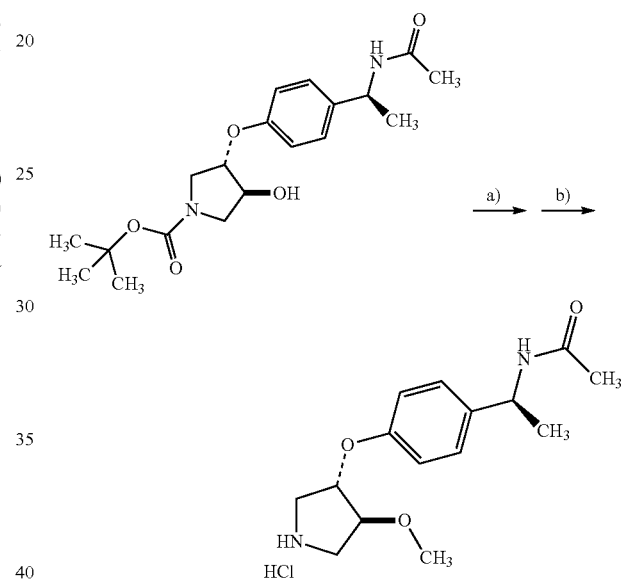

a) 0.35 g (0.96 mmol) of example XXV in 6 mL THF are charged with 53.8 mg (1.35 mmol) NaH (60%) and stirred at r.t. for 20 min. then 90 μL (1.44 mmol) methyl iodide are added and the reaction mixture is stirred at r.t. over night. Then water is added and the mixture is extracted with EtOAc (2×). The org. layers are combined, dried over $MgSO_4$, filtered and the solvent is removed in vacuo. The crude product is purified by HPLC ($MeOH/H_2O/NH_3$).

$C_{20}H_{30}N_2O_5$ (M=378.5 g/mol)
ESI-MS: 379 [M+H]$^+$
$R_t$ (HPLC): 1.04 min (method C)

b) 0.40 g (1.06 mmol) of the above mentioned product in 6 mL THF and some drops MeOH are charged with 0.79 mL (3.17 mmol) of an HCl solution in dioxane (c=4 mol/L) and stirred at r.t. over night. Then the solvent is removed in vacuo.

$C_{15}H_{22}N_2O_3$*HCl (M=314.8 g/mol)
ESI-MS: 279 [M+H]$^+$
$R_t$ (HPLC): 0.66 min (method C)

The following compounds are prepared analogously to example XXVI.1

All products are mixtures of the two trans diastereoisomers regarding the 3 and 4 position of the pyrrolidine.

| Ex. | Starting material | Product structure | Mass spec result | HPLC retention time (method) |
|---|---|---|---|---|
| XXVI.1 | XXV + MeI | | 279 [M + H]$^+$ | 0.66 (C) |
| XXVI.2 | XXV + ethyl iodide | | 293 [M + H]$^+$ | 0.82 (C) |
| XXVI.3 | XXV + 2-bromoethyl-methylether | | 323 [M + H]$^+$ | 0.69 (C) |

Example XXVII (1S)—N-1-(4-((cis)-4-Methoxypyrrolidin-3-yloxy)-phenyl)acetamide hydrochloride

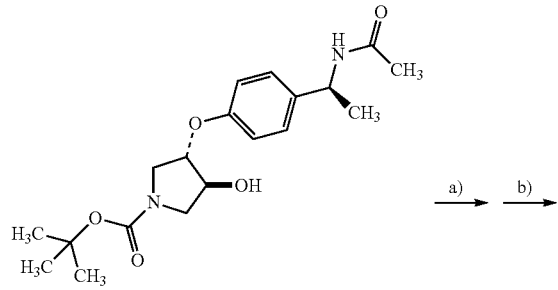

a) b) →

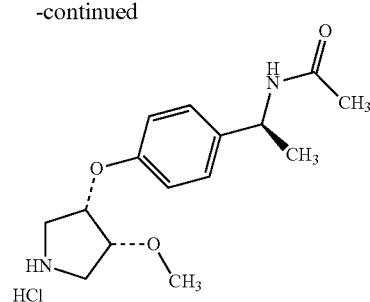

a) 0.50 g (1.37 mmol) of example XXV in 4 mL THF are charged with 0.23 mL (1.65 mmol) TEA and 0.14 mL (1.65 mmol) MsCl and the reaction mixture is stirred at r.t. over night. Then water is added and the mixture is extracted with EtOAc (2×). The org. layers are combined, dried over MgSO$_4$, filtered and the solvent is removed in vacuo.

The product is a mixture of the two cis diastereoisomers regarding the 3 and 4 position of the pyrrolidine.

$C_{20}H_{30}N_2O_7S$ (M=442.5 g/mol)
ESI-MS: 443 [M+H]$^+$
$R_t$ (HPLC): 0.98 min (method C)

b) 0.20 g (0.45 mmol) of the above mentioned product in 1 mL DMF are charged with 21.7 mg (0.68 mmol) MeOH and 16.3 mg (0.68 mmol) NaH. The resulting mixture is stirred at for 3 h. Some water is added and the mixture is purified by HPLC (acetone/$H_2O$/$NH_3$). The product is added to 3 mL MeOH and charged with 1.69 mL (2.11 mmol) of an HCl solution in MeOH (c=1.3 mol/L) and stirred at r.t. over night. Then the solvent is removed in vacuo.

The product is a mixture of the two cis diastereoisomers regarding the 3 and 4 position of the pyrrolidine $C_{15}H_{22}N_2O_3$*HCl (M=314.8 g/mol)
ESI-MS: 279 [M+H]$^+$
$R_t$ (HPLC): 0.66 min (method C)

Example XXVIII (S)-1-(4-(Cyclopropylmethoxy)phenyl)pyrrolidin-3-yl-methanesulfonate

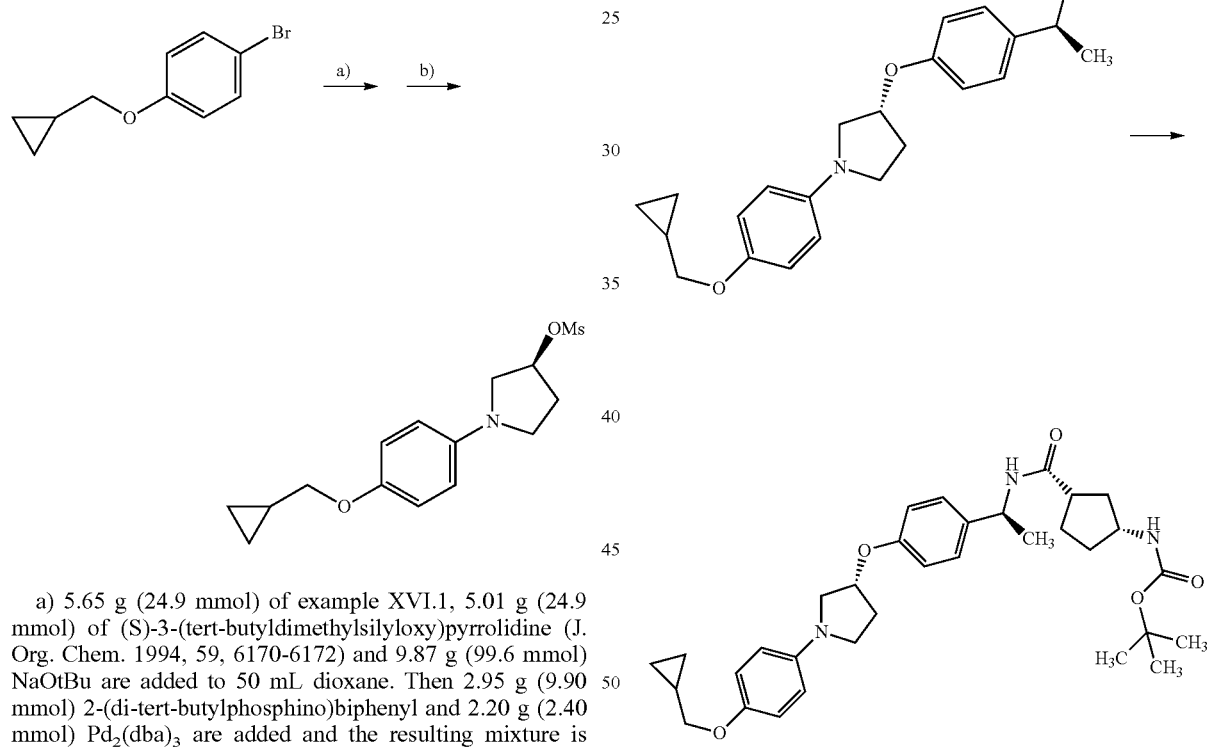

a) 5.65 g (24.9 mmol) of example XVI.1, 5.01 g (24.9 mmol) of (S)-3-(tert-butyldimethylsilyloxy)pyrrolidine (J. Org. Chem. 1994, 59, 6170-6172) and 9.87 g (99.6 mmol) NaOtBu are added to 50 mL dioxane. Then 2.95 g (9.90 mmol) 2-(di-tert-butylphosphino)biphenyl and 2.20 g (2.40 mmol) $Pd_2(dba)_3$ are added and the resulting mixture is stirred at 45° C. over night under inert gas atmosphere. Then the solvent is removed in vacuo and the residue is taken up in EtOAc, washed with water (2×), dried over $Na_2SO_4$, filtered and the solvent is removed in vacuo. The residue is purified by column chromatography (silica gel; PE/EtOAc 95/5→80/20) and HPLC (MeOH/$H_2O$/TFA). To the resulting intermediate is added DCM and TFA and the mixture is stirred at r.t. for 2 h. Then the solvent is removed in vacuo.

$C_{14}H_{19}NO_2$ (M=233.3 g/mol)
ESI-MS: 234 [M+H]$^+$
$R_t$ (HPLC): 0.83 min (method E)

b) To 1.00 g (4.29 mmol) of the above mentioned product and 715 µL (5.16 mmol) TEA in 50 mL DCM are added at 0° C. 401 µL (5.16 mmol) MsCl. After 20 min stirring at 0° C. cooling is removed and the mxiture is allowed to warm to r.t. The mixture is diluted with DCM, washed with an aq. $NaHCO_3$ solution, dried over $Na_2SO_4$, filtered and the solvent is removed in vacuo.

$C_{15}H_{21}NO_4S$ (M=311.4 g/mol)
EI-MS: 312 [M+H]$^+$
$R_t$ (HPLC): 1.12 min (method E)

Example XXIX

Example XXIX.1

General Route (1R,3S)-tert-Butyl-3-(1-(4-(1-(4-(cyclopropylmethoxy)phenyl)pyrrolidin-3-yloxy)phenyl)ethylcarbamoyl)cyclopentylcarbamate

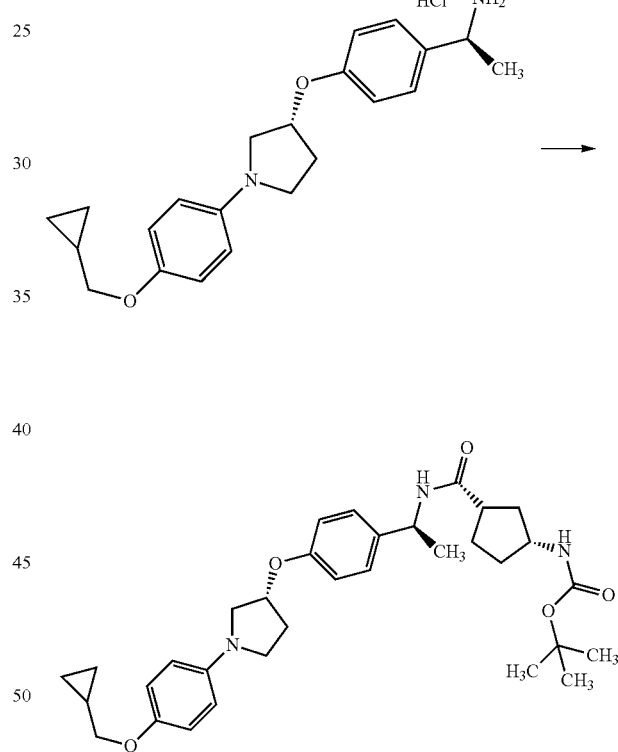

65.1 mg (0.28 mmol) (1S,3R)—N-Boc-3-aminocyclopentanecarboxylic acid, 150 µl (0.85 mmol) DIPEA and 91.1 mg (0.28 mmol) TBTU are added to 3 ml DMF and stirred for 10 min. Then 100 mg (0.18 mmol) of the amine XXII.1 are added and the resulting mixture is stirred at r.t. over night. Afterwards the mixture is directly purified by HPLC (MeOH/$H_2O$/$NH_3$).

$C_{33}H_{45}N_3O_5$ (M=563.7 g/mol)
ESI-MS: 564 [M+H]$^+$
$R_t$ (HPLC): 1.56 min (method B)

The following compounds are prepared analogously to example XXIX.1

| Ex. | Starting material | Product structure | Mass spec result | HPLC retention time (method) |
|---|---|---|---|---|
| XXIX.1 | XXII.1 | | 564 [M + H]⁺ | 1.56 (B) |
| XXIX.2 | XX.3 | | 463 [M + H]⁺ | 1.17 (C) |

Example XXX

Example XXX.1

General Route

2(-2-Benzyloxy-acetylamino)-4-methyl-thiazole-5-carboxylic acid

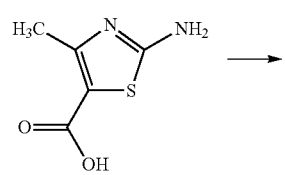

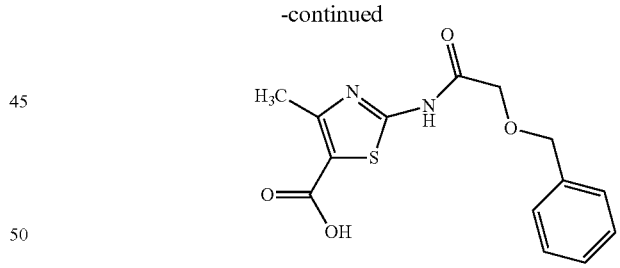

300 mg (1.90 mmol) 2-Amino-4-methylthiazole-5-carboxylic acid and 0.67 mL (6.07 mmol) N-methylmorpholine are added to 20 mL DMF. After adding 0.32 mL (2.09 mmol) benzyloxyacetyl chloride the resulting mixture is stirred at 80° C. over night. Then the mixture is callowed to cool to r.t. and slightly acidified with aq. HCl solution (c=1 mol/L). The solvent is removed in vacuo, water is added and the suspension is stirred for 10 min before the precipitate is filtered off and dried.

$C_{14}H_{14}N_2O_2S$ (M=306.3 g/mol)
ESI-MS: 307 [M+H]⁺
$R_t$ (HPLC): 0.89 min (method M)

The following compounds are prepared analogously to example XXX.1

| Ex. | Acylating reagent | Product structure | Mass spec result | HPLC retention time (method) |
|---|---|---|---|---|
| XXX.1 | benzyloxy acetyl chloride | ![structure] | 307 [M + H]⁺ | 0.89 (M) |
| XXX.2 | Acetoxy-acetyl chloride | ![structure] | 259 [M + H]⁺ | 0.68 (M) |

Example XXXI

3-Cyano-1-methyl-1H-pyrazole-4-carboxylic acid

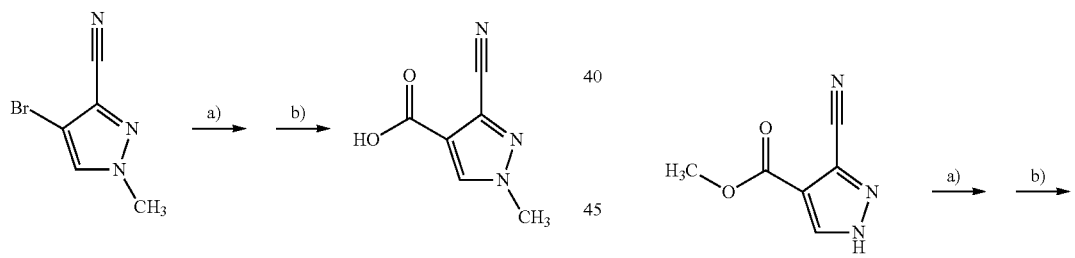

a) 500 mg (2.69 mmol) 4-Bromo-1-methyl-1H-pyrazole-3-carbonitrile, 1.21 mg (5.00 μMol) Pd(OAc)$_2$, 44.7 mg (0.08 mmol) dppf and 661 mg (8.06 mmol) NaOAc are added to 20 mL MeOH and stirred in an atmosphere of CO (p=10 bar) at 120° C. over night. Then the solvent is removed and the residue is purified by HPLC (MeOH/H$_2$O/TFA).

b) 100 mg (0.61 mmol) of the above mentioned product are added to 16 mL of a 1/1 mixture of MeOH and THF and charged with 0.23 mL (0.91 mmol) of an aq. NaOH solution (c=4 mol/L). The resulting mixture is stirred at r.t. over night. Then the solvent is removed, water is added to the residue and the solution is acidified with an aq. HCl solution (c=1 mol/L). The precipitate is filtered off and dried.

C$_6$H$_5$N$_3$O$_2$ (M=151.1 g/mol)

ESI-MS: 152 [M+H]⁺

R$_t$ (HPLC): 0.45 min (method D)

Example XXXII

Example XXXII.1

General Route

3-Cyano-1-(tetrahydro-2H-pyran-2-yl)-1H-pyrazole-4-carboxylic acid

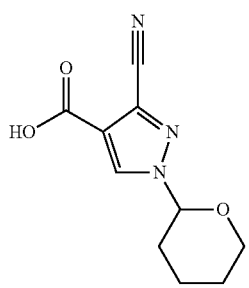

a) 2.00 g (13.2 mmol) Methyl 3-cyano-1H-pyrazole-4-carboxylate and 2.11 mL (23.1 mmol) 3,4-dihydropyrane are added to 30 mL THF and charged with 100 μL TFA and stirred at 60° C. over night. The solvent is removed, diluted with DCM and washed with a saturated aq. NaHCO$_3$ solution and the solvent is removed again.

b) 0.90 g (3.83 mmol) of the above mentioned product are added to 20 mL MeOH and 1.43 mL of an aq NaOH solution (c=4.0 mmol/L) and stirred at r.t. for 4 h. The mixture is filtered and acidified with aq. HCl solution (c=4 mol/L) and extracted with DCM (3×). The org. layers are combined, dried over MgSO$_4$, filtered and the solvent is removed in vacuo.

The crude product is purified by HPLC (ACN, H$_2$O, TFA) C$_{10}$H$_{11}$N$_3$O$_3$ (M=221.2 g/mol)
ESI-MS: 222 [M+H]$^+$
R$_t$ (HPLC): 0.70 min (method D)

The following compounds are prepared analogously to example XXXII.1 under inert gas atmosphere. The reaction mixture is filtered, the solvent is removed in vacuo and the residue is purified by HPLC.

Method C)

To 0.28 mmol of the appropriate amine in 1.5 mL toluene and 0.5 mL tert-butanol are added 0.28 mmol of the arylbromide, 0.70 mmol Cs$_2$CO$_3$, 14.0 μmol X-Phos and 14 μmol Pd(OAc)$_2$. The mixture is stirred at 120° C. over night under inert gas atmosphere. A small amount of water and MeOH is addedd, the mixture is filtered and afterwards purified by HPLC.

Method D)

To 0.40 mmol of the appropriate amine in 2.5 mL dioxane are added 0.40 mmol of the arylbromide, 1.61 mmol NaOtBu, 0.70 mmol 2-(di-tert-butylphosphino)biphenyl and 0.04 mmol Pd$_2$(dba)$_3$. The mixture is stirred for 45 min at 80° C. in a microwave oven under inert gas atmosphere. A small

| Ex. | Starting material | Product structure | Mass spec result | HPLC retention time (method) |
|---|---|---|---|---|
| XXXII.1 | | | 222 [M + H]$^+$ | 0.70 (D) |
| XXXII.2 | | | 219 [M + Na]$^+$ | 0.60 (D) |

Preparation of Final Compounds

General Synthetic Procedures

Buchwald Couplings

Method A)

To 1.00 mmol of the appropriate amine in 10 mL dioxane are added 1.00 mmol of the arylbromide, 4.00 mmol NaOtBu and 0.1 mmol chloro(2-dicyclohexylphosphino-2',4',6'-tri-isopropyl-1,1'-biphenyl)(2-(2-aminoethyl)-phenyl)-palladium (II). The resulting mixture is stirred at 45° C. for 3 h under inert gas atmosphere. The reaction mixture is filtered, the solvent is removed in vacuo and the residue is purified by HPLC.

Method B)

To 1.00 mmol of the appropriate amine in 10 mL dioxane are added 1.00 mmol of the arylbromide, 4.00 mmol NaOtBu, 0.40 mmol 2-(di-tert-butylphosphino)biphenyl and 0.10 mmol Pd$_2$(dba)$_3$. The mixture is stirred at 45° C. over night amount of water and MeOH is added, the mixture is filtered and afterwards purified by HPLC.

Example 1

Example 1.1

General Route

N—((S)-1-(4-((R)-1-(4-(Cyclopropylmethoxy)phenyl)pyrrolidin-3-yloxy)phenyl)ethyl)-acetamide

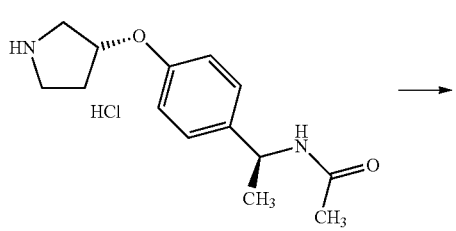

-continued

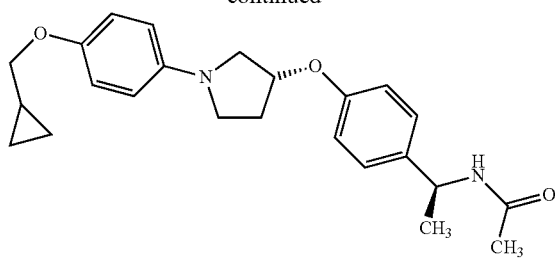

The title compound can be prepared according to the general procedure described in method A.

$C_{23}H_{30}N_2O_2$ (M=394.5 g/mol)
ESI-MS: 395 [M+H]$^+$
$R_t$ (HPLC): 0.98 min (method M)

The following compounds are prepared according to the general procedures A-D described above.

For examples 1.9-1.12 the reaction mixture is stirred at 80° C. for 1 h and at r.t. for 16 h.

For example 1.12 the reaction conditions are 6 h at 150° C.

For example 1.25 and 1.96 the reaction temperature is 55° C.

For example 1.28, 1.39, 1.102 and 1.103 the reaction conditions are 80° C. for 1-3 h.

For examples 1.37-38, 1.84-1.95 and 1.98-1.100 the reaction temperatures are 75-90° C.

For examples 1.77-1.81, 1.83 and 1.97 the reaction conditions are 70° C. for 5 h (2.5 h for 1.81).

| Ex. | Starting material(s) | Structure | Method | Mass spec result | HPLC retention time (method) |
|---|---|---|---|---|---|
| 1.1 | VIII.3 + XVI.1 | 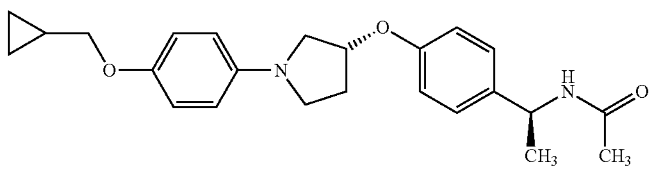 | A | 395 [M + H]$^+$ | 0.98 (M) |
| 1.2 | VIII.3 | 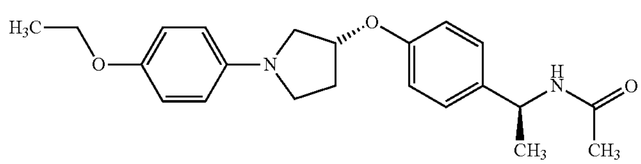 | D | 369 [M + H]$^+$ | 2.13 (A) |
| 1.3 | VIII.2 | 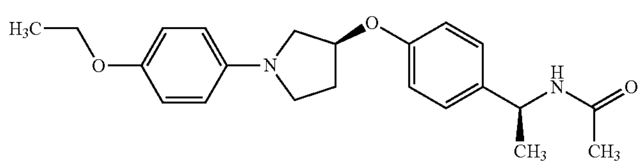 [SMILES: CCOc1ccc(N2CC[C@H](Oc3ccc([C@H](C)NC(C)=O)cc3)C2)cc1] | B | 369 [M + H]$^+$ | 2.08 (A) |
| 1.4 | VIII.2 | 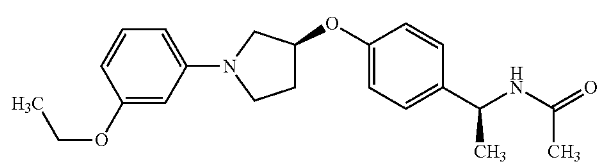 [SMILES: CCOc1cccc(N2CC[C@H](Oc3ccc([C@H](C)NC(C)=O)cc3)C2)c1] | B | 369 [M + H]$^+$ | 2.11 (A) |
| 1.5 | VIII.3 + 3-bromo-phenetole | 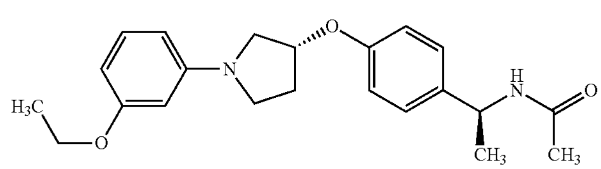 [SMILES: CCOc1cccc(N2CC[C@@H](Oc3ccc([C@H](C)NC(C)=O)cc3)C2)c1] | B | 369 [M + H]$^+$ | 2.11 (A) |
| 1.6 | VIII.3 + XVII.1 | 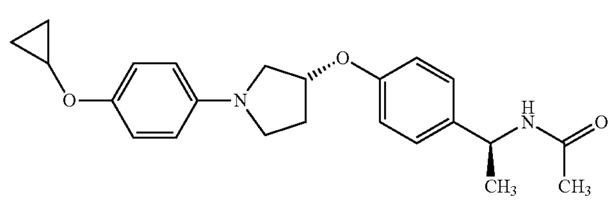 | B | 381 [M + H]$^+$ | 2.07 (A) |

-continued

| Ex. | Starting material(s) | Structure | Method | Mass spec result | HPLC retention time (method) |
|---|---|---|---|---|---|
| 1.7 | VIII.3 | 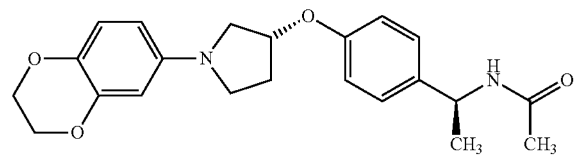 | D | 383 [M + H]+ | 1.92 (A) |
| 1.8 | VIII.3 | 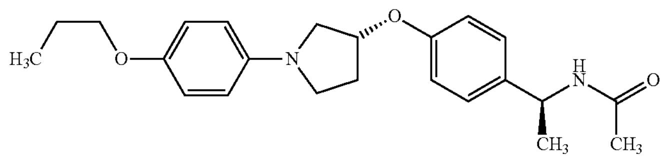 | D | 383 [M + H]+ | 1.01 (B) |
| 1.9 | VIII.3 + XVI.6 | 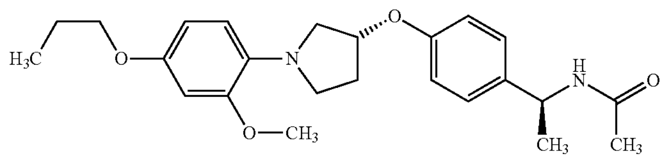 | B | 413 [M + H]+ | 1.20 (C) |
| 1.10 | VIII.3 + XVI.3 | 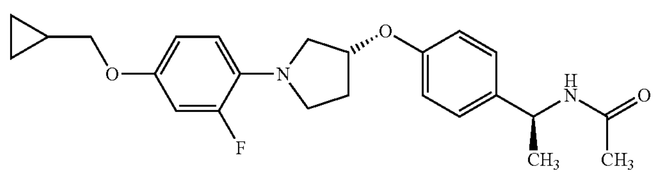 | B | 413 [M + H]+ | 1.23 (C) |
| 1.11 | VIII.3 | 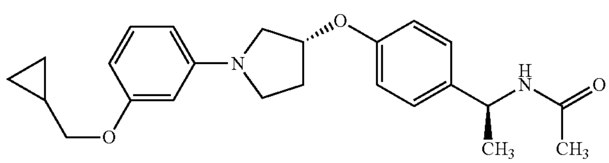 [SMILES: CC(=O)N[C@@H](C)c1ccc(O[C@@H]2CCN(c3cccc(OCC4CC4)c3)C2)cc1] | B | 395 [M + H]+ | 1.23 (C) |
| 1.12 | VIII.3 | 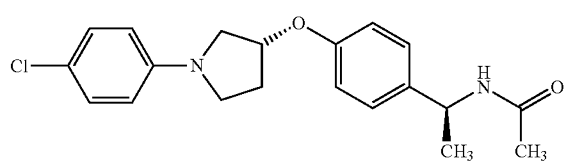 | B | 359 [M + H]+ | 1.21 (C) |
| 1.13 | VIII.3 + XVI.7 | 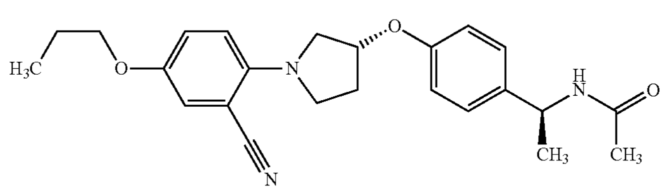 | D | 408 [M + H]+ | 2.22 (A) |
| 1.14 | VIII.1 + XVI.2 | 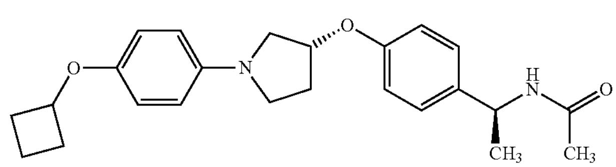 | B | 395 [M + H]+ | 1.21 (C) |
| 1.15 | VIII.1 | 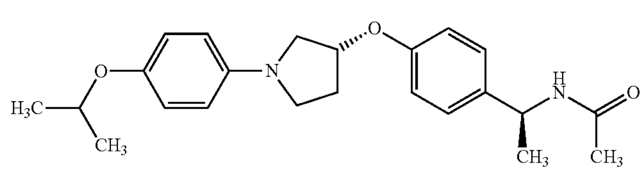 | B | 383 [M + H]+ | 1.15 (C) |

-continued

| Ex. | Starting material(s) | Structure | Method | Mass spec result | HPLC retention time (method) |
|---|---|---|---|---|---|
| 1.16 | VIII.1 + XVI.9 | (structure) | C | 431 [M + H]⁺ | 1.14 (C) |
| 1.17 | VIII.1 + XVI.10 | (structure) | C | 425 [M + H]⁺ | 1.21 (C) |
| 1.18 | VIII.1 + XVI.8 | (structure) | C | 425 [M + H]⁺ | 1.33 (H) |
| 1.19 | VIII.1 + XVI.4 | (structure) | C | 387 [M + H]⁺ | 1.29 (H) |
| 1.20 | VIII.1 | (structure) | C | 383 [M + H]⁺ | 1.21 (H) |
| 1.21 | VIII.1 | (structure) | C | 425 [M + H]⁺ | 1.24 (C) |
| 1.22 | VIII.1 | (structure) | C | 373 [M + H]⁺ | 1.24 (C) |
| 1.23 | VIII.1 | (structure) | C | 397 [M + H]⁺ | 1.21 (C) |

-continued

| Ex. | Starting material(s) | Structure | Method | Mass spec result | HPLC retention time (method) |
|---|---|---|---|---|---|
| 1.24 | VIII.1 | 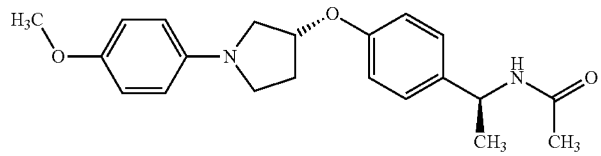 | C | 355 [M + H]⁺ | 1.21 (C) |
| 1.25 | VIII.1 + XVII.2 | 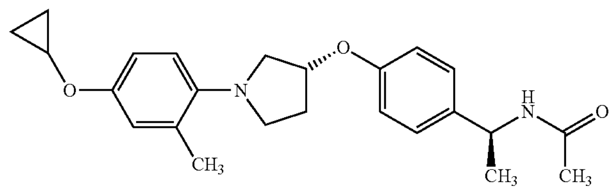 | A | 395 [M + H]⁺ | 1.20 (C) |
| 1.26 | VIII.1 | 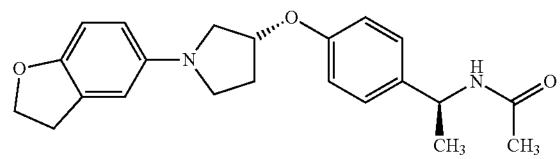 | B | 367 [M + H]⁺ | 1.05 (C) |
| 1.27 | VIII.1 | 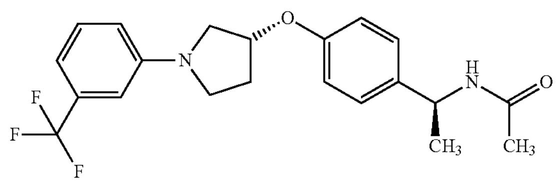 | B | 393 [M + H]⁺ | 1.21 (C) |
| 1.28 | VIII.1 | 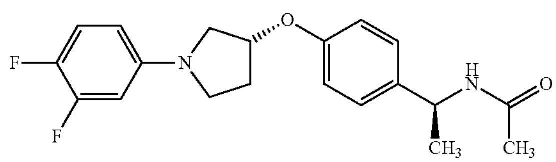 | B | 361 [M + H]⁺ | 1.66 (L) |
| 1.29 | VIII.1 + 2-chloro-1-iodo-propoxy-benzene*** | 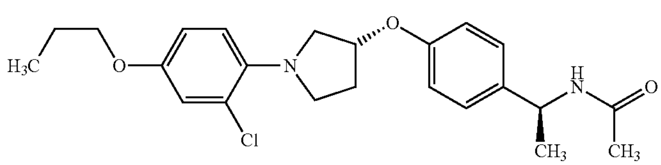 | B | 417 [M + H]⁺ | 1.26 (C) |
| 1.30 | VIII.1 | 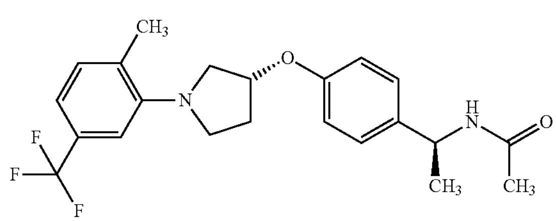 | B | 407 [M + H]⁺ | 1.24 (C) |
| 1.31 | VIII.1 | 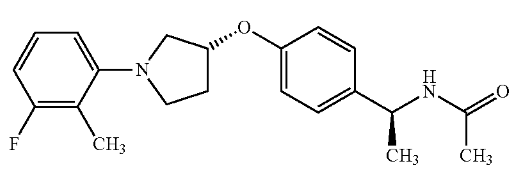 | B | 357 [M + H]⁺ | 1.18 (C) |

-continued

| Ex. | Starting material(s) | Structure | Method | Mass spec result | HPLC retention time (method) |
|---|---|---|---|---|---|
| 1.32 | VIII.1 | 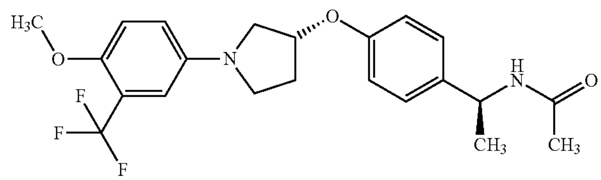 | B | 423 [M + H]+ | 1.15 (C) |
| 1.33 | VIII.1 | 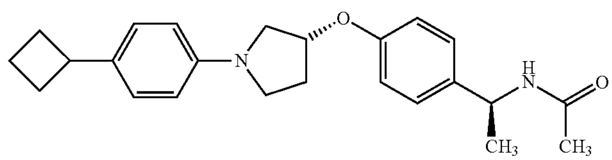 | B | 379 [M + H]+ | 1.30 (C) |
| 1.34 | VIII.1 | 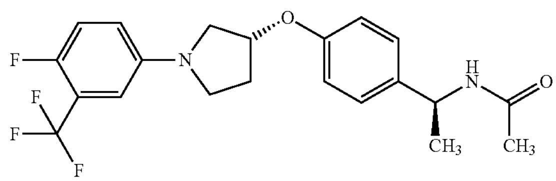 | B | 411 [M + H]+ | 1.19 (C) |
| 1.35 | VIII.1 | 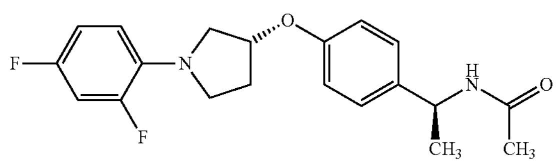 | B | 361 [M + H]+ | 1.14 (C) |
| 1.36 | VIII.1 + XIX.1 | 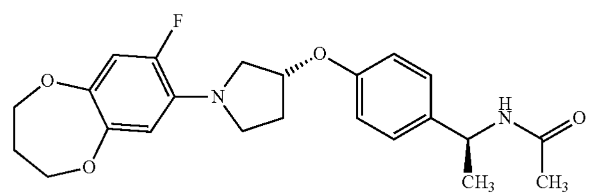 | B | 415 [M + H]+ | 1.09 (C) |
| 1.37 | VIII.1 + XVI.11 | 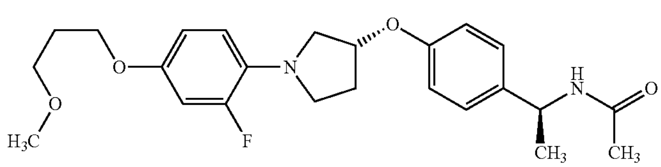 | B | 431 [M + H]+ | 1.29 (H) |
| 1.38 | VIII.1 + XVI.12 | 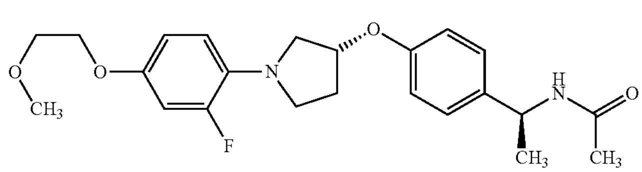 | B | 417 [M + H]+ | 1.22 (H) |
| 1.39 | VIII.1 | 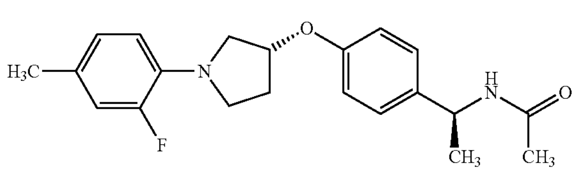 | B | 357 [M + H]+ | 1.18 (C) |

-continued

| Ex. | Starting material(s) | Structure | Method | Mass spec result | HPLC retention time (method) |
|---|---|---|---|---|---|
| 1.40 | VIII.1 + XVII.5 | 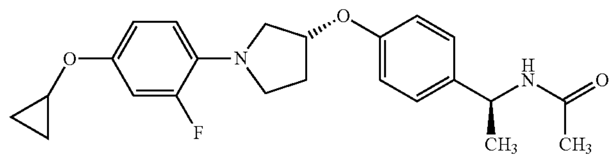 | B | 399 [M + H]+ | 1.33 (H) |
| 1.41 | VIII.1 + XVI.13 | 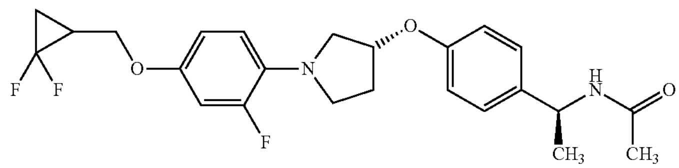 | B | 449 [M + H]+ | 1.31 (H) |
| 1.42 | VIII.1 + XVI.14 | 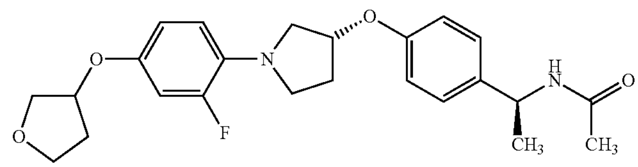 | B | 429 [M + H]+ | 1.23 (H) |
| 1.43 | VIII.1 + XVII.3 | 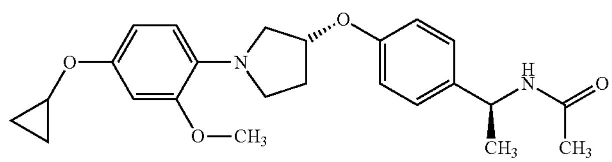 | B | 411 [M + H]+ | 1.29 (H) |
| 1.44 | VIII.1 | 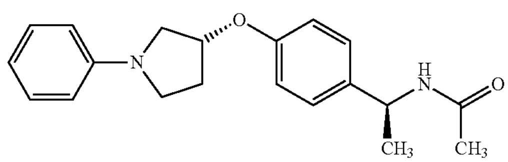 | B | 325 [M + H]+ | 1.54 (N) |
| 1.45 | XXVI.1 + XVI.1 | 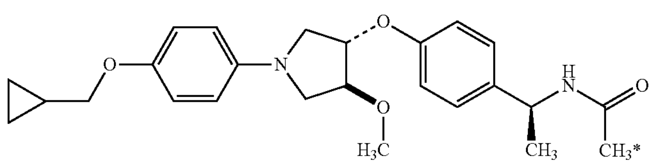 | B | 425 [M + H]+ | 1.61 (L) |
| 1.46 | VIII.1 + XIX.2 | 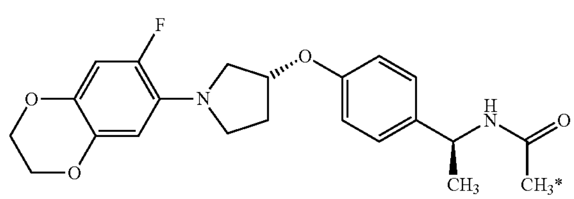 | B | 401 [M + H]+ | 1.08 (C) |
| 1.47 | VIII.1 + XIX.3 | 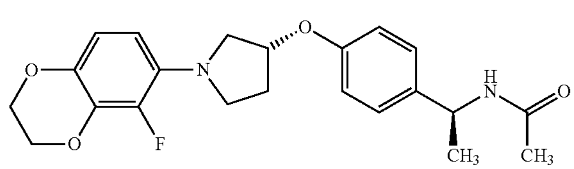 | B | 401 [M + H]+ | 1.05 (C) |

-continued

| Ex. | Starting material(s) | Structure | Method | Mass spec result | HPLC retention time (method) |
|---|---|---|---|---|---|
| 1.48 | VIII.2 + XVI.1 | 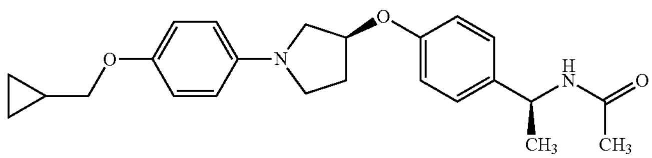 [SMILES: CC(=O)N[C@@H](C)c1ccc(O[C@H]2CCN(c3ccc(OCC4CC4)cc3)C2)cc1] | B | 395 [M + H]+ | 1.17 (C) |
| 1.49 | VIII.2 + XVI.1 | 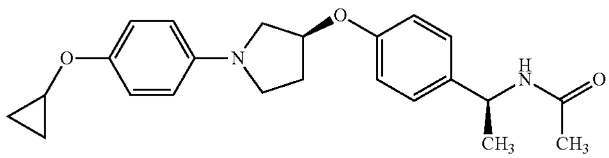 [SMILES: CC(=O)N[C@@H](C)c1ccc(O[C@H]2CCN(c3ccc(OC4CC4)cc3)C2)cc1] | B | 381 [M + H]+ | 1.19 (E) |
| 1.50 | VIII.1 | 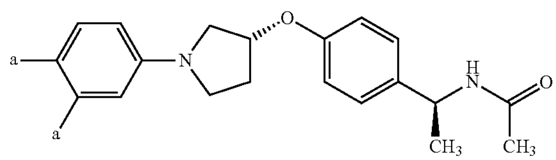 | B | 393 [M + H]+ | 1.24 (C) |
| 1.51 | XXVII + XVI.1 | 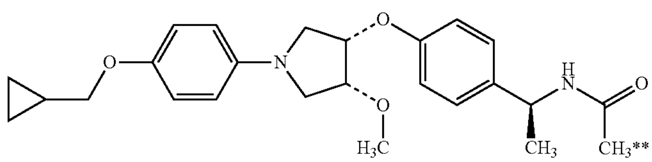 | B | 425 [M + H]+ | 1.16 (C) |
| 1.52 | VIII.1 | 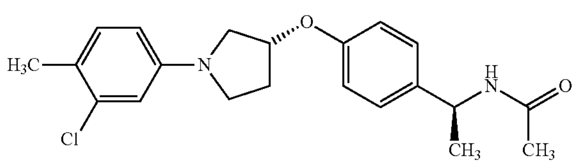 | B | 373 [M + H]+ | 1.24 (C) |
| 1.53 | VIII.1 | 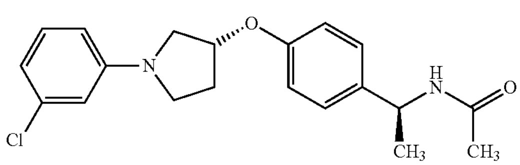 | B | 359 [M + H]+ | 1.19 (C) |
| 1.54 | VIII.1 | 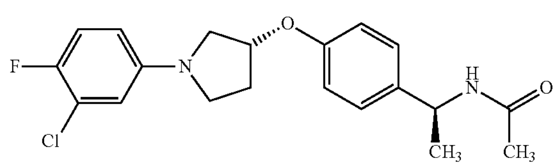 | B | 377 [M + H]+ | 1.18 (C) |
| 1.55 | VIII.1 | 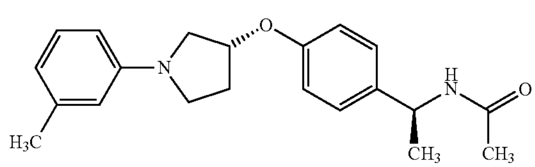 | B | 339 [M + H]+ | 1.16 (C) |
| 1.56 | XV + XVI.1 | 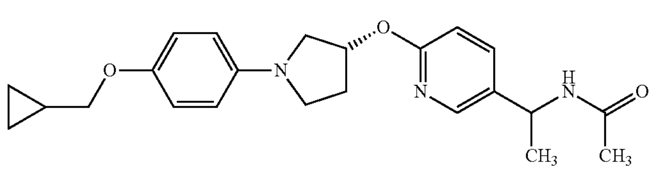 | B | 396 [M + H]+ | 1.14 (C) |

-continued

| Ex. | Starting material(s) | Structure | Method | Mass spec result | HPLC retention time (method) |
|---|---|---|---|---|---|
| 1.57 | VIII.1 + XVI.15 | 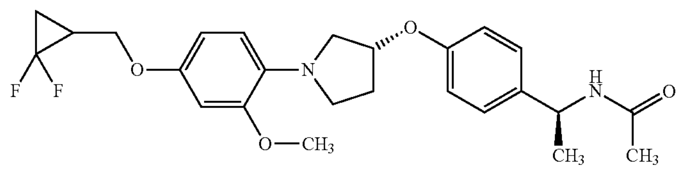 | B | 461 [M + H]+ | 1.29 (H) |
| 1.58 | VIII.1 | 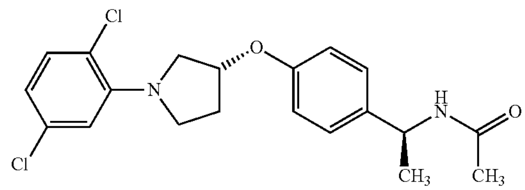 | B | 393 [M + H]+ | 1.25 (C) |
| 1.59 | XIV.1 | 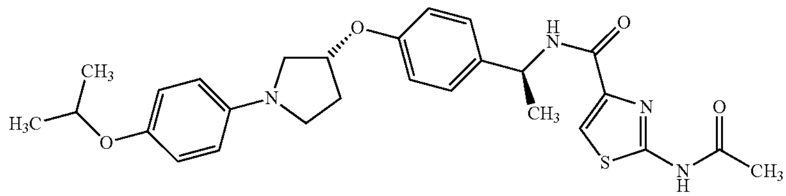 | B | 523 [M + H]+ | 1.19 (C) |
| 1.60 | VIII.1 | 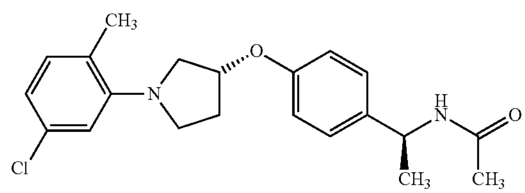 | B | 373 [M + H]+ | 1.23 (C) |
| 1.61 | VIII.1 | 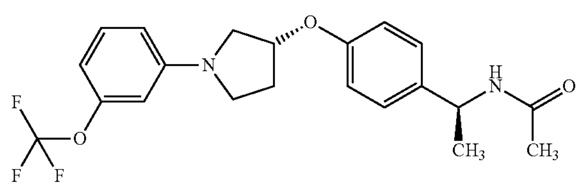 | B | 409 [M + H]+ | 1.21 (C) |
| 1.62 | VIII.1 | 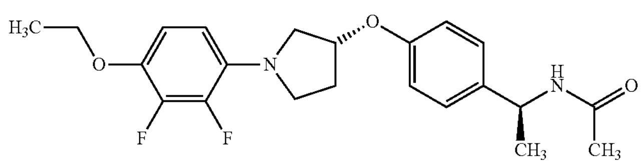 | D | 405 [M + H]+ | 1.33 (B) |
| 1.63 | XIII.3 + XVI.13 | 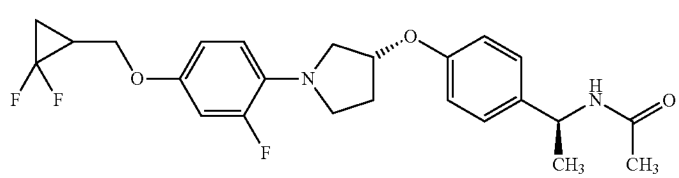 | B | 478 [M + H]+ | 1.18 (C) |
| 1.64 | XIII.3 + XVII.1 | 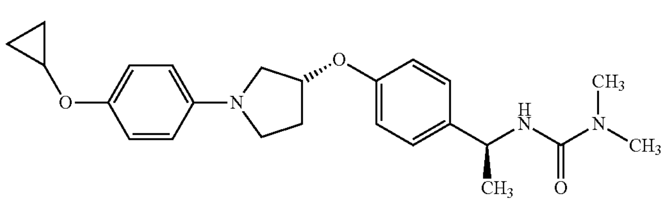 | B | 410 [M + H]+ | 1.17 (C) |

-continued

| Ex. | Starting material(s) | Structure | Method | Mass spec result | HPLC retention time (method) |
|---|---|---|---|---|---|
| 1.65 | XIII.3 | 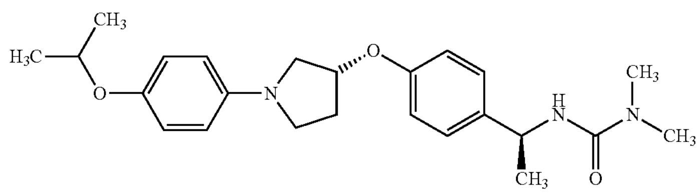 | B | 412 [M + H]⁺ | 1.17 (C) |
| 1.66 | VIII.1 | 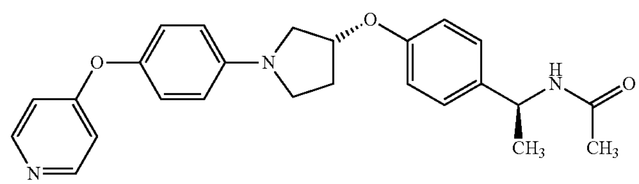 | B | 418 [M + H]⁺ | 1.17 (N) |
| 1.67 | VIII.1 | 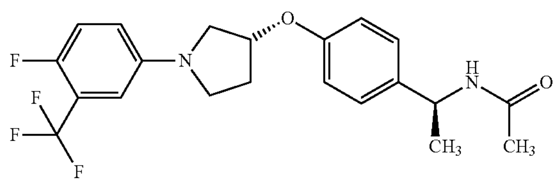 | B | 440 [M + H]⁺ | 1.20 (C) |
| 1.68 | XIII.3 + XVII.2 | 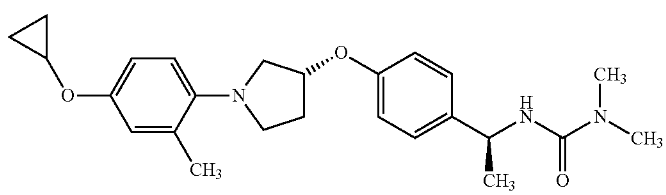 | B | 424 [M + H]⁺ | 1.22 (C) |
| 1.69 | VIII.1 | 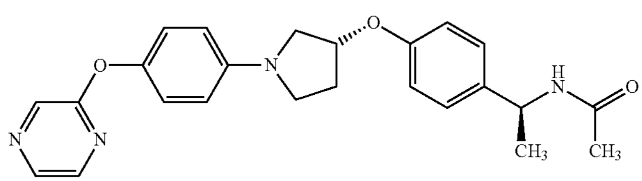 | B | 419 [M + H]⁺ | 1.47 (N) |
| 1.70 | VIII.1 + XVI.17 | 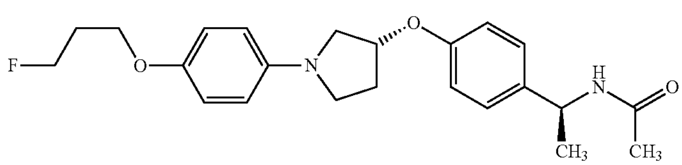 | A | 401 [M + H]⁺ | 1.18 (C) |
| 1.71 | VIII.1 + XVI.18 | 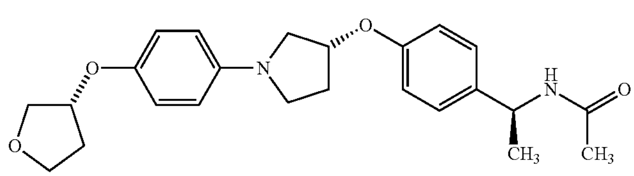 | A | 411 [M + H]⁺ | 1.04 (C) |
| 1.72 | VIII.1 | 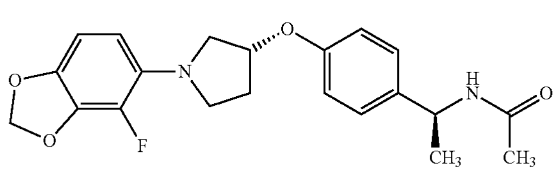 | B | 387 [M + H]⁺ | 1.01 (M) |

-continued

| Ex. | Starting material(s) | Structure | Method | Mass spec result | HPLC retention time (method) |
|---|---|---|---|---|---|
| 1.73 | VIII.1 + XVIII | 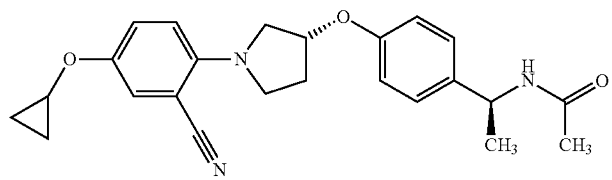 | A | 406 [M + H]⁺ | 1.30 (B) |
| 1.74 | XXVI.2 + XVI.1 | 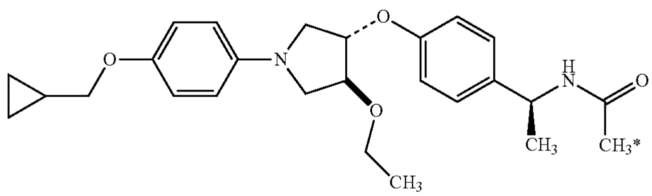 | A | 439 [M + H]⁺ | 1.28 (C) |
| 1.75 | VIII.1 | 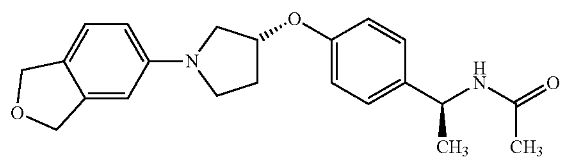 | B | 367 [M + H]⁺ | 1.03 (C) |
| 1.76 | VIII.1 | 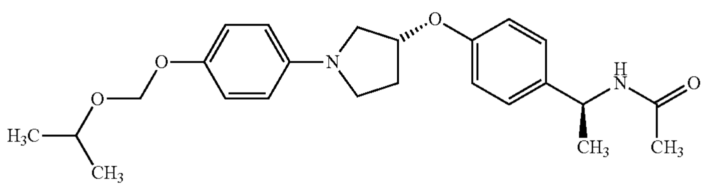 | B | 419 [M + Na]⁺ | 1.17 (C) |
| 1.77 | XXVI.3 + XVI.1 | 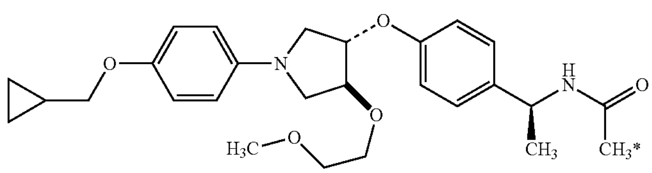 | A | 469 [M + H]⁺ | 1.17 (C) |
| 1.78 | VIII.1 | 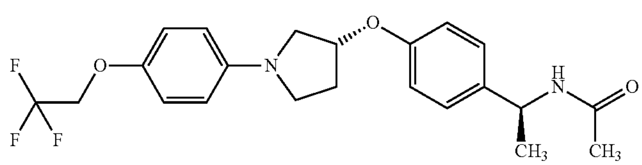 | A | 423 [M + H]⁺ | 1.17 (C) |
| 1.79 | VIII.1 | 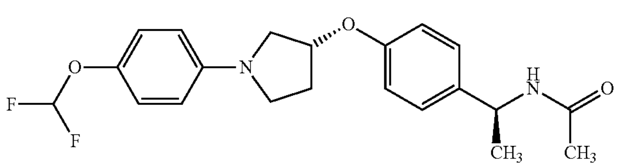 | A | 391 [M + H]⁺ | 1.13 (C) |
| 1.80 | VIII.1 | 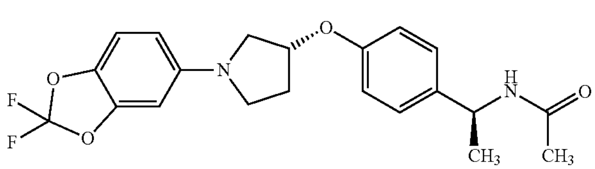 | A | 405 [M + H]⁺ | 1.22 (C) |

-continued

| Ex. | Starting material(s) | Structure | Method | Mass spec result | HPLC retention time (method) |
|---|---|---|---|---|---|
| 1.81 | VIII.1 + XVI.19 | 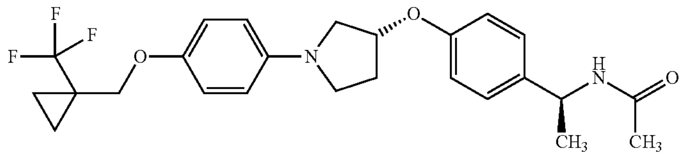 | A | 463 [M + H]+ | 1.22 (C) |
| 1.82 | VIII.1 + XX | 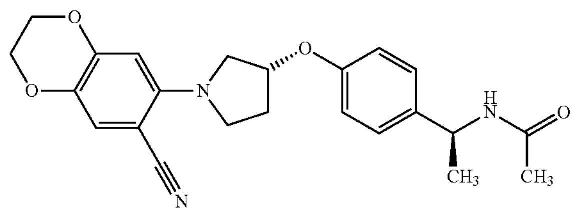 | A | 408 [M + H]+ | 1.21 (E) |
| 1.83 | VIII.1 | 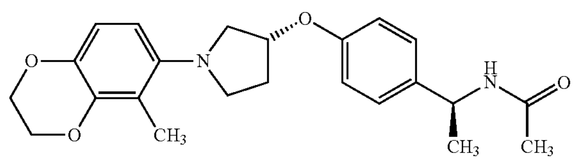 | A | 397 [M + H]+ | 1.21 (C) |
| 1.84 | VIII.1 + XVI.23 | 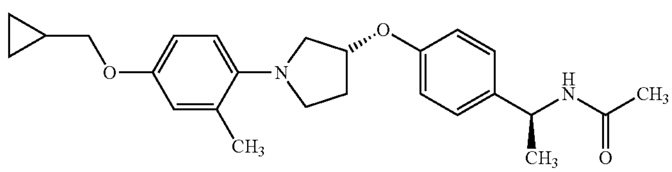 | A | 409 [M + H]+ | 1.28 (C) |
| 1.85 | VIII.1 + XVI.20 | 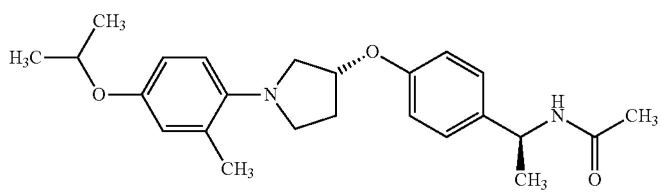 | A | 397 [M + H]+ | 1.25 (C) |
| 1.86 | VIII.1 + XVI.24 | 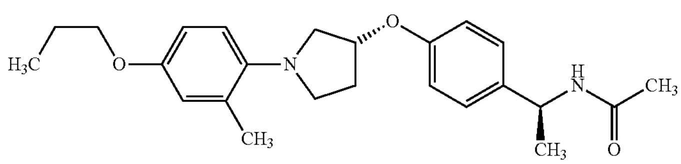 | A | 397 [M + H]+ | 1.22 (C) |
| 1.87 | VIII.1 + XVI.21 | 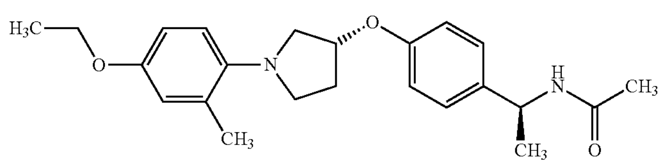 | A | 383 [M + H]+ | 1.22 (C) |
| 1.88 | VIII.1 + XVI.22 | 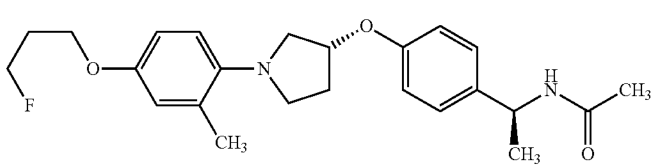 | A | 415 [M + H]+ | 1.22 (C) |

| Ex. | Starting material(s) | Structure | Method | Mass spec result | HPLC retention time (method) |
|---|---|---|---|---|---|
| 1.89 | VIII.1 + XVI.27 | 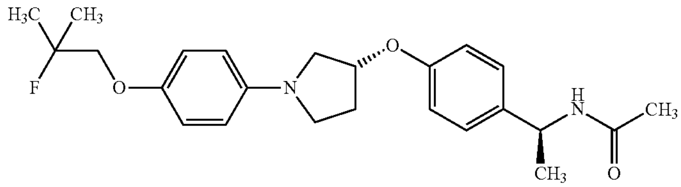 | A | 415 [M + H]+ | 1.16 (C) |
| 1.90 | VIII.1 + XXI | 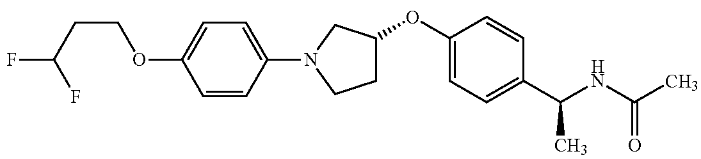 | A | 419 [M + H]+ | 1.13 (C) |
| 1.91 | VIII.1 + XVI.25 | 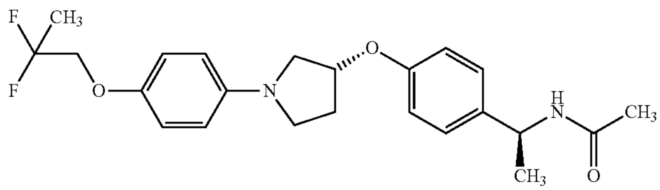 | A | 418 [M + H]+ | 1.02 (C) |
| 1.92 | VIII.1 | 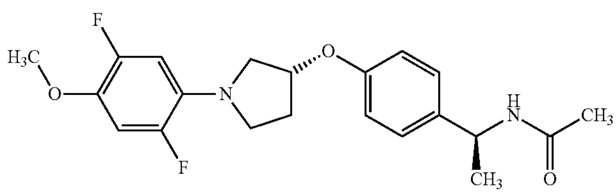 | B | 391 [M + H]+ | 1.05 (M) |
| 1.93 | VIII.1 | 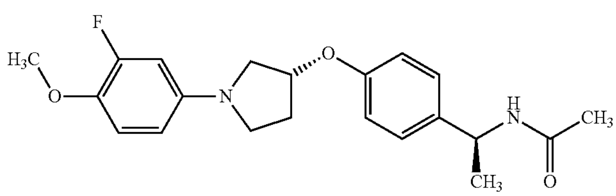 | B | 373 [M + H]+ | 1.02 (M) |
| 1.94 | VIII.1 | 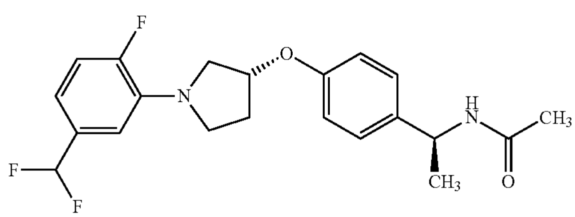 | B | 393 [M + H]+ | 1.08 (M) |
| 1.95 | VIII.1 + XXXI | 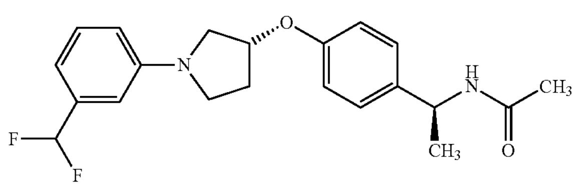 | B | 375 [M + H]+ | 1.06 (M) |
| 1.96 | VIII.1 + XVI.28 | 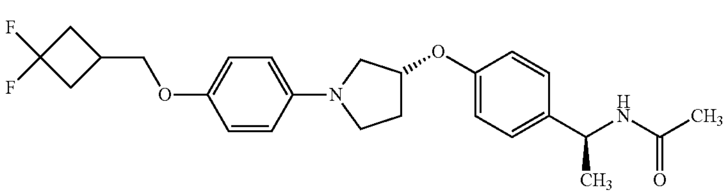 | A | 445 [M + H]+ | 1.17 (U) |

-continued

| Ex. | Starting material(s) | Structure | Method | Mass spec result | HPLC retention time (method) |
|---|---|---|---|---|---|
| 1.97 | VIII.1 + XVI.29 | 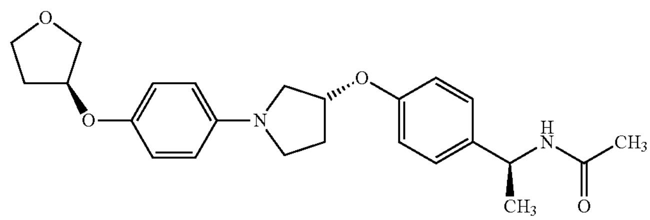 | A | 411 [M + H]+ | 0.86 (K) |
| 1.98 | VIII.1 + XVI.30 | 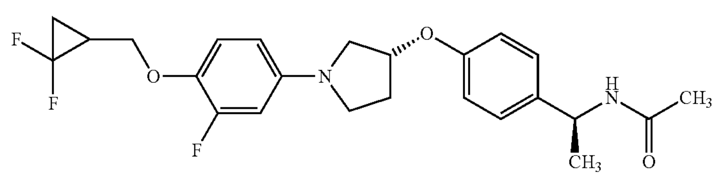 | A | 449 [M + H]+ | 1.10 (D) |
| 1.99 | VIII.1 + XVI.31 | 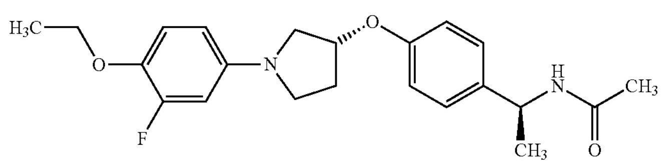 | A | 387 [M + H]+ | 1.08 (D) |
| 1.100 | VIII.1 + XVI.32 | 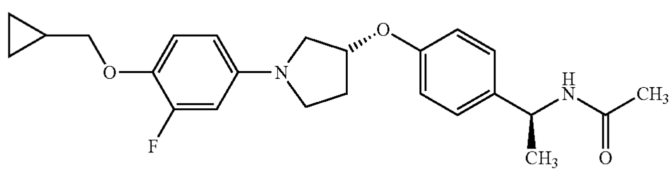 | A | 413 [M + H]+ | 1.12 (D) |
| 1.101 | VIII.1 | 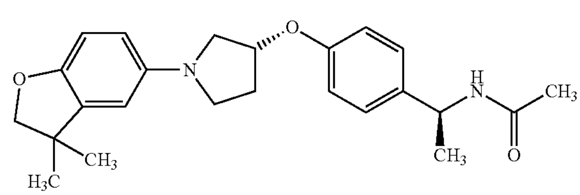 | A | 395 [M + H]+ | 0.89 (W) |
| 1.102 | XV + XXI | 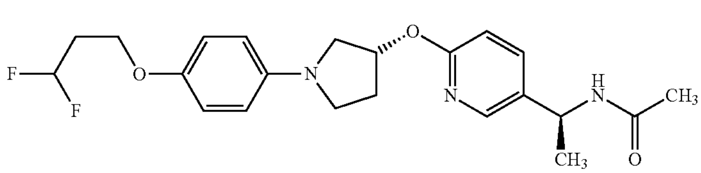 | A | 420 [M + H]+ | 0.69 (X) |

| Ex. | Starting material(s) | Structure | Method | Mass spec result | HPLC retention time (method) |
|---|---|---|---|---|---|
| 1.103 | XV + XVII.2 | 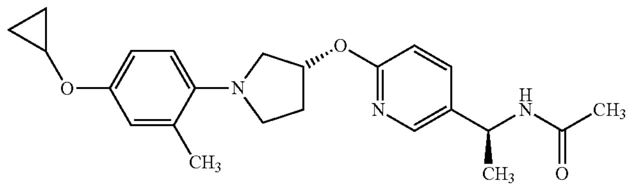 | A | 396 [M + H]⁺ | 0.57 (X) |
| 1.104 | VIII.2 + XVII.2 | 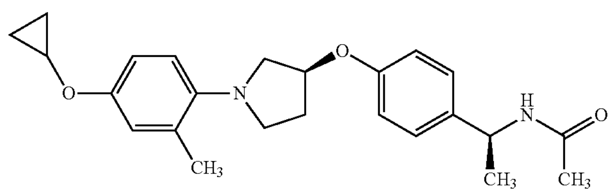 [SMILES: CC(=O)N[C@@H](C)c1ccc(O[C@H]2CCN(c3ccc(OC4CC4)cc3C)C2)cc1] | A | 395 [M + H]⁺ | 0.88 (M) |

*The product is a mixture of the two trans diastereoisomers regarding the 3 and 4 position of the pyrrolidine.
**The product is a mixture of the two cis diastereoisomers regarding the 3 and 4 position of the pyrrolidine.
***2-chloro-1-iodo-propoxy-benzene can be prepared as described in WO2012/028676.

Example 2

Example 2.1

General Route

2-Acetamido-N—((S)-1-(4-((R)-1-(4-(cyclopropyl-methoxy)phenyl)pyrrolidin-3-yloxy)phenyl)ethyl-4-methylthiazole-5-carboxamide

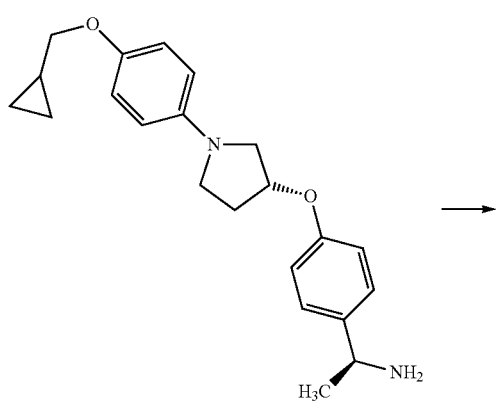

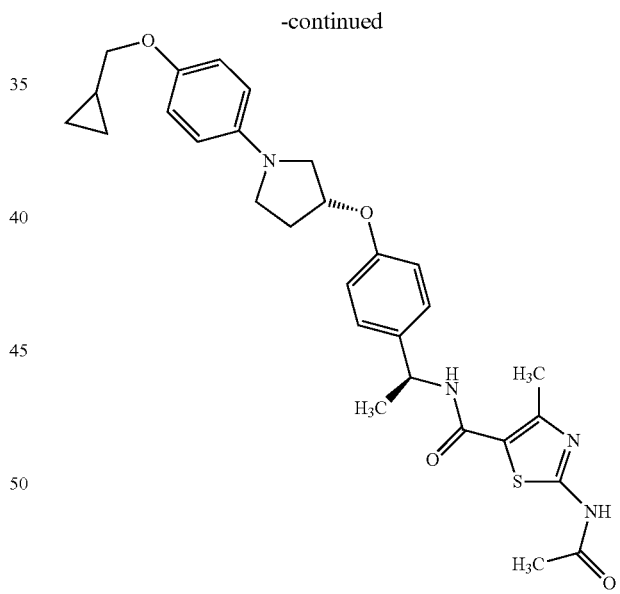

56.8 mg (0.28 mmol) 2-acetylamino-4-methyl-thiazole-5-carboxylic acid, 150 µl (0.85 mmol) DIPEA and 91.1 mg (0.28 mmol) TBTU are added to 2 ml DMF and stirred for 10 min. Then 100 mg (0.28 mmol) of the amine XXII.3 are added and the resulting mixture is stirred at r.t. over night. Afterwards the mixture is directly purified by HPLC (MeOH/H₂O/NH₃).
$C_{29}H_{34}N_4O_4S$ (M=534.7 g/mol)
ESI-MS: 535 [M+H]⁺
$R_t$ (HPLC): 1.20 min (method C)
The following compounds are prepared analogously to example 2.1.

For the examples CIP is used as coupling reagent the solvent is ACN.

For the examples in which 1-chloro-N,N-2-trimethylpropenylamine is used, the reagent is added to the a mixture of the appropiate acid in DCM and the mixture is stirred at r.t. for 30 min. Then the appropriate amine and DIPEA are added and the resulting mixture is stirred at r.t. for 1 h. After aq. work up the crude product is purified by HPLC.

For example 2.55 N-methylmorpholine is used as base.

For examples 2.57 and 2.63 the protection group is finally removed by using aq. HCl.

| Ex. | Starting material(s) | Coupling reagent | Structure | Mass spec result | HPLC retention time (method) |
|---|---|---|---|---|---|
| 2.1 | XXII.3 | TBTU | 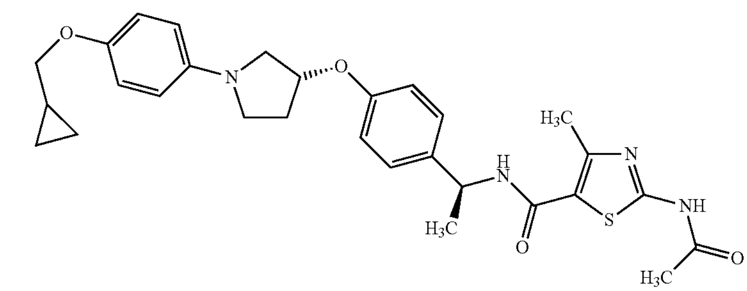 | 535 [M + H]⁺ | 1.20 (C) |
| 2.2 | XXII.3 | TBTU | 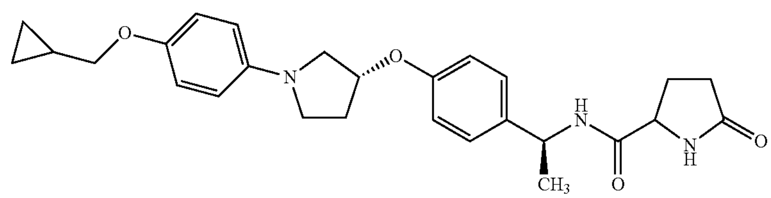 [SMILES: C[C@H](NC(=O)C1CCC(=O)N1)c1ccc(O[C@@H]2CCN(c3ccc(OCC4CC4)cc3)C2)cc1] | 464 [M + H]⁺ | 0.61 (O) |
| 2.3 | XXII.3 | TBTU | 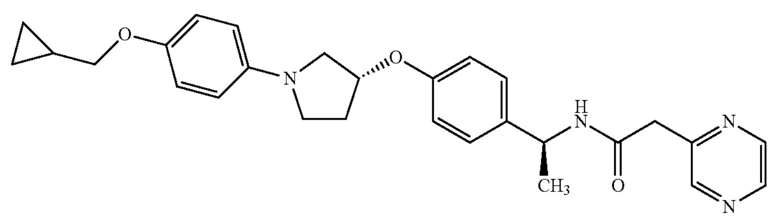 [SMILES: C[C@H](NC(=O)Cc1cnccn1)c1ccc(O[C@@H]2CCN(c3ccc(OCC4CC4)cc3)C2)cc1] | 473 [M + H]⁺ | 0.61 (O) |
| 2.4 | XXII.3 | TBTU | 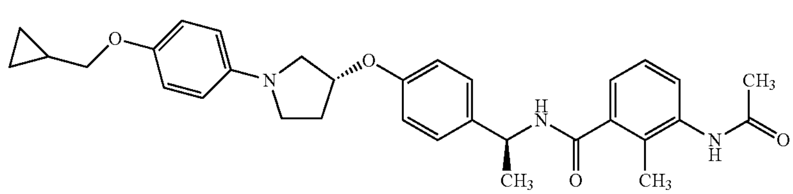 [SMILES: CC(=O)Nc1cccc(C(=O)N[C@@H](C)c2ccc(O[C@@H]3CCN(c4ccc(OCC5CC5)cc4)C3)cc2)c1C] | 528 [M + H]⁺ | 0.61 (O) |
| 2.5 | XXII.3 | TBTU | 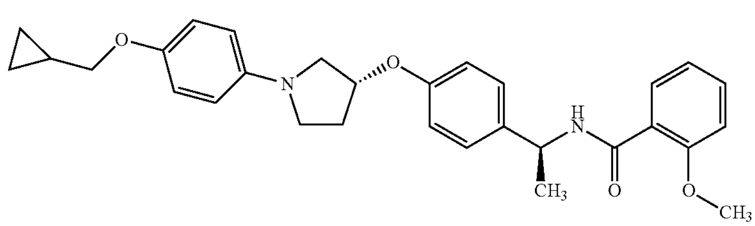 [SMILES: COc1ccccc1C(=O)N[C@@H](C)c1ccc(O[C@@H]2CCN(c3ccc(OCC4CC4)cc3)C2)cc1] | 487 [M + H]⁺ | 0.65 (O) |

| Ex. | Starting material(s) | Coupling reagent | Structure | Mass spec result | HPLC retention time (method) |
|---|---|---|---|---|---|
| 2.6 | XXII.3 | TBTU | 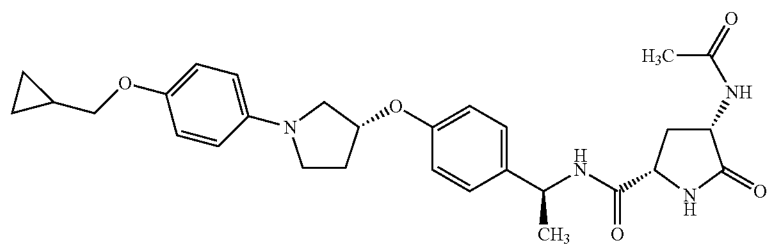 [SMILES: CC(=O)N[C@H]1C[C@@H](C(=O)N[C@@H](C)c2ccc(O[C@@H]3CCN(c4ccc(OCC5CC5)cc4)C3)cc2)NC1=O] | 521 [M + H]+ | 0.60 (O) |
| 2.7 | XXII.3 | TBTU | 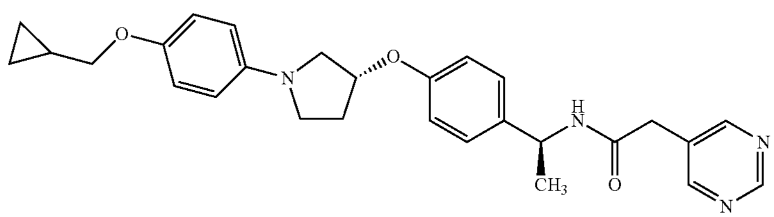 [SMILES: C[C@H](NC(=O)Cc1cncnc1)c1ccc(O[C@@H]2CCN(c3ccc(OCC4CC4)cc3)C2)cc1] | 473 [M + H]+ | 0.61 (O) |
| 2.8 | XXII.3 | TBTU | 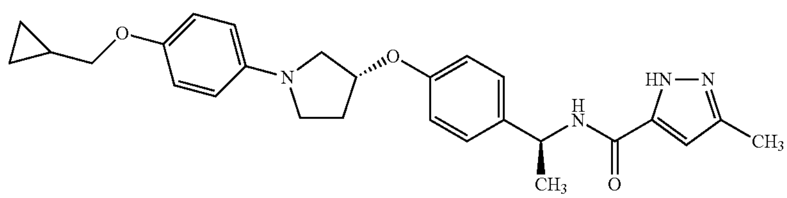 [SMILES: Cc1cc(C(=O)N[C@@H](C)c2ccc(O[C@@H]3CCN(c4ccc(OCC5CC5)cc4)C3)cc2)[nH]n1] | 461 [M + H]+ | 0.63 (O) |
| 2.9 | XXII.3 | TBTU | 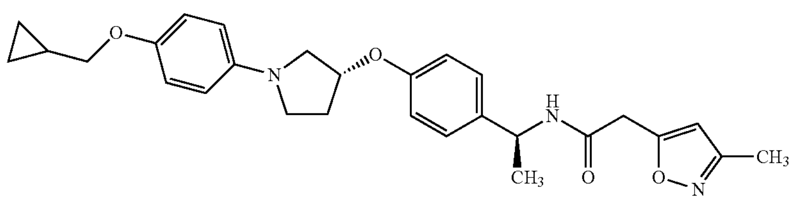 [SMILES: Cc1cc(CC(=O)N[C@@H](C)c2ccc(O[C@@H]3CCN(c4ccc(OCC5CC5)cc4)C3)cc2)on1] | 476 [M + H]+ | 0.62 (O) |
| 2.10 | XXII.3 | TBTU | 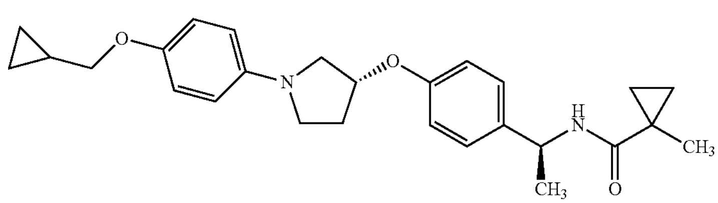 [SMILES: C[C@H](NC(=O)C1(C)CC1)c1ccc(O[C@@H]2CCN(c3ccc(OCC4CC4)cc3)C2)cc1] | 435 [M + H]+ | 0.64 (O) |
| 2.11 | XXII.3 | CIP | 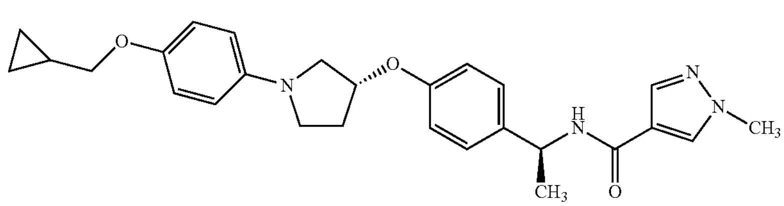 [SMILES: C[C@H](NC(=O)c1cnn(C)c1)c1ccc(O[C@@H]2CCN(c3ccc(OCC4CC4)cc3)C2)cc1] | 461 [M + H]+ | 0.61 (O) |

-continued

| Ex. | Starting material(s) | Coupling reagent | Structure | Mass spec result | HPLC retention time (method) |
|---|---|---|---|---|---|
| 2.12 | XXII.3 | Pybop | 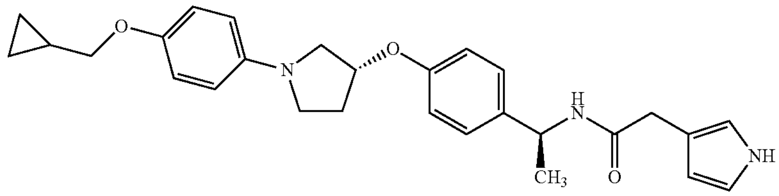 [SMILES: C[C@H](NC(=O)Cc1cc[nH]c1)c1ccc(O[C@@H]2CCN(c3ccc(OCC4CC4)cc3)C2)cc1] | 460 [M + H]+ | 0.62 (O) |
| 2.13 | XXII.3 | TBTU | 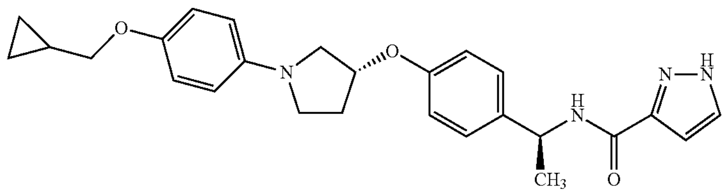 [SMILES: C[C@H](NC(=O)c1cc[nH]n1)c1ccc(O[C@@H]2CCN(c3ccc(OCC4CC4)cc3)C2)cc1] | 447 [M + H]+ | 0.62 (O) |
| 2.14 | XXII.3 | TBTU | 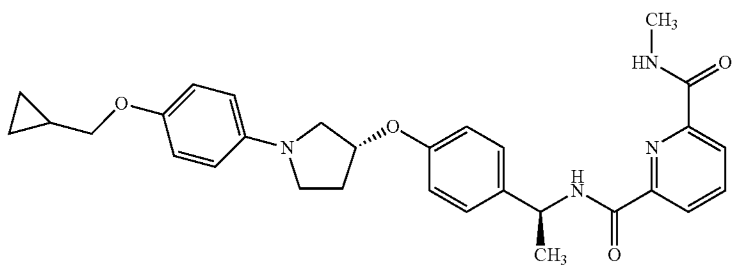 [SMILES: CNC(=O)c1cccc(C(=O)N[C@@H](C)c2ccc(O[C@@H]3CCN(c4ccc(OCC5CC5)cc4)C3)cc2)n1] | 515 [M + H]+ | 0.63 (O) |
| 2.15 | XXII.3 | TBTU | 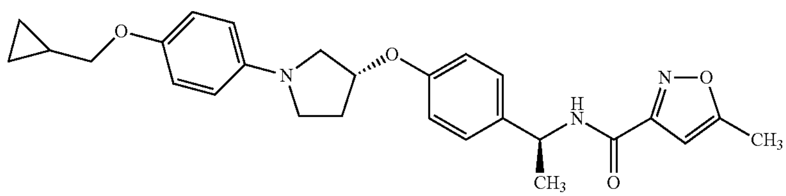 [SMILES: Cc1cc(C(=O)N[C@@H](C)c2ccc(O[C@@H]3CCN(c4ccc(OCC5CC5)cc4)C3)cc2)no1] | 462 [M + H]+ | 0.63 (O) |
| 2.16 | XXII.3 | TBTU | 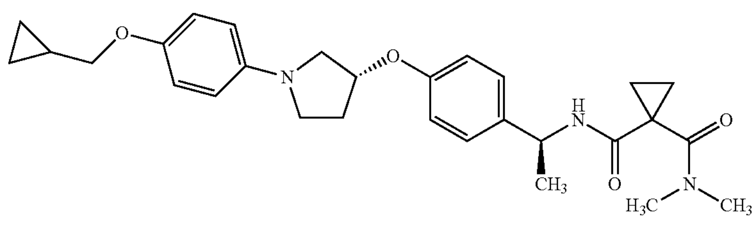 [SMILES: C[C@H](NC(=O)C1(C(=O)N(C)C)CC1)c1ccc(O[C@@H]2CCN(c3ccc(OCC4CC4)cc3)C2)cc1] | 492 [M + H]+ | 0.62 (O) |
| 2.17 | XXII.3 | TBTU | 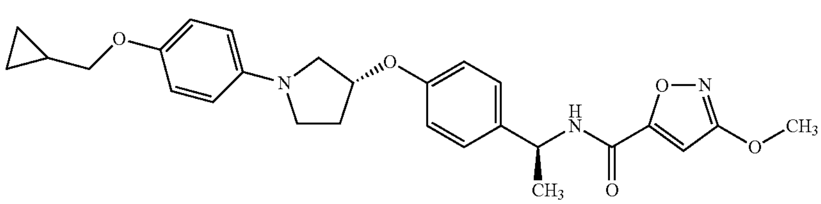 [SMILES: COc1cc(C(=O)N[C@@H](C)c2ccc(O[C@@H]3CCN(c4ccc(OCC5CC5)cc4)C3)cc2)on1] | 478 [M + H]+ | 0.63 (O) |

-continued
| Ex. | Starting material(s) | Coupling reagent | Structure | Mass spec result | HPLC retention time (method) |
|---|---|---|---|---|---|
| 2.18 | XXII.3 | TBTU | 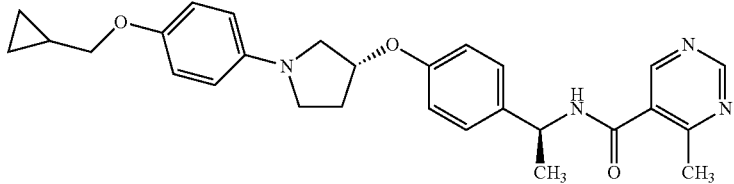 [SMILES: Cc1ncncc1C(=O)N[C@@H](C)c1ccc(O[C@@H]2CCN(c3ccc(OCC4CC4)cc3)C2)cc1] | 473 [M + H]+ | 0.61 (O) |
| 2.19 | XXIII | TBTU | 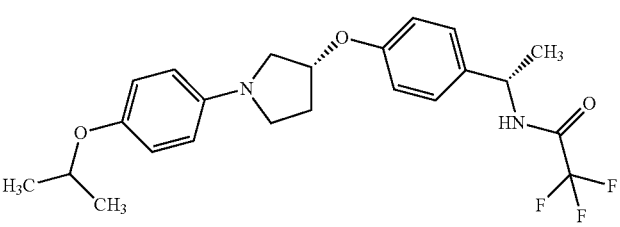 [SMILES: CC(C)Oc1ccc(N2CC[C@@H](Oc3ccc([C@H](C)NC(=O)C(F)(F)F)cc3)C2)cc1] | 437 [M + H]+ | 1.42 (Q) |
| 2.20 | XXIII | TBTU | 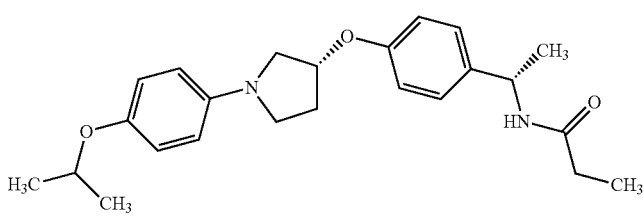 [SMILES: CCC(=O)N[C@@H](C)c1ccc(O[C@@H]2CCN(c3ccc(OC(C)C)cc3)C2)cc1] | 397 [M + H]+ | 1.28 (Q) |
| 2.21 | XXII.3 | CIP | 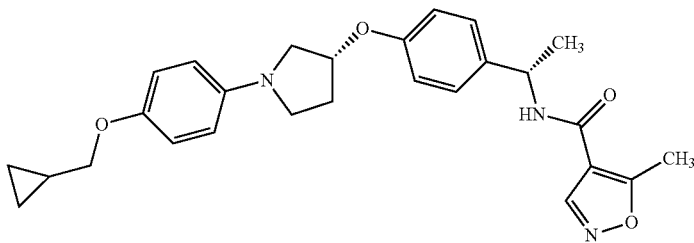 [SMILES: Cc1oncc1C(=O)N[C@@H](C)c1ccc(O[C@@H]2CCN(c3ccc(OCC4CC4)cc3)C2)cc1] | 462 [M + H]+ | 1.35 (Q) |
| 2.22 | XXII.3 | CIP | 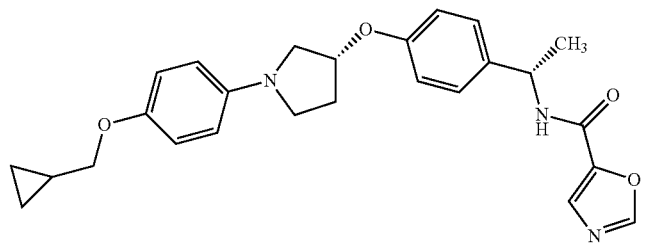 [SMILES: C[C@H](NC(=O)c1cnco1)c1ccc(O[C@@H]2CCN(c3ccc(OCC4CC4)cc3)C2)cc1] | 448 [M + H]+ | 1.25 (Q) |
| 2.23 | XXII.3 | CIP | 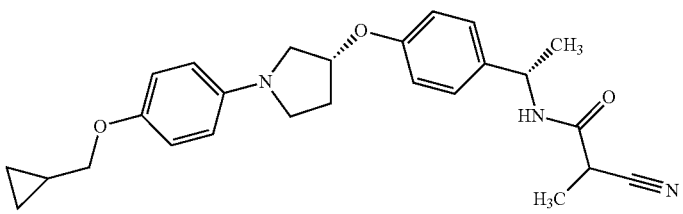 [SMILES: CC(C#N)C(=O)N[C@@H](C)c1ccc(O[C@@H]2CCN(c3ccc(OCC4CC4)cc3)C2)cc1] | 434 [M + H]+ | 1.31 (Q) |

-continued

| Ex. | Starting material(s) | Coupling reagent | Structure | Mass spec result | HPLC retention time (method) |
|---|---|---|---|---|---|
| 2.24 | XXII.3 | CIP | 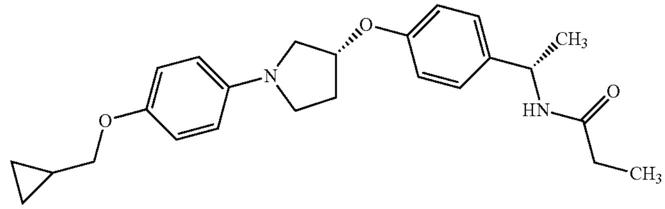 [SMILES: CCC(=O)N[C@@H](C)c1ccc(O[C@@H]2CCN(c3ccc(OCC4CC4)cc3)C2)cc1] | 409 [M + H]⁺ | 1.29 (Q) |
| 2.25 | XXII.3 | CIP | 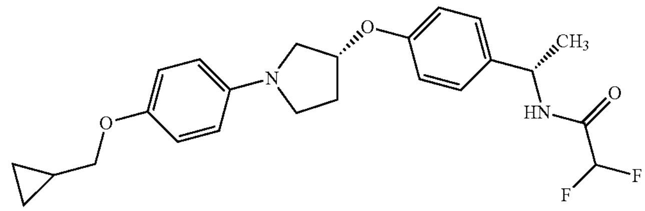 [SMILES: C[C@H](NC(=O)C(F)F)c1ccc(O[C@@H]2CCN(c3ccc(OCC4CC4)cc3)C2)cc1] | 431 [M + H]⁺ | 1.34 (Q) |
| 2.26 | XXII.3 | Pybop | 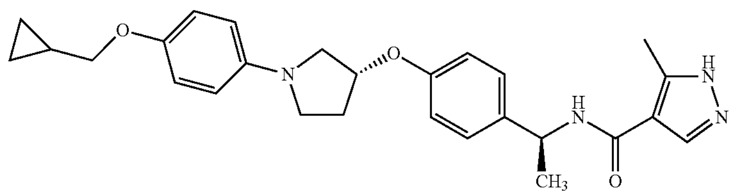 [SMILES: Cc1[nH]ncc1C(=O)N[C@@H](C)c1ccc(O[C@@H]2CCN(c3ccc(OCC4CC4)cc3)C2)cc1] | 461 [M + H]⁺ | 0.88 (D) |
| 2.27 | XXII.3 | TBTU | 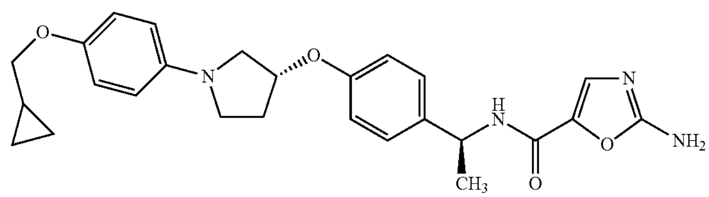 [SMILES: C[C@H](NC(=O)c1cnc(N)o1)c1ccc(O[C@@H]2CCN(c3ccc(OCC4CC4)cc3)C2)cc1] | 463 [M + H]⁺ | 1.16 (C) |
| 2.28 | XXII.3 | CIP | 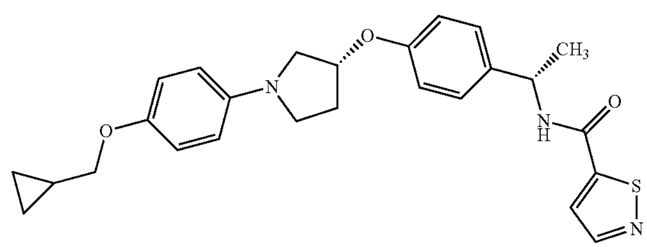 [SMILES: C[C@H](NC(=O)c1ccns1)c1ccc(O[C@@H]2CCN(c3ccc(OCC4CC4)cc3)C2)cc1] | 464 [M + H]⁺ | 1.49 (R) |
| 2.29 | XXII.3 | BOP | 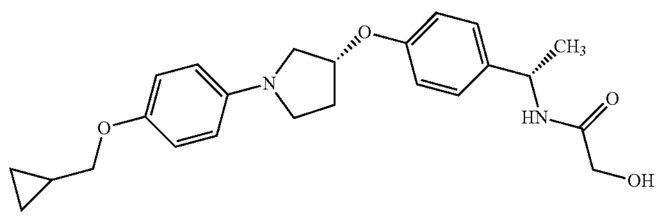 [SMILES: C[C@H](NC(=O)CO)c1ccc(O[C@@H]2CCN(c3ccc(OCC4CC4)cc3)C2)cc1] | 411 [M + H]⁺ | 1.38 (R) |

-continued

| Ex. | Starting material(s) | Coupling reagent | Structure | Mass spec result | HPLC retention time (method) |
|---|---|---|---|---|---|
| 2.30 | XXII.3 | Pybop | 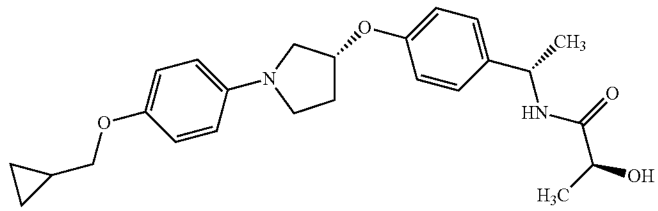 [SMILES: C[C@H](O)C(=O)N[C@@H](C)c1ccc(O[C@@H]2CCN(c3ccc(OCC4CC4)cc3)C2)cc1] | 425 [M + H]+ | 1.35 (H) |
| 2.31 | XXII.3 | Pybop | 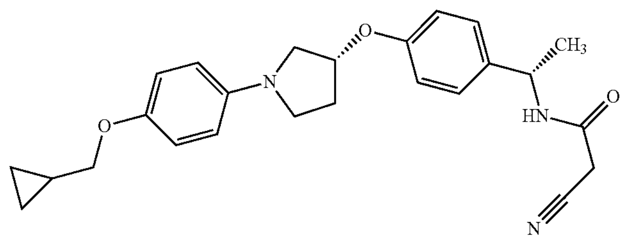 [SMILES: C[C@H](NC(=O)CC#N)c1ccc(O[C@@H]2CCN(c3ccc(OCC4CC4)cc3)C2)cc1] | 420 [M + H]+ | 1.32 (H) |
| 2.32 | XXII.3 | Pybop | 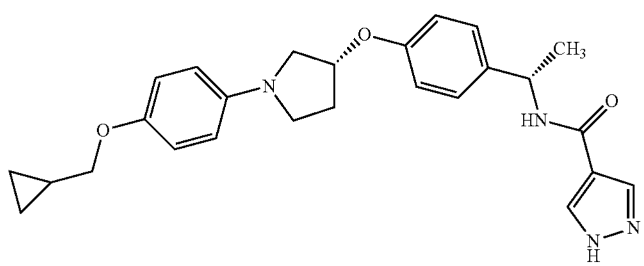 [SMILES: C[C@H](NC(=O)c1cn[nH]c1)c1ccc(O[C@@H]2CCN(c3ccc(OCC4CC4)cc3)C2)cc1] | 446 [M + H]+ | 0.93 (K) |
| 2.33 | XXII.3 | Pybop | 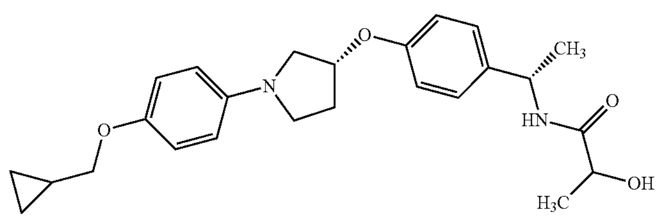 [SMILES: CC(O)C(=O)N[C@@H](C)c1ccc(O[C@@H]2CCN(c3ccc(OCC4CC4)cc3)C2)cc1] | 425 [M + H]+ | 1.26 (H) |
| 2.34 | XXII.3 | CIP | 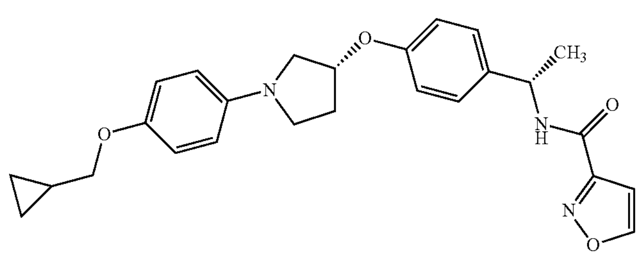 [SMILES: C[C@H](NC(=O)c1ccon1)c1ccc(O[C@@H]2CCN(c3ccc(OCC4CC4)cc3)C2)cc1] | 448 [M + H]+ | 1.02 (K) |
| 2.35 | XXII.3 | CIP | 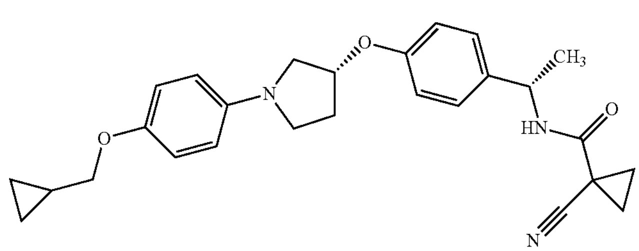 [SMILES: C[C@H](NC(=O)C1(C#N)CC1)c1ccc(O[C@@H]2CCN(c3ccc(OCC4CC4)cc3)C2)cc1] | 446 [M + H]+ | 1.48 (R) |

-continued

| Ex. | Starting material(s) | Coupling reagent | Structure | Mass spec result | HPLC retention time (method) |
|---|---|---|---|---|---|
| 2.36 | XXII.3 | CIP | 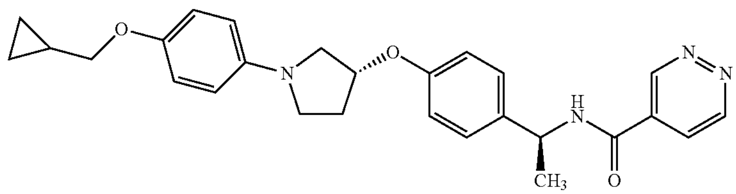 [SMILES: C[C@H](NC(=O)c1ccnnc1)c1ccc(O[C@@H]2CCN(c3ccc(OCC4CC4)cc3)C2)cc1] | 459 [M + H]+ | 1.41 (R) |
| 2.37 | XXII.3 | CIP | 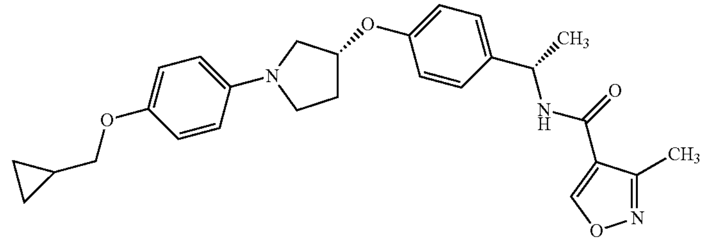 [SMILES: Cc1nocc1C(=O)N[C@@H](C)c1ccc(O[C@@H]2CCN(c3ccc(OCC4CC4)cc3)C2)cc1] | 462 [M + H]+ | 1.48 (R) |
| 2.38 | XXII.3 | Pybop | 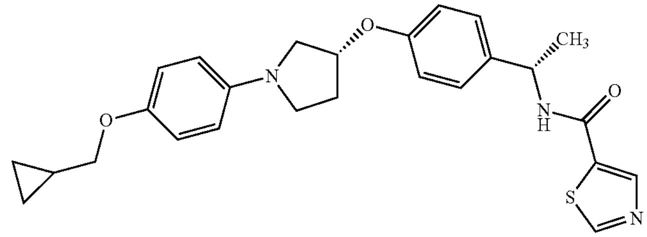 [SMILES: C[C@H](NC(=O)c1cncs1)c1ccc(O[C@@H]2CCN(c3ccc(OCC4CC4)cc3)C2)cc1] | 464 [M + H]+ | 1.46 (R) |
| 2.39 | XXII.3 | CIP | 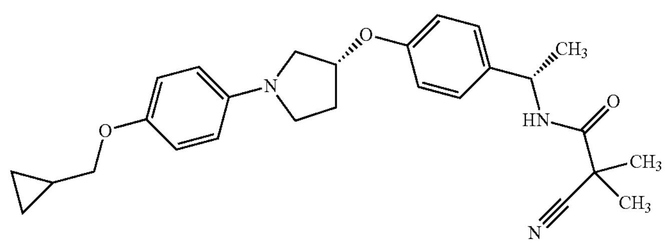 [SMILES: C[C@H](NC(=O)C(C)(C)C#N)c1ccc(O[C@@H]2CCN(c3ccc(OCC4CC4)cc3)C2)cc1] | 448 [M + H]+ | 1.50 (R) |
| 2.40 | XXII.1 | TBTU | 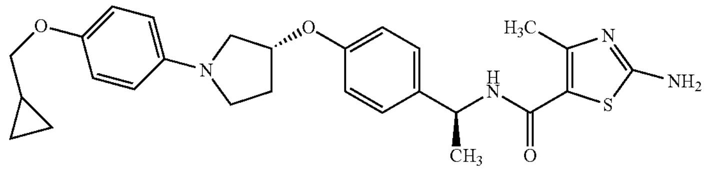 [SMILES: Cc1nc(N)sc1C(=O)N[C@@H](C)c1ccc(O[C@@H]2CCN(c3ccc(OCC4CC4)cc3)C2)cc1] | 493 [M + H]+ | 1.20 (E) |
| 2.41 | XXII.3 | TBTU | 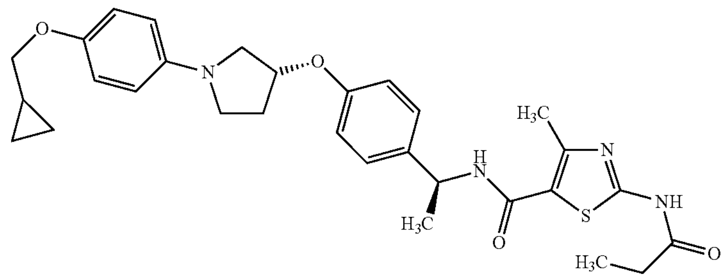 | 549 [M + H]+ | 1.35 (E) |

-continued
| Ex. | Starting material(s) | Coupling reagent | Structure | Mass spec result | HPLC retention time (method) |
|---|---|---|---|---|---|
| 2.42 | XXII.1 | 1-chloro-N,N-2-tri-methyl-pro-penyl-amine | 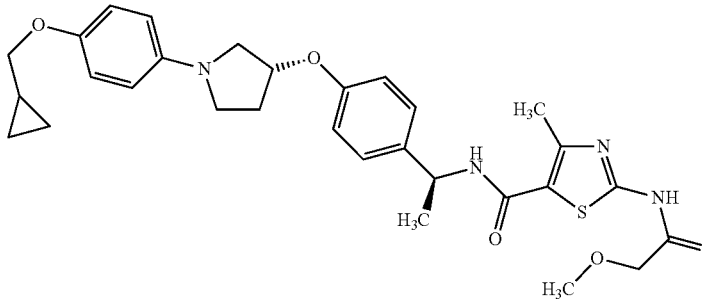 | 565 [M + H]$^+$ | 0.87 (K) |
| 2.43 | XXII.1 | TBTU | 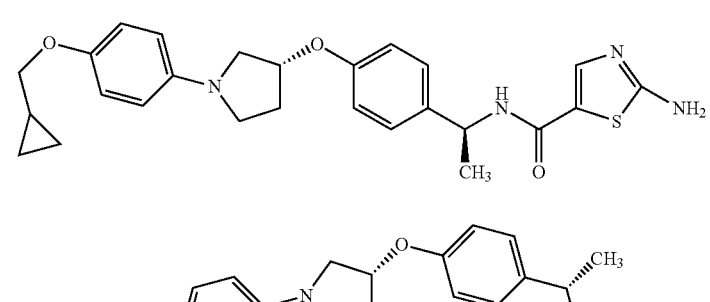 | 479 [M + H]$^+$ | 1.21 (E) |
| 2.44 | XXII.3 | CIP | 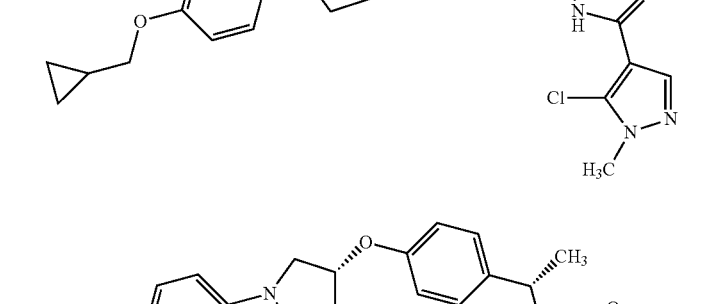 | 495 [M + H]$^+$ | 0.96 (D) |
| 2.45 | XXII.3 | CIP | 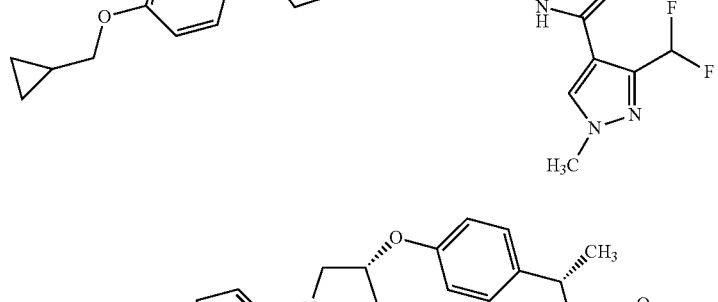 | 511 [M + H]$^+$ | 0.96 (D) |
| 2.46 | XXII.3 | CIP | 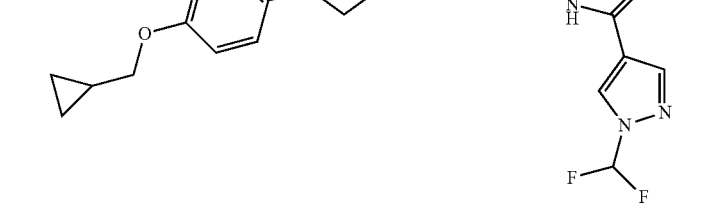 | 497 [M + H]$^+$ | 0.95 (D) |

-continued

| Ex. | Starting material(s) | Coupling reagent | Structure | Mass spec result | HPLC retention time (method) |
|---|---|---|---|---|---|
| 2.47 | XXII.3 | CIP | 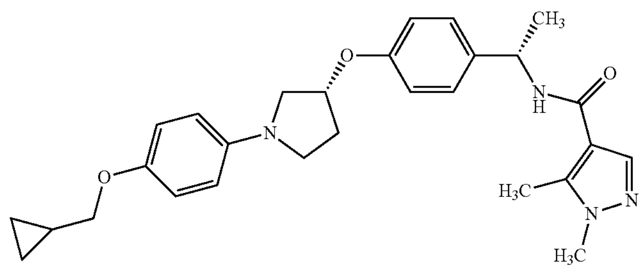 [SMILES: Cc1c(C(=O)N[C@@H](C)c2ccc(O[C@@H]3CCN(c4ccc(OCC5CC5)cc4)C3)cc2)cnn1C] | 475 [M + H]$^+$ | 0.91 (D) |
| 2.48 | XXII.3 | Pybop | 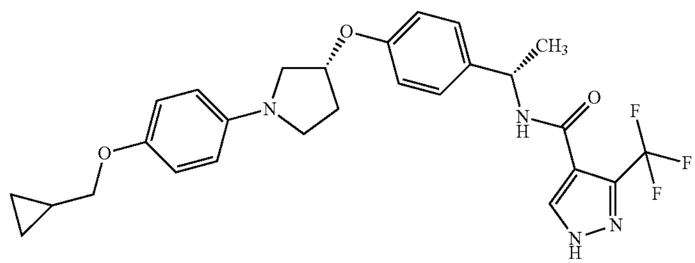 [SMILES: C[C@H](NC(=O)c1c[nH]nc1C(F)(F)F)c1ccc(O[C@@H]2CCN(c3ccc(OCC4CC4)cc3)C2)cc1] | 515 [M + H]$^+$ | 0.96 (D) |
| 2.49 | XXII.3 | CIP | 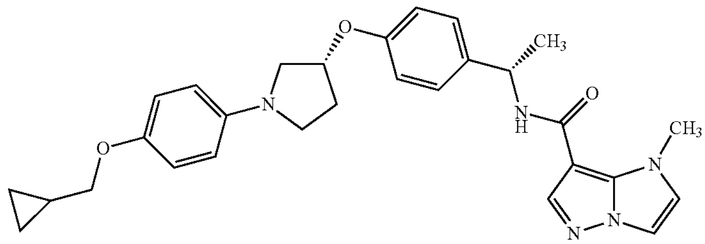 [SMILES: C[C@H](NC(=O)c1cnn2ccn(C)c12)c1ccc(O[C@@H]2CCN(c3ccc(OCC4CC4)cc3)C2)cc1] | 500 [M + H]$^+$ | 0.91 (D) |
| 2.50 | XXII.3 | TBTU | 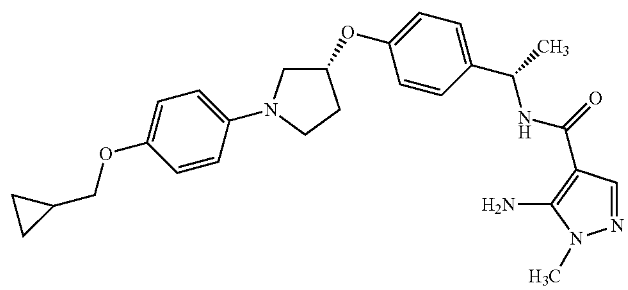 [SMILES: C[C@H](NC(=O)c1cnn(C)c1N)c1ccc(O[C@@H]2CCN(c3ccc(OCC4CC4)cc3)C2)cc1] | 476 [M + H]$^+$ | 0.88 (D) |
| 2.51 | XXII.3 | Pybop | 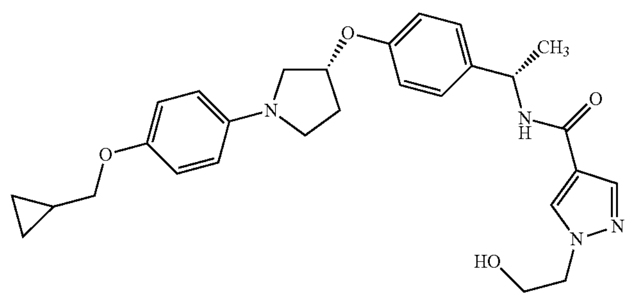 [SMILES: C[C@H](NC(=O)c1cnn(CCO)c1)c1ccc(O[C@@H]2CCN(c3ccc(OCC4CC4)cc3)C2)cc1] | 491 [M + H]$^+$ | 0.92 (H) |

-continued
| Ex. | Starting material(s) | Coupling reagent | Structure | Mass spec result | HPLC retention time (method) |
|---|---|---|---|---|---|
| 2.52 | XXII.3 | CIP | 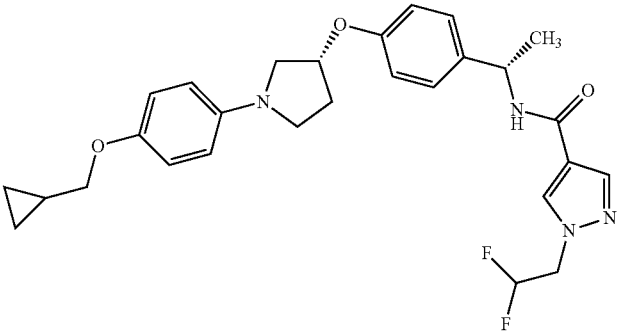 [SMILES: C[C@H](NC(=O)c1cnn(CC(F)F)c1)c1ccc(O[C@@H]2CCN(c3ccc(OCC4CC4)cc3)C2)cc1] | 511 [M + H]⁺ | 0.98 (K) |
| 2.53 | XXII.3 | CIP | 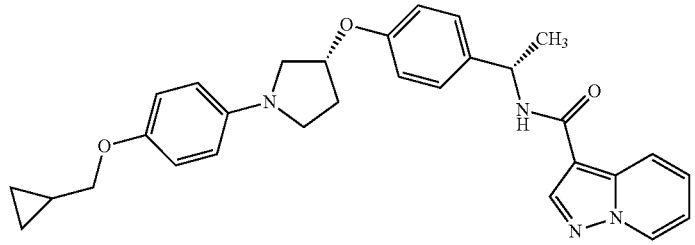 [SMILES: C[C@H](NC(=O)c1cnn2ccccc12)c1ccc(O[C@@H]2CCN(c3ccc(OCC4CC4)cc3)C2)cc1] | 498 [M + H]⁺ | 1.00 (K) |
| 2.54 | XXII.2 + XXX.1 | HATU | 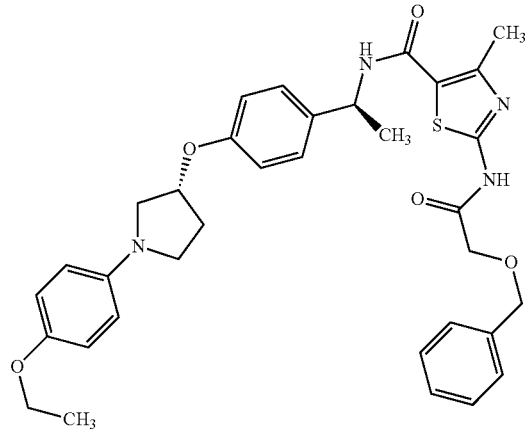 [SMILES: CCOc1ccc(N2CC[C@@H](Oc3ccc([C@H](C)NC(=O)c4sc(NC(=O)COCc5ccccc5)nc4C)cc3)C2)cc1] | 615 [M + H]⁺ | 1.12 (M) |
| 2.55 | XXII.2 + XXX.2 | TBTU | 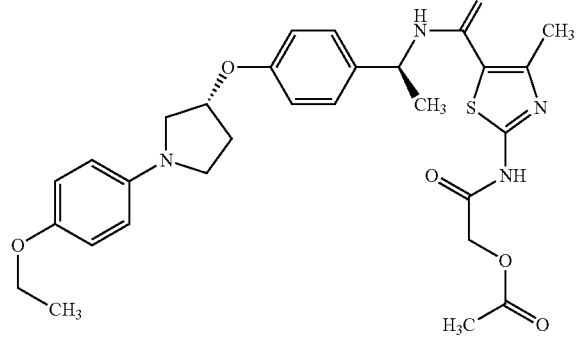 | 567 [M + H]⁺ | 1.09 (M) |

-continued

| Ex. | Starting material(s) | Coupling reagent | Structure | Mass spec result | HPLC retention time (method) |
|---|---|---|---|---|---|
| 2.56 | XXII.3+ | TBTU | 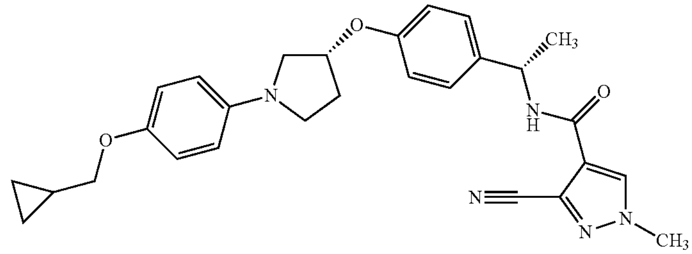 [SMILES: C[C@H](NC(=O)c1cn(C)nc1C#N)c1ccc(O[C@@H]2CCN(c3ccc(OCC4CC4)cc3)C2)cc1] | 486 [M + H]⁺ | 0.88 (D) |
| 2.57 | XXII.3 + XXXII.1 | TBTU | 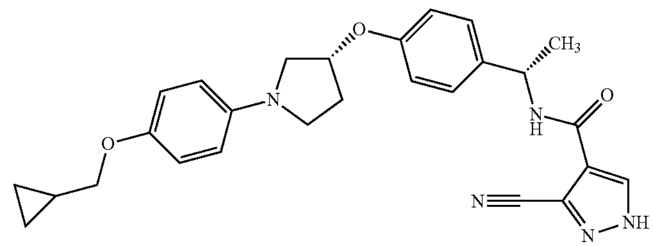 [SMILES: C[C@H](NC(=O)c1c[nH]nc1C#N)c1ccc(O[C@@H]2CCN(c3ccc(OCC4CC4)cc3)C2)cc1] | 472 [M + H]⁺ | 0.73 (K) |
| 2.58 | XXII.4 | TBTU | 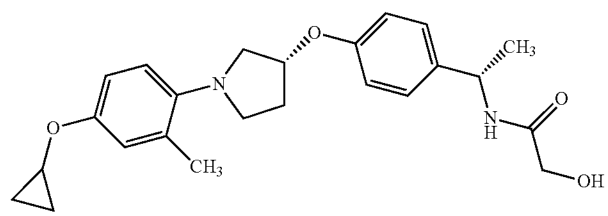 [SMILES: Cc1cc(OC2CC2)ccc1N1CC[C@@H](Oc2ccc([C@H](C)NC(=O)CO)cc2)C1] | 411 [M + H]⁺ | 0.95 (K) |
| 2.59 | XXII.4 | 1-chloro-N,N-2-tri-methyl-pro-penyl-amine | 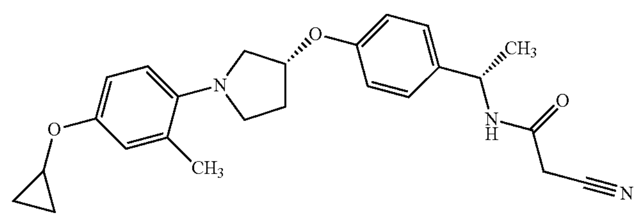 [SMILES: Cc1cc(OC2CC2)ccc1N1CC[C@@H](Oc2ccc([C@H](C)NC(=O)CC#N)cc2)C1] | 420 [M + H]⁺ | 1.01 (K) |
| 2.60 | XXII.4 | 1-chloro-N,N-2-tri-methyl-pro-penyl-amine | 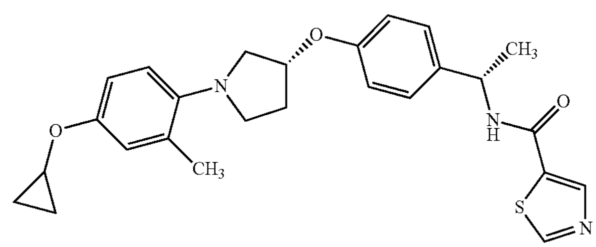 [SMILES: Cc1cc(OC2CC2)ccc1N1CC[C@@H](Oc2ccc([C@H](C)NC(=O)c3cncs3)cc2)C1] | 464 [M + H]⁺ | 1.01 (K) |
| 2.61 | XXII.4 | 1-chloro-N,N-2-tri-methyl-pro-penyl-amine | 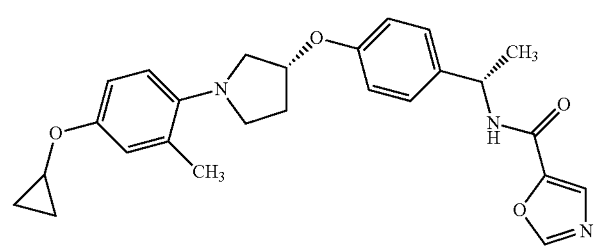 [SMILES: Cc1cc(OC2CC2)ccc1N1CC[C@@H](Oc2ccc([C@H](C)NC(=O)c3cnco3)cc2)C1] | 448 [M + H]⁺ | 0.99 (K) |

-continued

| Ex. | Starting material(s) | Coupling reagent | Structure | Mass spec result | HPLC retention time (method) |
|---|---|---|---|---|---|
| 2.62 | XXII.4 | 1-chloro-N,N-2-trimethyl-propenyl-amine | 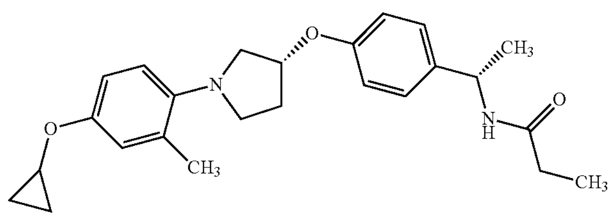 [SMILES: CCC(=O)N[C@@H](C)c1ccc(O[C@@H]2CCN(c3ccc(OC4CC4)cc3C)C2)cc1] | 409 [M + H]+ | 1.01 (K) |
| 2.63 | XXII.4 | 1-chloro-N,N-2-trimethyl-propenyl-amine | 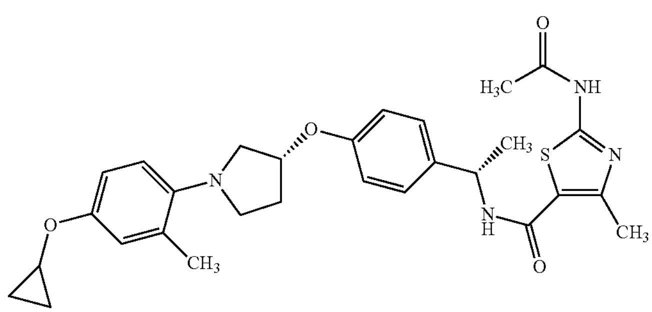 [SMILES: CC(=O)Nc1nc(C)c(C(=O)N[C@@H](C)c2ccc(O[C@@H]3CCN(c4ccc(OC5CC5)cc4C)C3)cc2)s1] | 535 [M + H]+ | 0.97 (K) |
| 2.64 | XXII.4 + XXXII.2 | TBTU | 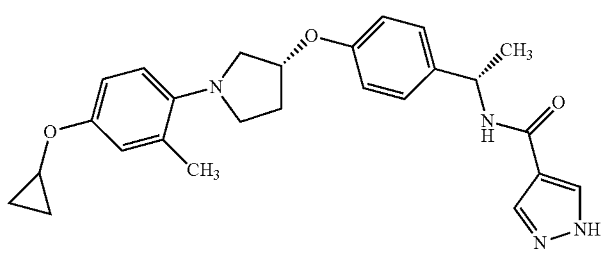 [SMILES: Cc1cc(OC2CC2)ccc1N1CC[C@@H](Oc2ccc([C@H](C)NC(=O)c3cn[nH]c3)cc2)C1] | 447 [M + H]+ | 0.95 (K) |
| 2.65 | XXII.4 | 1-chloro-N,N-2-trimethyl-propenyl-amine | 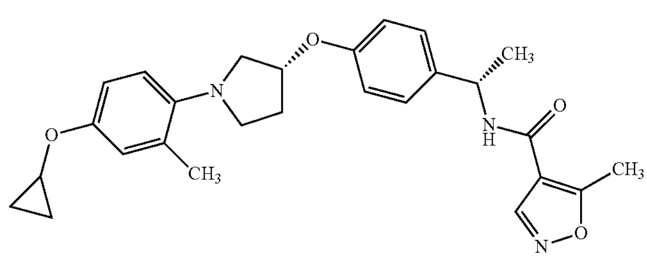 [SMILES: Cc1cc(OC2CC2)ccc1N1CC[C@@H](Oc2ccc([C@H](C)NC(=O)c3cnoc3C)cc2)C1] | 462 [M + H]+ | 1.04 (K) |

Example 3

Example 3.1

General Route 3-((S)-1-(4-((R)-1-(4-(cyclopropylmethoxy)phenyl)pyrrolidin-3-yloxy)phenyl)ethyl)-1,1-dimethylurea

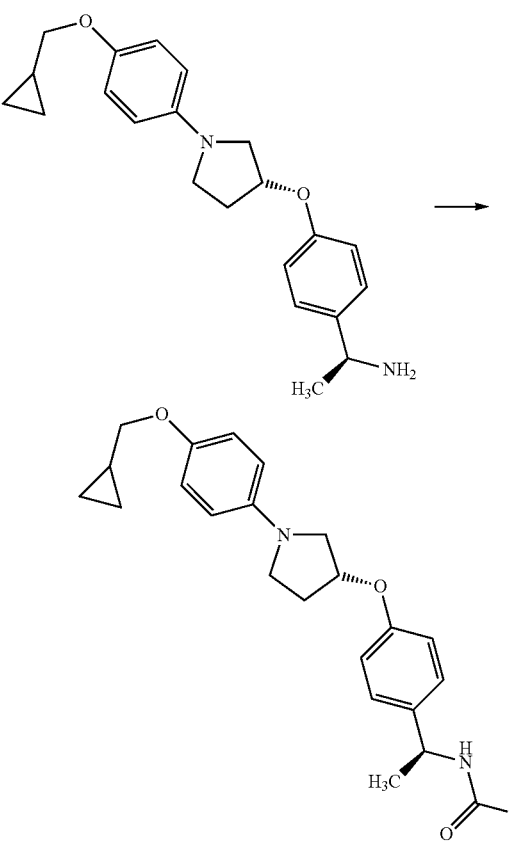

Method A)

To 300 mg (0.85 mmol) of amine XXII.3 and 0.29 mL (4.26 mmol) DIPEA in 3 mL THF are added 0.39 mL (4.26 mmol) dimethylcarbamoyl chloride and the resulting mixture is stirred at 60° C. for 2 h. After that some DMF is added and the mixture is directly purified by HPLC (MeOH/H$_2$O/TFA).

Method B)

To 35.2 mg (0.10 mmol) of amine XXII.3 in 1 mL dioxane are added 32.8 mg (0.20 mmol) CDT and 29.9 µL (0.20 mmol) DBU and the resulting mixture is stirred at r.t. for 5 min. Then 0.06 mL (0.20 mmol) of a dimethylamine solution in THF (c=2 mol/L) are added stirring is continued over night. The mixture is purified by HPLC (MeOH/H$_2$O/TFA).

$C_{25}H_{33}N_3O_3$ (M=423.6 g/mol)

ESI-MS: 424 [M+H]$^+$

R$_t$ (HPLC): 1.54 min (method R)

The following compounds are prepared analogously to example 3.1.

For the examples 3.2-3.6 TEA is used as base and DCM as solvent.

For example 3.7 CDT is reacted with 3-aminoisoxazole in presence of DBU for 15 min before the amine XXI.3 is added.

For the examples 3.8-3.11 the appropriate isocyanate is used and the reaction mixture is stirred at r.t. over night.

| Ex. | Starting material(s) | Structure | Method | Mass spec result | HPLC retention time (method) |
|---|---|---|---|---|---|
| 3.1 | XXII.3 | 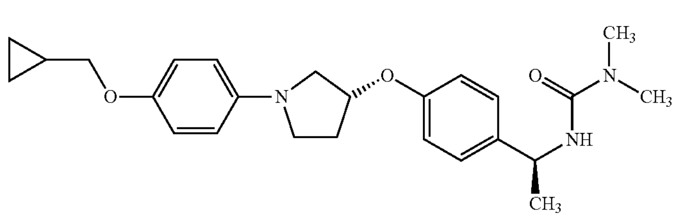 | A | 424 [M + H]$^+$ | 1.54 (R) |

| Ex. | Starting material(s) | Structure | Method | Mass spec result | HPLC retention time (method) |
|---|---|---|---|---|---|
| 3.2 | XXII.3 | 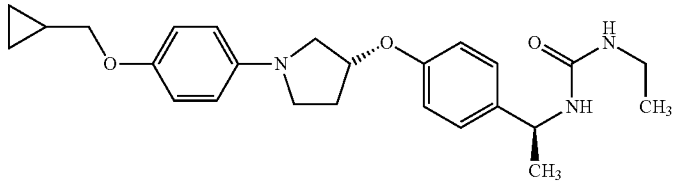 | B | 424 [M + H]+ | 1.19 (C) |
| 3.3 | XXII.3 | 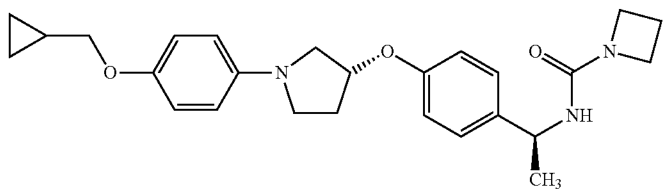 | B | 436 [M + H]+ | 1.19 (C) |
| 3.4 | XXII.3 | 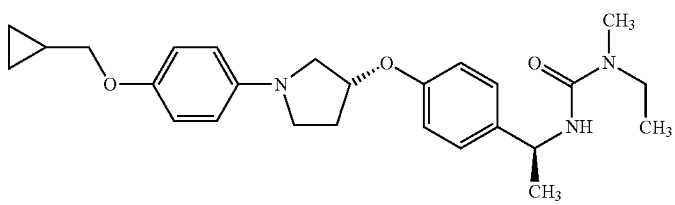 | B | 438 [M + H]+ | 1.22 (C) |
| 3.5 | XXII.3 | 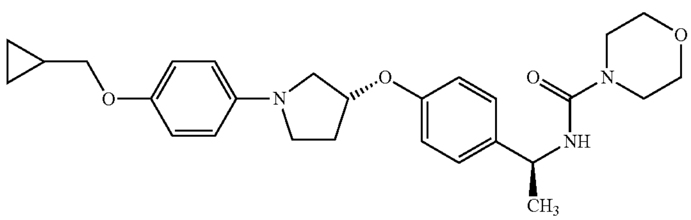 | B | 466 [M + H]+ | 1.18 (C) |
| 3.6 | XXII.3 | 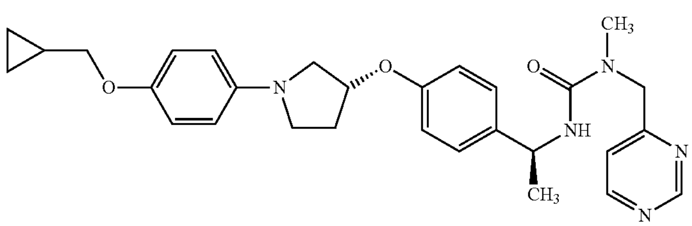 | B | 502 [M + H]+ | 1.18 (C) |
| 3.7 | XXII.3 | 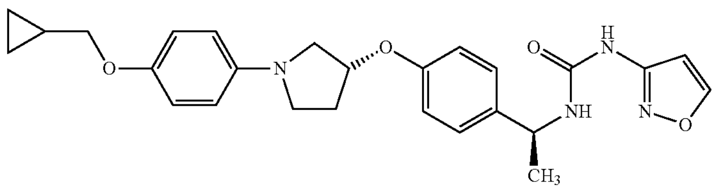 | B | 463 [M + H]+ | 1.28 (B) |
| 3.8 | XXII.3 | 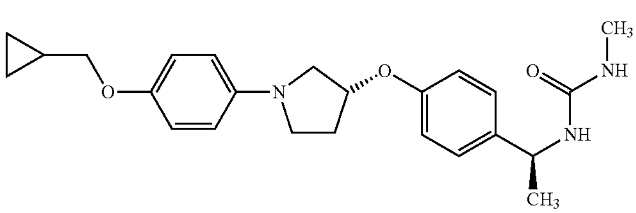 | A | 410 [M + H]+ | 1.20 (Q) |

-continued

| Ex. | Starting material(s) | Structure | Method | Mass spec result | HPLC retention time (method) |
|---|---|---|---|---|---|
| 3.9 | XXIII | 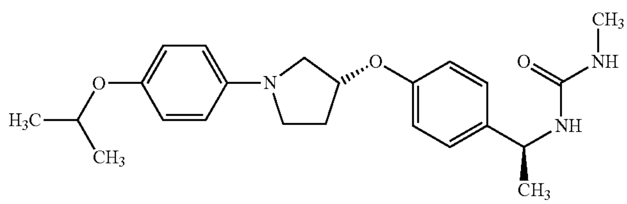 | A | 398 [M + H]+ | 1.19 (Q) |
| 3.10 | XXIII | 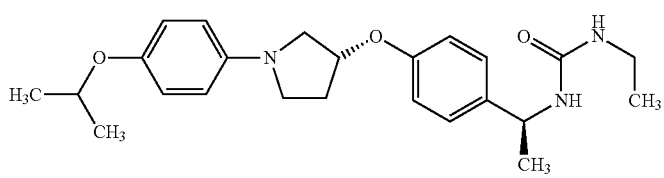 | A | 412 [M + H]+ | 1.24 (Q) |
| 3.11 | XXIII | 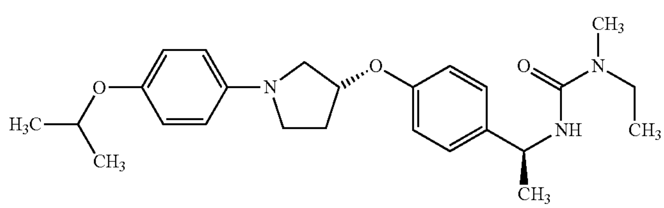 | A | 412 [M + H]+ | 1.31 (Q) |
| 3.12 | XXIII | 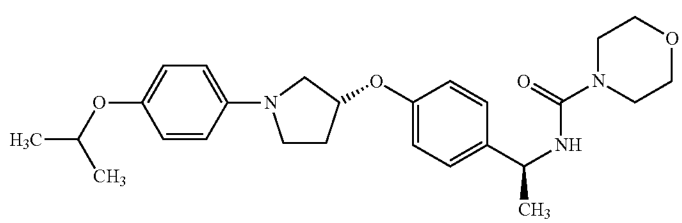 | A | 454 [M + H]+ | 1.24 (Q) |
| 3.13 | XXII.4 | 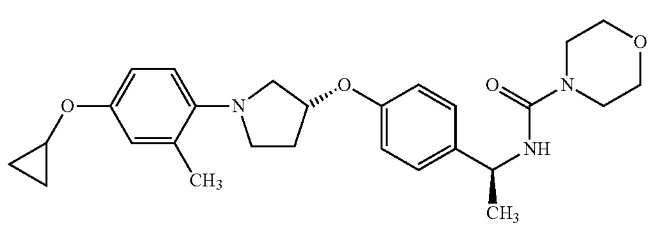 | B | 466 [M + H]+ | 1.00 (K) |

Example 4

Example 4.1

General Route

N—((S)-1-(4-((R)-1-(4-(3-methoxypropoxy)phenyl)pyrrolidin-3-yloxy)phenyl)ethyl)-acetamide

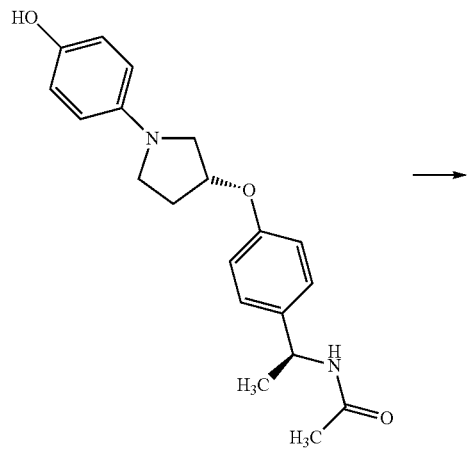

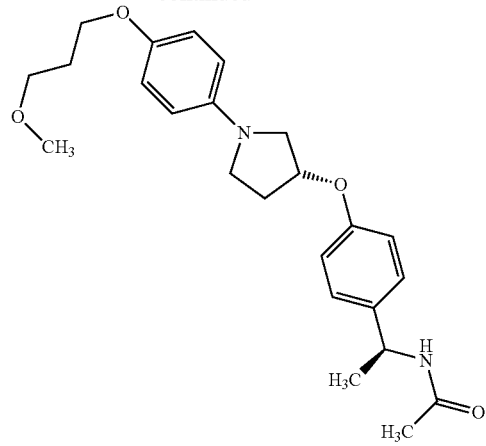

45.0 mg (0.13 mmol) of the phenol XXIV, 22.5 μL (0.20 mmol) 1-bromo-3-methoxypropane and 45.7 mg (0.33 mmol) $K_2CO_3$ are added to 1 mL DMF and stirred at 80° C. for 4 h. Afterwards the mixture is directly purified by HPLC (MeOH/$H_2O$/$NH_3$).

$C_{24}H_{32}N_2O_4$ (M=412.5 g/mol)

ESI-MS: 413 [M+H]$^+$ $R_t$ (HPLC): 1.10 min (method C)

The following compounds are prepared analogously to example 4.1.

For examples 4.5-4.7 ACN is used as solvent.

| Ex. | Alkylating agent | Structure | Mass spec result | HPLC retention time (method) |
|---|---|---|---|---|
| 4.1 | 1-bromo-3-methoxy-propane | 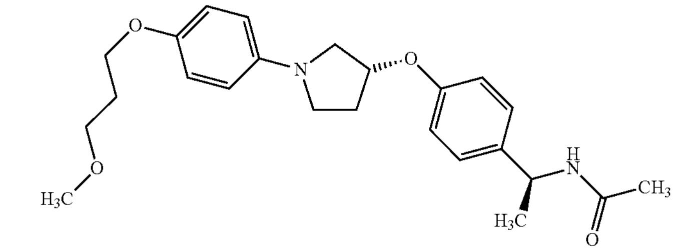 | 413 [M + H]$^+$ | 1.10 (C) |
| 4.2 | 1-bromo-cyclobutane carboxylic acid ethyl ester | 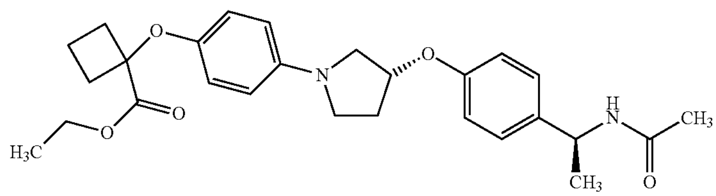 | 467 [M + H]$^+$ | 1.19 (C) |
| 4.3 | 2-bromo-butane | 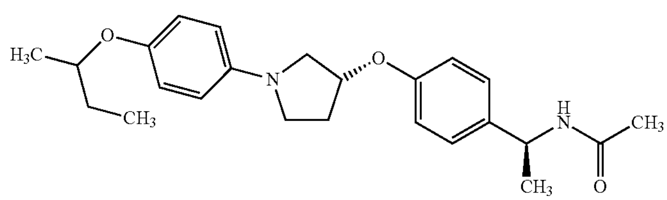 | 397 [M + H]$^+$ | 1.22 (C) |

-continued

| Ex. | Alkylating agent | Structure | Mass spec result | HPLC retention time (method) |
|---|---|---|---|---|
| 4.4 | 2-bromoethyl methyl ether | 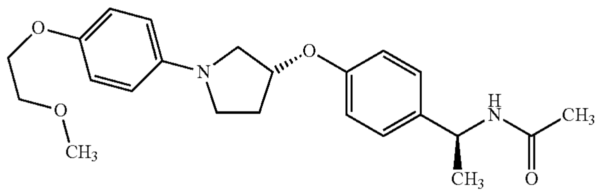 | 399 [M + H]⁺ | 1.03 (C) |
| 4.5 | benzyl bromide | 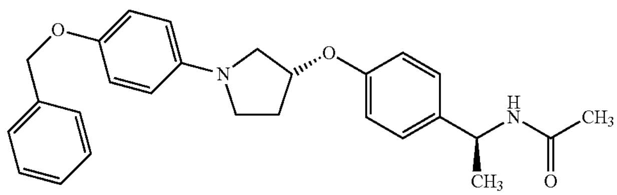 | 431 [M + H]⁺ | 1.23 (C) |
| 4.6 | 2-iodo-1,1-difluoro-ethane | 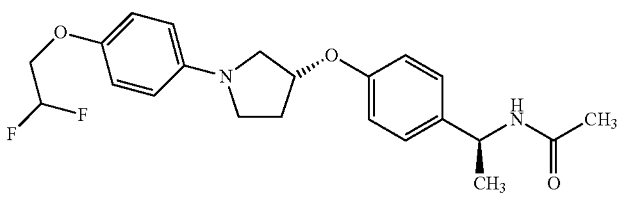 | 405 [M + H]⁺ | 1.08 (C) |
| 4.7 | 1,1,2,2-tetrafluoro-3-iodopropane | 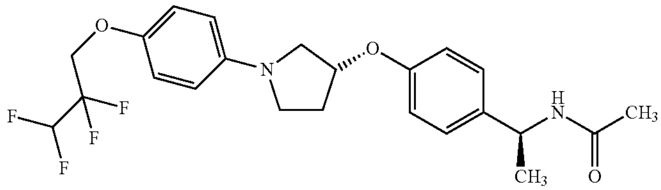 | 455 [M + H]⁺ | 1.16 (C) |

Example 5

Example 5.1

General Route

Methyl-(S)-1-(4-((R)-1-(4-(cyclopropylmethoxy)phenyl)pyrrolidin-3-yloxy)phenyl)-ethylcarbamate

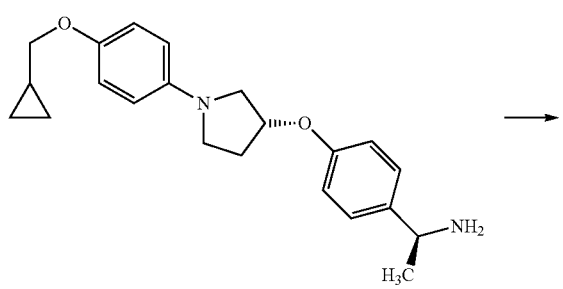

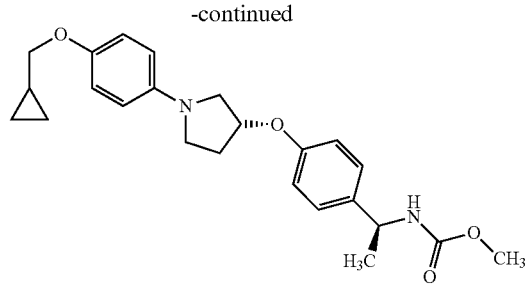

To 35.3 mg (0.10 mmol) of amine XXII.3 in 2 mL THF are added 42.7 μL (0.25 mmol) DIPEA and 11.6 μL (0.15 mmol) in 3 mL methyl chloroformate and the resulting mixture is stirred at r.t. over night. Then some DMF is added and the mixture is directly purified by HPLC (MeOH/H₂O/TFA).

$C_{24}H_{30}N_2O_4$ (M=410.5 g/mol)

ESI-MS: 411 [M+H]⁺

$R_t$ (HPLC): 1.96 min (method S)

The following compounds are prepared analogously to example 5.1.

| Ex. | Starting material | Structure | Mass spec result | HPLC retention time (method) |
|---|---|---|---|---|
| 5.1 | XXII.3 | 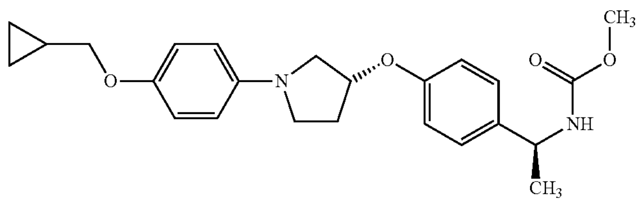 | 411 [M + H]+ | 1.96 (S) |
| 5.2 | XXIII | 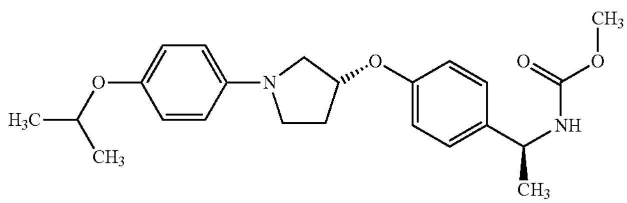 | 398 [M + H]+ | 1.35 (Q) |

Example 6

N—((S)-1-(4-((R)-1-(4-(Cyclopropylmethoxy)phenyl)pyrrolidin-3-yloxy)phenyl)-ethyl)-2,2,2-trifluoroacetamide

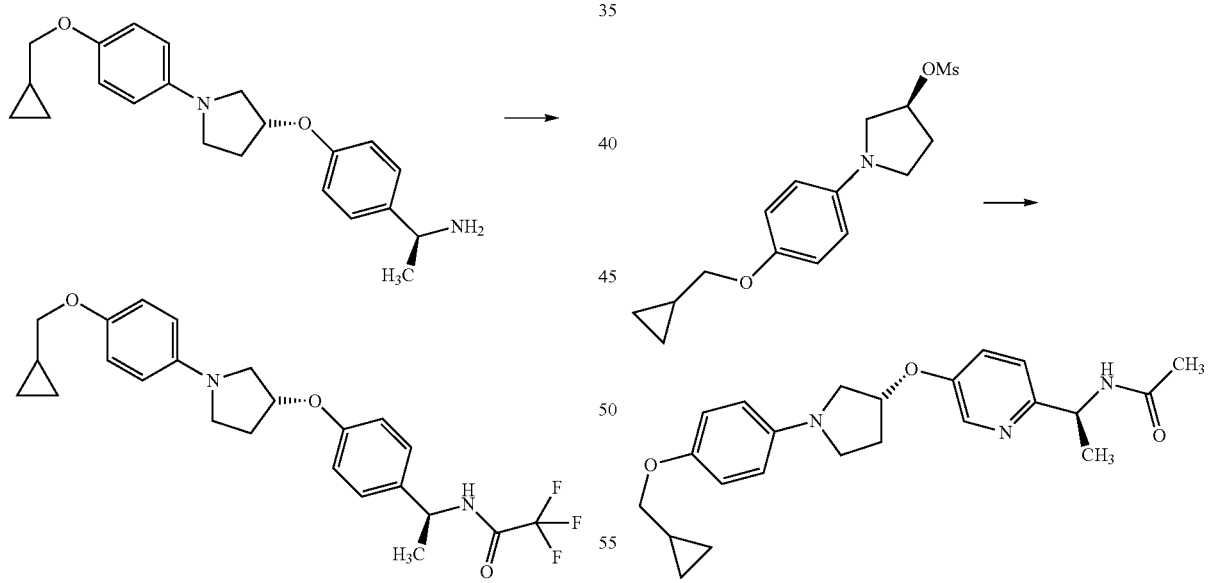

Example 7

Example 7.1

General Route

N—((S)-1-(5-((R)-1-(4-(Cyclopropylmethoxy)phenyl)pyrrolidin-3-ylox)pyridin-2-yl)ethyl)acetamide To 40.0 mg (0.11 mmol) of amine XXII.3 in 3 mL DCM are added 47.3 μL (0.34 mmol) trifluoroacetic acid anhydride and the mixture is stirred at r.t. for 30 min. Then the solvent is removed in vacuo and the residue is purified by HPLC (MeOH/H2O/TFA).

C24H27F3N2O3 (M=448.5 g/mol)
ESI-MS: 449 [M+H]+
Rt (HPLC): 1.53 min (method R)

To 50.0 mg (0.16 mmol) of example XXVIII and 30 mg (0.17 mmol) of example VI in 3 mL DMF are added 110 mg (0.34 mmol) Cs2CO3 and the mixture is stirred at 80° C. over night. After cooling down the mixture is directly purified by HPLC (MeOH/H2O/NH3).

C23H29N3O3 (M=395.5 g/mol)
ESI-MS: 396 [M+H]+
Rt (HPLC): 1.08 min (method E)

The following compounds are prepared analogously to example 7.1.

| Ex. | Starting material(s) | Structure | Mass spec result | HPLC retention time (method) |
|---|---|---|---|---|
| 7.1 | XXVIII + VI | 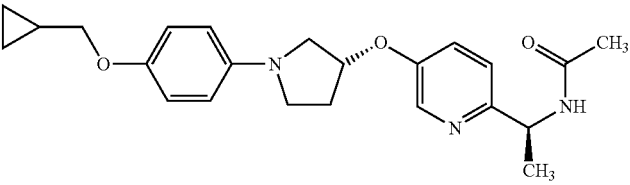 | 396 [M + H]⁺ | 1.08 (E) |
| 7.2 | XXVIII + IV.3 | 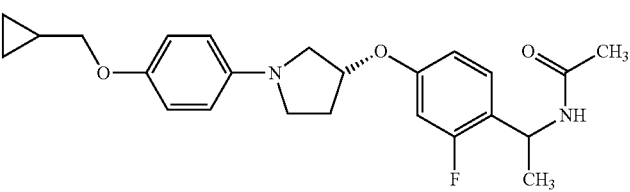 | 413 [M + H]⁺ | 1.26 (E) |
| 7.3 | XXVIII + V | 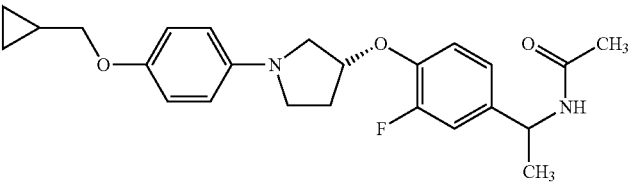 | 413 [M + H]⁺ | 1.24 (E) |

Example 8

Example 8.1

General Route

N—((S)-1-(4-((R)-1-(4-(Cyclopropylmethoxy)phenyl)pyrrolidin-3-yloxy)phenyl)-ethyl)-cyclopropanecarboxamide

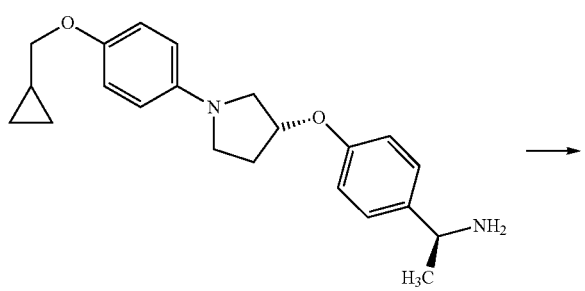

To 35.3 mg (0.11 mmol) of amine XXII.3 and 0.03 mL (0.20 mmol) DIPEA in 2 mL THF are added 27.2 µL (0.30 mmol) cyclopropylcarboxylic acid chloride and the mixture is stirred at r.t. for 2 h. Some DMF is added and the mixture purified by HPLC (MeOH/H₂O/TFA).

$C_{26}H_{32}N_2O_3$ (M=420.5 g/mol)

ESI-MS: 421 [M+H]⁺

$R_t$ (HPLC): 1.47 min (method R)

The following compounds are prepared analogously to example 8.1:

| Ex. | Starting material | Structure | Mass spec result | HPLC retention time (method) |
|---|---|---|---|---|
| 8.1 | XXII.3 | 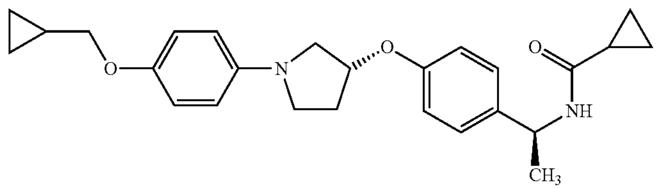 | 421 [M + H]+ | 1.47 (R) |
| 8.2 | XXIX.2 | 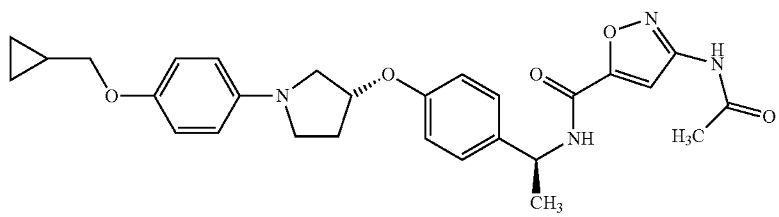 | 505 [M + H]+ | 1.42 (B) |
| 8.3 | XXII.3 | 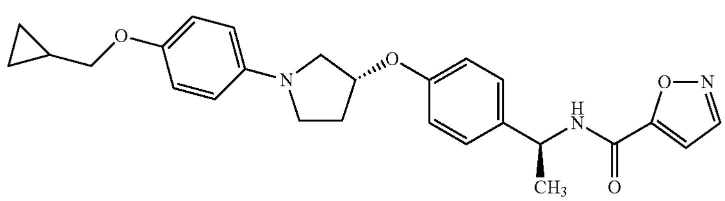 [SMILES: C[C@H](NC(=O)c1ccno1)c1ccc(O[C@@H]2CCN(c3ccc(OCC4CC4)cc3)C2)cc1] | 448 [M + H]+ | 0.63 (O) |
Example 9
(1S,3R)-3-Amino-N—((S)-1-(4-((R)-1-(4-(cyclopropylmethoxy)phenyl)pyrrolidin-3-yloxy)phenyl)ethyl-cyclopentylcarboxamide
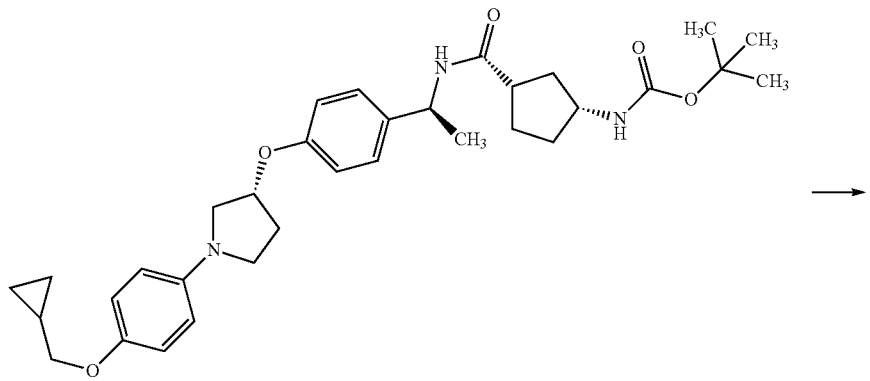

-continued

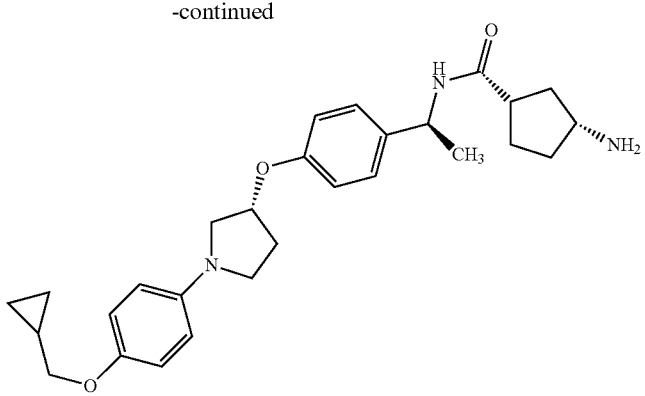

To 16.0 mg (0.03 mmol) of example XXIX.1 in 1 mL dioxane are added 10.0 µL of a HCl solution in dioxane (c=4 mol/l). The resulting mixture is stirred at r.t. over night and afterwards purified by HPLC (ACN/H$_2$O/NH$_3$).

$C_{24}H_{27}F_3N_2O_3$ (M=463.6 g/mol)
ESI-MS: 464 [M+H]$^+$
R$_t$ (HPLC): 1.35 min (method T)

Example 10

N—((S)-1-(4-((R)-1-(4-Ethoxyphenyl)pyrrolidin-3-yloxy)phenyl)-ethyl)-2-(2-hydroxyacetamido)-4-methylthiazole-5-carboxamide

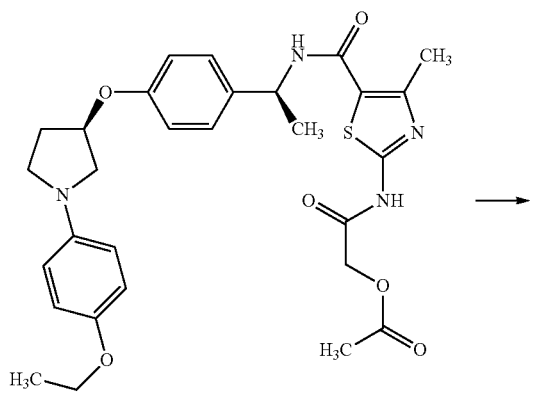

To 40.0 mg (0.07 mmol) of example 2.56 in 1 mL THF are added 0.14 mL (0.14 mmol) of an aq. LiOH solution (c=1 mol/L) and the mixture is stirred at r.t. for 3 h. Then water is added and the mixture is neutralized with aq. HCl solution (c=1 mol/L) and extracted with DCM. The org. layers are combined, dried over MgSO$_4$, filtered and the solvent is removed in vacuo. The crude product is purified by HPLC (ACN/H$_2$O/TFA).

$C_{27}H_{32}N_4O_5S$ (M=524.6 g/mol)
ESI-MS: 525 [M+H]$^+$
R$_t$ (HPLC): 0.94 min (method M)

Analytic Methods

| Method A | | |
|---|---|---|
| time (min) | Vol % water (incl. 0.2% NH$_4$OH) | Vol % MeOH |
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: XBridge C18 (Waters); 2.5 µm; 3.0×30 mm; column temperature: 40° C.; flow: 1.3 mL/min;

| Method B | | |
|---|---|---|
| time (min) | Vol % water (incl. 0.2% TFA) | Vol % MeOH |
| 0.00 | 95 | 5 |
| 0.05 | 95 | 5 |
| 1.40 | 0 | 100 |
| 1.80 | 0 | 100 |

Analytical column: Sunfire C18 (Waters) 2.5 µm; 3.0 × 30 mm; column temperature: 60° C.; flow: 2.2 ml/min.

| Method C | | |
|---|---|---|
| time (min) | Vol % water (incl. 0.2% NH$_4$OH) | Vol % MeOH |
| 0.0 | 95 | 5 |
| 0.05 | 95 | 5 |
| 1.40 | 0 | 100 |
| 1.80 | 0 | 100 |

Analytical column: XBridge C18 (Waters) 2.5 µm; 3.0 × 30 mm; column temperature: 60° C.; flow: 2.2 ml/min.

Method D

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3 |
| 1.40 | 0 | 100 | 3 |

Analytical column: Sunfire C18 (Waters) 2.5 µm; 3.0 × 30 mm; column temperature: 60° C..

Method E

| time (min) | Vol % water (incl. 0.1% TFA) | Vol % MeOH |
|---|---|---|
| 0.0 | 95 | 5 |
| 0.05 | 95 | 5 |
| 1.40 | 0 | 100 |
| 1.80 | 0 | 100 |

Analytical column: StableBond C18 (Waters) 1.8 µm; 3.0 × 30 mm; column temperature: 60° C.; flow: 2.2 ml/min.

Method F

| time (min) | Vol % water (incl. 0.1% FA) | Vol % ACN (incl. 0.1% FA) |
|---|---|---|
| 0.0 | 95 | 5 |
| 3.50 | 2 | 98 |
| 6.00 | 2 | 98 |

Analytical column: X-Bridge C18 (Waters) 3.5 µm; 2.1 × 50 mm; column temperature: 35° C.; flow: 0.8 ml/min.

Method G

| time (min) | Vol % water (incl. 0.1% FA) | Vol % ACN (incl. 0.1% FA) |
|---|---|---|
| 0.0 | 95 | 5 |
| 1.60 | 2 | 98 |
| 3.00 | 2 | 98 |

Analytical column: X-Bridge C18 (Waters) 3.5 µm; 2.1 × 50 mm; column temperature: 35° C.; flow: 1.0 ml/min.

Method H

| time (min) | Vol % water (incl. 0.1% NH$_4$OH) | Vol % MeOH | Flow [ml/min] |
|---|---|---|---|
| 0.0 | 95 | 5 | 2.2 |
| 0.30 | 95 | 5 | 2.2 |
| 1.50 | 0 | 100 | 2.2 |
| 1.55 | 0 | 100 | 2.9 |
| 1.70 | 0 | 100 | 2.9 |

Analytical column: XBridge C18 (Waters) 2.5 µm; 3.0 × 30 mm; column temperature: 60° C.

Method I

| time (min) | Vol % water (incl. 0.05% TFA) | Vol % ACN |
|---|---|---|
| 0.0 | 40 | 60 |
| 6 | 10 | 90 |
| 15 | 10 | 90 |
| 15.1 | 40 | 60 |

Analytical column: XBridge C18 (Waters) 3.5 µm; 4.6 × 50 mm; column temperature: r.t.;.

Method J

| time (min) | Vol % water (incl. 0.01M NH$_4$OAc) | Vol % ACN |
|---|---|---|
| 0.0 | 50 | 50 |
| 6 | 10 | 90 |
| 15 | 10 | 90 |
| 15.1 | 40 | 60 |

Analytical column: Eclipse-XDB-C18 (Agilent), 5.0 µm; 4.6 × 150 mm; column temperature: r.t.; flow: 1.0 ml/min.

Method K

| time (min) | Vol % water (incl. 0.1% NH$_4$OH) | Vol % MeOH | Flow [ml/min] |
|---|---|---|---|
| 0.0 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: XBridge C18 (Waters) 2.5 µm; 3.0 × 30 mm; column temperature: 60° C.

Method L

| time (min) | Vol % water (incl. 0.1% NH$_4$OH) | Vol % MeOH |
|---|---|---|
| 0.0 | 95 | 5 |
| 0.15 | 95 | 5 |
| 1.70 | 0 | 100 |
| 2.10 | 0 | 100 |

Analytical column: XBridge C18 (Agilent) 3.5 µm; 4.6 × 30 mm; column temperature: 60° C.; flow: 4 ml/min

Method M

| time (min) | Vol % water (incl. 0.1% TFA) | Vol % ACN | Flow [ml/min] |
|---|---|---|---|
| 0.0 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Stable Bond C18 (Agilent) 1.8 µm; 3.0 × 30 mm; column temperature: 60° C.

Method N

| time (min) | Vol % water (incl. 0.1% TFA) | Vol % MeOH (incl. 0.1% TFA) | Flow [ml/min] |
| --- | --- | --- | --- |
| 0.0 | 95 | 5 | 4.0 |
| 0.15 | 95 | 5 | 4.0 |
| 1.70 | 0 | 100 | 4.0 |
| 2.25 | 0 | 100 | 4.0 |

Analytical column: Sunfire C18 (Waters) 3.5 µm; 4.6 × 30 mm; column temperature: 60° C.

Method O

| time (min) | Vol % water (incl. 0.1% TFA) | Vol % ACN |
| --- | --- | --- |
| 0.00 | 95.0 | 5.0 |
| 0.70 | 1.0 | 99.0 |
| 0.80 | 1.0 | 99.0 |
| 0.81 | 95.0 | 5.0 |

Analytical column: Ascentis Express C18; 2.1 × 50 mm; 2.7 µm; column temperature: 60° C.; flow: 1.5 mL/min;

Method P

| time (min) | Vol % water (incl. 0.1% TFA) | Vol % ACN (incl. 0.08% TFA) |
| --- | --- | --- |
| 0.0 | 95.0 | 5.0 |
| 0.75 | 0.0 | 100.0 |
| 0.85 | 0.0 | 100.0 |

Analytical column: Sunfire C18 (Waters) 2.5 µm; 2.1 × 50 mm; column temperature: 60° C.; flow: 1.5 ml/min.

Method Q

| time (min) | Vol % water (incl. 0.1% NH$_4$OH) | Vol % ACN |
| --- | --- | --- |
| 0.00 | 98.0 | 2.0 |
| 1.50 | 0.0 | 100.0 |
| 1.80 | 0.0 | 100.0 |

Analytical column: Xbridge C18 (Waters) 3.5 µm; 4.6 × 30 mm; column temperature: 60° C.; flow: 2.5 ml/min.

Method R

| time (min) | Vol % water (incl. 0.1% TFA) | Vol % MeOH | Flow [ml/min] |
| --- | --- | --- | --- |
| 0.00 | 95 | 5 | 1.8 |
| 0.25 | 95 | 5 | 1.8 |
| 1.70 | 0 | 100 | 1.8 |
| 1.75 | 0 | 100 | 2.5 |
| 1.90 | 0 | 100 | 2.5 |

Analytical column: Sunfire C18 (Waters) 2.5 µm; 3.0 × 30 mm; column temperature: 60° C.

Method S

| time (min) | Vol % water (incl. 0.1% TFA) | Vol % MeOH | Flow [ml/min] |
| --- | --- | --- | --- |
| 0.00 | 95 | 5 | 4.0 |
| 0.05 | 95 | 5 | 3.0 |
| 2.05 | 0 | 100 | 3.0 |
| 2.10 | 0 | 100 | 4.5 |
| 2.40 | 0 | 100 | 4.5 |

Analytical column: Sunfire C18 (Waters) 2.5 µm; 4.6 × 30 mm; column temperature: 60° C.

Method T

| time (min) | Vol % water (incl. 0.1% FA) | Vol % MeOH | Flow [ml/min] |
| --- | --- | --- | --- |
| 0.00 | 95 | 5 | 2.2 |
| 0.05 | 95 | 5 | 2.2 |
| 1.40 | 0 | 100 | 2.2 |
| 1.80 | 0 | 100 | 2.2 |

Analytical column: Sunfire C18 (Waters) 2.5 µm; 3.0 × 30 mm; column temperature: 60° C.

Method U

| time (min) | Vol % water | Vol % ACN (incl. 0.1% TFA) | Flow [ml/min] |
| --- | --- | --- | --- |
| 0.00 | 98 | 2 | 2.5 |
| 1.50 | 0 | 100 | 2.5 |
| 1.80 | 0 | 100 | 2.5 |

Analytical column: Sunfire C18 (Waters) 3.5 µm; 4.6 × 30 mm; column temperature: 60° C.

Method V

| time (min) | Vol % water (incl. 0.1% FA) | Vol % ACN (incl. 0.1% FA) | Flow [ml/min] |
| --- | --- | --- | --- |
| 0.00 | 90 | 10 | 1.5 |
| 4.50 | 10 | 90 | 1.5 |
| 5.00 | 10 | 90 | 1.5 |
| 5.50 | 90 | 10 | 1.5 |

Analytical column: Cromolith Speed ROD RP18e (Merck); 4.6 × 50 mm; column temperature: r.t..

Method W

| time (min) | Vol % water (incl. 0.1% NH$_3$) | Vol % ACN | Flow [ml/min] |
| --- | --- | --- | --- |
| 0.00 | 98 | 2 | 2.0 |
| 1.20 | 0 | 100 | 2.0 |
| 1.10 | 0 | 100 | 2.0 |

Analytical column: Xbridge C18 (Waters) 2.5 µm; 3.0 × 30 mm; column temperature: 60° C.

| Method X | | | |
|---|---|---|---|
| time (min) | Vol % water (incl. 0.1% TFA) | Vol % ACN | Flow [ml/min] |
| 0.00 | 98 | 2 | 2.5 |
| 1.20 | 0 | 100 | 2.5 |
| 1.40 | 0 | 100 | 2.5 |

Analytical column: Sunfire C18 (Waters) 3.5 μm; 4.6 × 30 mm; column temperature: 60° C.

The invention claimed is:
1. A compound of formula I

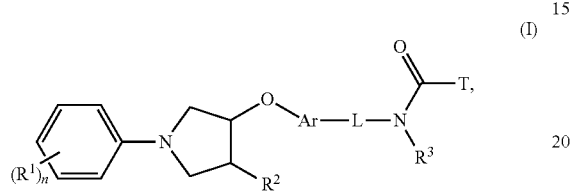

wherein
Ar is phenylene or pyridinylene, which are each optionally substituted with one or two substituents independently selected from F, Cl, —O—CH$_3$ and CH$_3$;
R$^1$ independently of one another are selected from a group consisting of halogen, CN, C$_{1-4}$-alkyl, C$_{3-6}$-cycloalkyl, —O—(C$_{1-6}$-alkyl), —O—(C$_{3-6}$-cycloalkyl), —O—(CH$_2$)$_{1-2}$—(C$_{3-6}$-cycloalkyl), —O—CH$_2$—R$^4$, —O-tetrahydrofuranyl and —O-heteroaryl,
wherein R$^4$ is tetrahydrofuranyl, aryl or heteroaryl,
wherein heteroaryl is selected from the group consisting of pyridinyl, pyrimidinyl, pyridazinyl and pyrazinyl,
wherein aryl is selected from the group consisting of phenyl and naphthyl,
wherein each alkyl is optionally substituted with 1 to 6 F or with one —OH or one —O—C$_{1-3}$-alkyl
wherein each cycloalkyl is optionally substituted with 1 to 4 F or with one CH$_3$, CF$_3$ or —CO$_2$(C$_{1-3}$-alkyl), and
wherein each tetrahydrofuranyl, aryl or heteroaryl is optionally substituted with one or two substituents independently selected from F, Cl, C$_{1-3}$-alkyl or —O—CH$_3$;
or two R$^1$ groups attached to adjacent C-atoms together may form an C$_{3-5}$-alkylene bridging group in which one or two —CH$_2$-groups may be replaced by O and the alkylene bridge may optionally be substituted by one or two F or CH$_3$;
n is 1, 2 or 3;
R$^2$ is H, F, CN or —O—(C$_{1-3}$-alkyl),
wherein the alkyl group is optionally substituted with —OCH$_3$;
R$^3$ is H or C$_{1-3}$-alkyl;
L is a straight-chain C$_{1-3}$-alkylene group which is optionally substituted with one or two C$_{1-3}$-alkyl groups; and
T is selected from a group consisting of:
C$_{1-4}$-alkyl which is optionally substituted with one to three F or with one CN, OH, —O—CH$_3$, —O—C(=O)—CH$_3$ or a heteroaryl group selected from the group consisting of pyrrolyl, isoxazolyl, pyrimidinyl and pyrazinyl,
wherein each of said heteroaryl groups is optionally substituted with C$_{1-3}$-alkyl;
C$_{3-6}$-cycloalkyl which is optionally substituted with one or two F, CN, CH$_3$, OH, —O—(C$_{1-3}$-alkyl), NH$_2$, —NH—(C=O)CH$_3$, —C(=O)—NH$_2$, —C(=O)—NH(C$_{1-3}$-alkyl) or —C(=O)—N(C$_{1-3}$-alkyl)$_2$;
—O—(C$_{1-2}$-alkyl);
morpholinyl;
—NH$_2$, wherein each H is optionally independently replaced with C$_{1-3}$-alkyl or wherein one H is optionally replaced with a 5-membered heteroaryl group containing 1 to 3 heteroatoms selected independently from O, S, N and NH, wherein said heteroaryl group is optionally substituted with C$_{1-3}$-alkyl, or with a —CH$_2$-pyrimidyl group;
a 5-membered heteroaryl group containing one or two heteroatoms selected independently from O, S, N and NH, which is optionally substituted with one or two substituents selected independently from the group consisting of: Cl, CN, NH$_2$, —NH—C(=O)—C$_{1-3}$-alkyl, —NH—C(=O)—CH$_2$OH, —NH—C(=O)—CH$_2$OCH$_3$, —NH—C(=O)—CH$_2$O—C(=O)CH$_3$, —NH—C(=O)—CH$_2$OCH$_2$-Ph, C$_{1-3}$-alkyl and —O—(C$_{1-2}$-alkyl), wherein each alkyl group is optionally substituted with one to three F or with one OH;
a 6-membered heteroaryl group containing 1 or 2 N, which is optionally substituted with —CH$_3$ or —C(=O)—NH(CH$_3$);
phenyl optionally substituted with F, Cl, CN or OCH$_3$; and
a group selected from among:

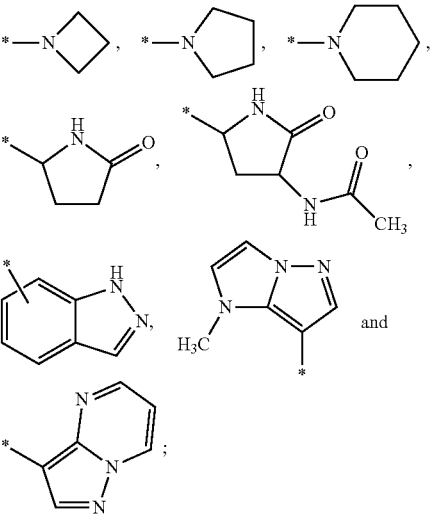

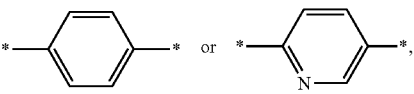

or a tautomer or salt thereof.
2. A compound according to claim 1, wherein
Ar is

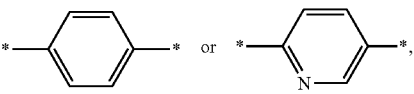

wherein the right-hand side of the above Ar groups is linked to L, and the left-hand side of the above moieties is linked to the oxygen figuring in formula (I); and
wherein the before mentioned phenyl group is optionally monosubstituted with F, R$^2$ is H, F, —O—CH$_3$ or —O—CH$_2$CH$_2$OCH$_3$; and
R$^3$ is H.

3. A comound according to claim 2, wherein
Ar is

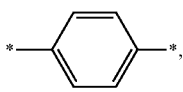

wherein the before mentioned group is optionally monosubstituted with F.

4. A compound according to claim 1, wherein
L is —CH(CH₃)—; and
R² is H.

5. A compound according to claim 1, wherein R¹ is selected from a group consisting of:
F, Cl, Br, CN, C₁₋₄-alkyl, C₃₋₅-cycloalkyl, —O—(C₁₋₄-alkyl), —O—(C₃₋₅-cycloalkyl), —O—CH₂—(C₃₋₅-cycloalkyl), —O—CH₂-aryl, —O-tetrahydrofuranyl and —O-heteroaryl,
  wherein heteroaryl is selected from the group consisting of pyridinyl, pyrimidinyl, pyridazinyl and pyrazinyl,
  wherein aryl is phenyl or naphthyl,
  wherein each alkyl is optionally substituted with 1 to 3 F or with one —O—CH₃, and
  wherein each cycloalkyl is optionally substituted with 1 to 2 F or with one CH₃, CF₃ or —CO₂CH₃;
or two R¹ groups attached to adjacent C-atoms together may form a —(CH₂)₂—O—, —O—CH₂—O—, —O—(CH₂)₂—O— or —O—(CH₂)₃—O— bridge that is optionally substituted with one or two F or CH₃.

6. A compound according to claim 1, wherein R¹ is selected from a group consisting of:
F, Cl, CN, C₁₋₄-alkyl, —O—(C₁₋₄-alkyl), —O—(C₃₋₅-cycloalkyl),

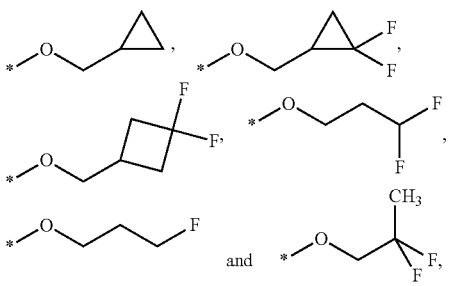

or two R¹ groups attached to adjacent C-atoms together may form a —O—(CH₂)₂—O— or —O—(CH₂)₃—O— bridge.

7. A compound according to claim 1, wherein T is selected from a group consisting of:
C₁₋₃-alkyl which is optionally substituted with one to three F or with one CN, OH or —OCH₃;
cyclopropyl which is optionally substituted with one or two F or with one CN, CH₃, OH, —OCH₃ or —(C=O)—N(CH₃)₂;
—OCH₃;
—NH₂, wherein each H is optionally independently replaced with C₁₋₃-alkyl or wherein one H is optionally replaced by isoxazolyl or by —CH₂-pyrimidyl; and
a 5-membered heteroaryl group selected from imidazolyl, oxazolyl, pyrazolyl, isoxazolyl, thioazolyl and isothiazolyl,
  wherein said 5-membered heteroaryl group is optionally substituted with one or two substituents selected independently from the group consisting of:
  Cl, CN, NH₂, —NH—C(=O)—C₁₋₃-alkyl, —NH—C(=O)—CH₂OCH₃, —NH—C(=O)—CH₂O—C(=O)CH₃, —NH—C(=O)—CH₂OCH₂-Ph, —O—CH₃ and C₁₋₂-alkyl,
  wherein each alkyl is optionally substituted with one to three F.

8. A compound according to claim 1, wherein T is selected from a group consisting of: CH₃,

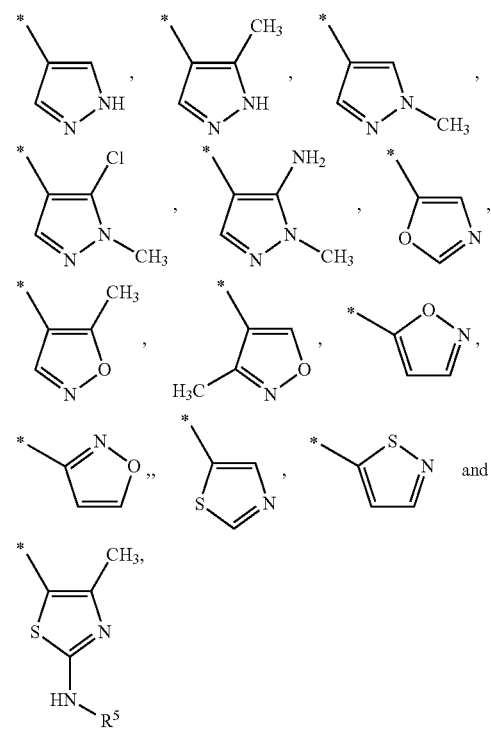

wherein R⁵ is H, —(C=O)—(C₁₋₂-alkyl), —(C=O)CH₂OCH₃, —(C=O)—CH₂O—C(=O)CH₃ or —(C=O)—CH₂OCH₂-Ph.

9. A compound according to claim 1 having the formula (I.1)

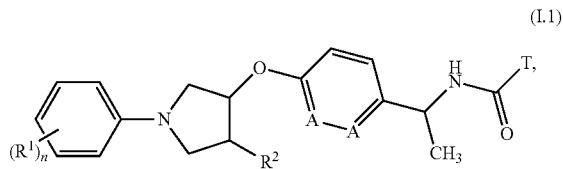

wherein
A are each independently from one another selected from the group consisting of CH, CF and N, with the proviso that 0 or 1 A may be N;
n is 1, 2 or 3;
R¹ is selected from a group consisting of F, Cl, Br, CN, C₁₋₃-alkyl, C₃₋₅-cycloalkyl, —O—(C₁₋₄-alkyl), —O—(C₃₋₅-cycloalkyl), —O—CH₂—(C₃₋₅-cycloalkyl), —O-tetrahydrofuranyl and —O-heteroaryl,
  wherein heteroaryl is selected from the group consisting of pyridinyl, pyrimidinyl, pyridazinyl and pyrazinyl, wherein each alkyl is optionally substituted with 1 to 3 F or with one —O—CH₃, and wherein each cycloalkyl is optionally substituted with 1 to 2 F or with one CF₃ or one —CO₂CH₃;

or two R¹ groups attached to adjacent C-atoms together may form a —(CH₂)₂—O—, —O—CH₂—O—, —O—(CH₂)₂—O— or —O—(CH₂)₃—O— bridge that is optionally substituted with one or two substituents selected form F and CH₃;

R² is H, F, —O—CH₃ or —O—CH₂CH₂OCH₃; and

T is selected from a group consisting of:

—CH₃, —CHF₂, —CF₃, —CH₂CN, —CH₂OH, —CH₂CH₃, —OCH₃,

—NH(CH₃), —N(CH₃)₂, —N(CH₃)(CH₂CH₃), —NH(CH₂CH₃),

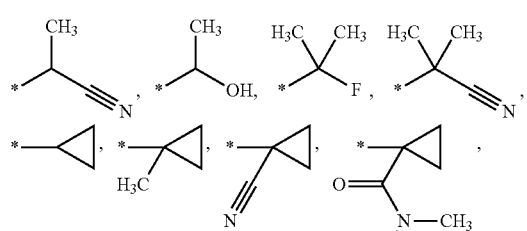

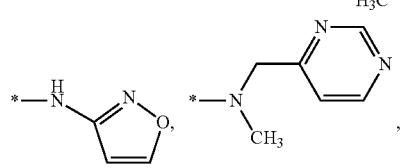

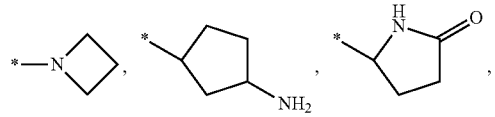

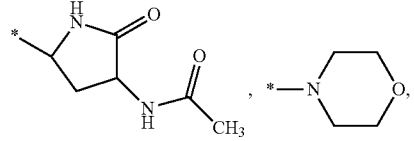

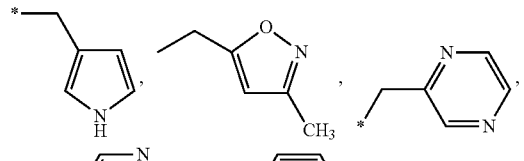

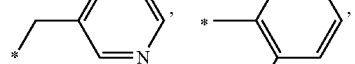

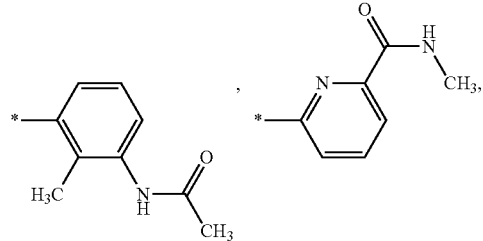

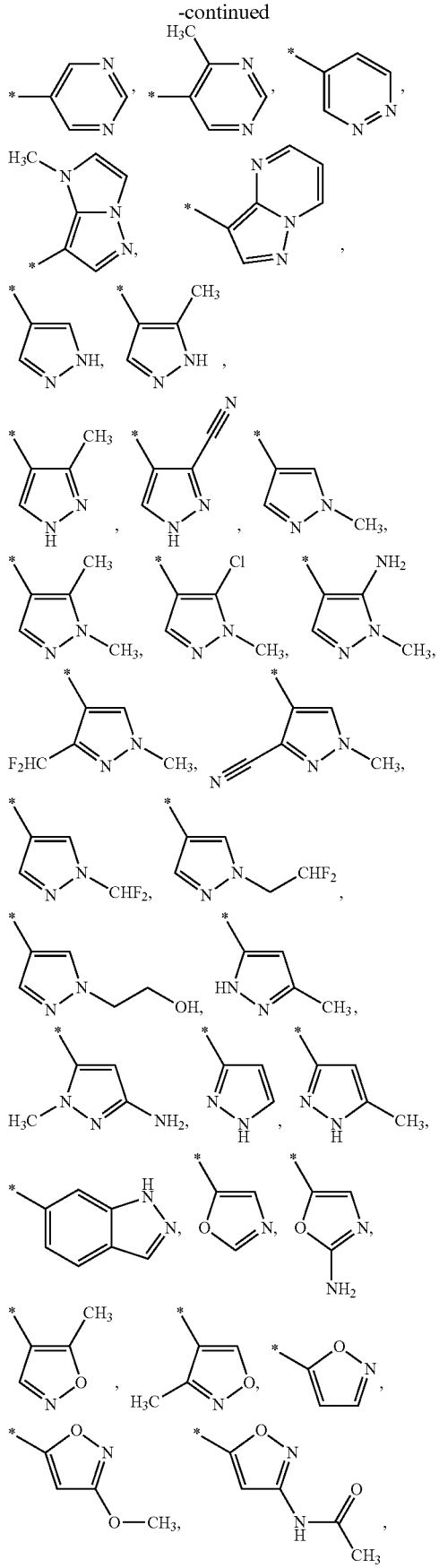

173

-continued

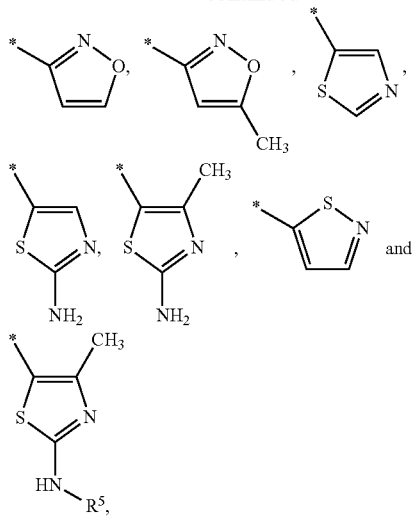

wherein R⁵ is H, —(C=O)—(C$_{1-2}$-alkyl), —(C=O)—CH$_2$OCH$_3$, —(C=O)—CH$_2$O—C(=O)CH$_3$ or —(C=O)—CH$_2$OCH$_2$-Ph;

or a tautomer or salt thereof.

10. A compound according to claim 1 having the formula

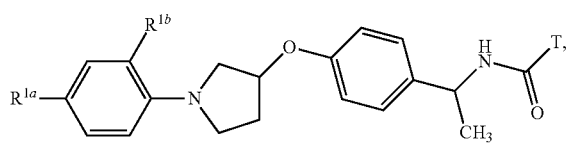

(I.4)

wherein
R$^{1a}$ is —O—(C$_{1-3}$-alkyl), —O—(C$_{3-4}$-cycloalkyl),

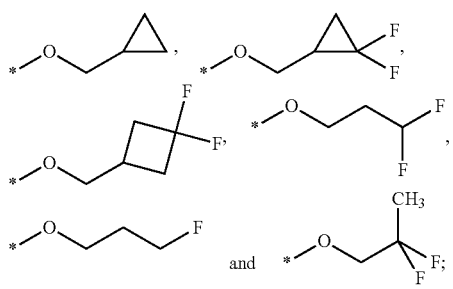

R$^{1b}$ is H, F, Cl, CN, CH$_3$ or OCH$_3$; and
T is C$_{1-3}$-alkyl which is optionally substituted with one to three F or with one CN;

—OCH$_3$;
—NH$_2$, wherein each H is optionally independently replaced with methyl or ethyl;

174

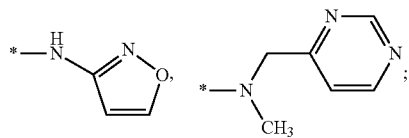

a 5-membered heteroaryl group selected from:

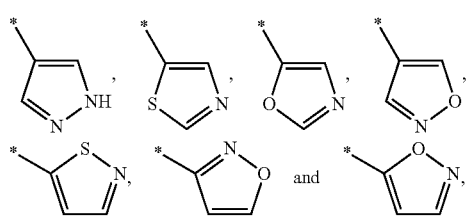

wherein said 5-membered heteroaryl group is optionally substituted with one or two substituents selected independently from the group consisting of: Cl, CN, NH$_2$, —NH—C(=O)—C$_{1-3}$-alkyl, —NH—C(=O)—CH$_2$OCH$_3$, —NH—C(=O)—CH$_2$O—C(=O)CH$_3$, —NH—C(=O)—CH$_2$OCH$_2$-Ph and CH$_3$;

or a tautomer or pharmaceutically acceptable salt thereof.

11. A compound according to claim 1 selected from:

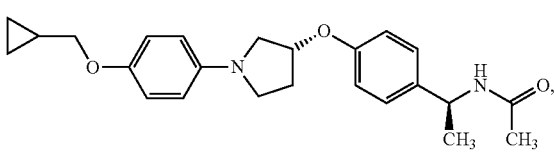

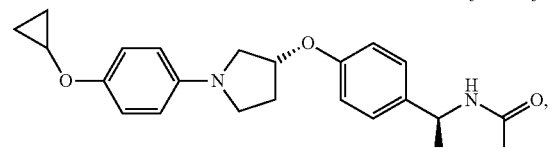

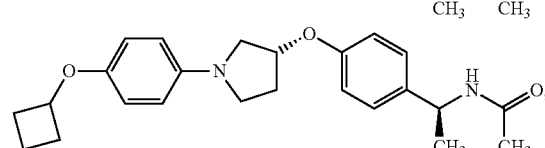

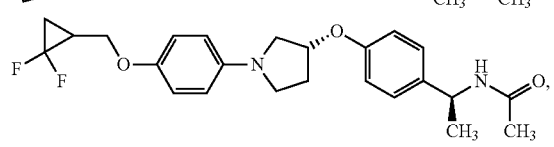

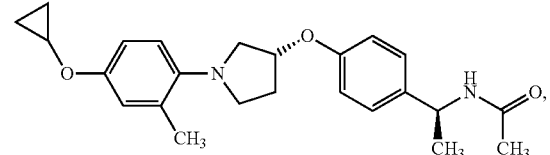

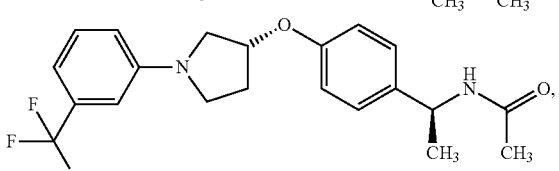

-continued

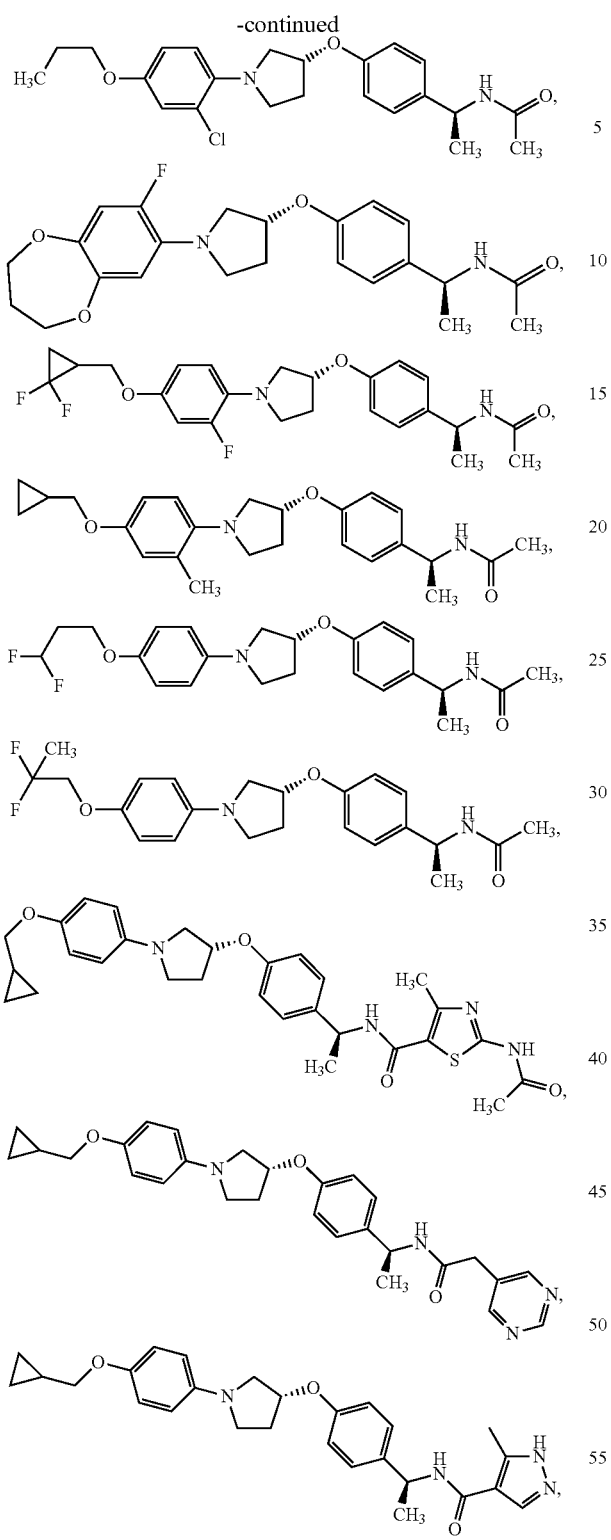

-continued

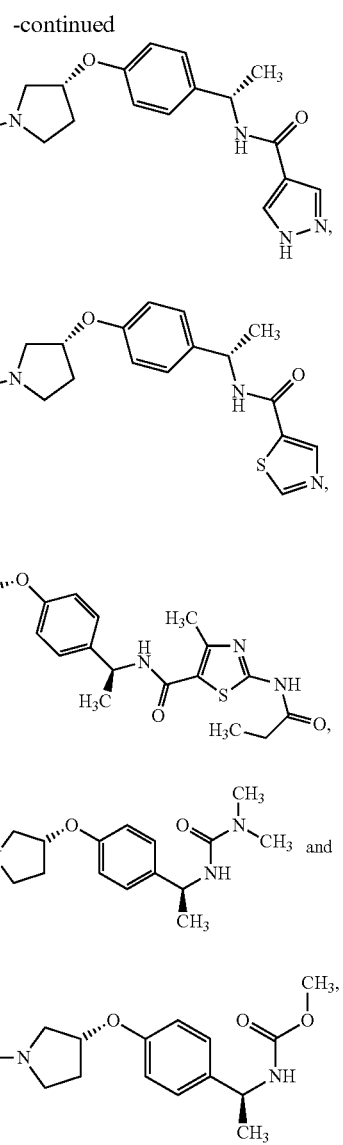

or a pharmaceutically acceptable salt thereof.

12. A pharmaceutically acceptable salt of a compound according to any claim 1.

13. A method for treating obesity or type 2 diabetes which comprises administering to a host suffering from obesity or type 2 diabetes a therapeutically effective amount of a compound according to claim 1.

14. A pharmaceutical composition comprising a compound according to claim 1, together with one or more inert carriers and/or diluents.

* * * * *